US008168223B1

(12) United States Patent
Tarara et al.

(10) Patent No.: US 8,168,223 B1
(45) Date of Patent: *May 1, 2012

(54) ENGINEERED PARTICLES AND METHODS OF USE

(75) Inventors: Thomas E. Tarara, San Diego, CA (US); Jeffry G. Weers, San Diego, CA (US); Alexey Kabalnov, Corvallis, OR (US); Ernest G. Schutt, San Diego, CA (US); Luis A. Dellamary, San Marcos, CA (US)

(73) Assignee: Novartis Pharma AG, Basel (CH)

( * ) Notice: Subject to any disclaimer, the term of this patent is extended or adjusted under 35 U.S.C. 154(b) by 148 days.

This patent is subject to a terminal disclaimer.

(21) Appl. No.: 09/886,296

(22) Filed: Jun. 21, 2001

Related U.S. Application Data

(60) Division of application No. 09/219,736, filed on Dec. 22, 1998, now Pat. No. 6,565,885, which is a continuation of application No. PCT/US98/20602, filed on Sep. 29, 1998, which is a continuation-in-part of application No. 09/133,848, filed on Aug. 14, 1998, now abandoned, which is a continuation-in-part of application No. 09/106,932, filed on Jun. 29, 1998, now abandoned.

(60) Provisional application No. 60/060,337, filed on Sep. 29, 1997.

(51) Int. Cl.
*A61K 9/14* (2006.01)
*A61K 9/127* (2006.01)
(52) U.S. Cl. .................... 424/489; 424/46; 424/450
(58) Field of Classification Search ............... 424/1.13, 424/1.21, 400, 489, 490, 450, 40, 422, 434, 424/497, 43, 46, 1.29, DIG. 7; 514/951, 514/963, 946
See application file for complete search history.

(56) References Cited

U.S. PATENT DOCUMENTS

| 979,993 | A | 10/1910 | O'Byrne et al. |
| 1,855,591 | A | 4/1932 | Wallerstein |
| 2,457,036 | A | 12/1948 | Epstein |
| 2,797,201 | A | 6/1957 | Veatch et al. |
| 3,014,844 | A | 12/1961 | Thiel et al. |
| 3,362,405 | A | 1/1968 | Hazel |
| 3,555,717 | A | 1/1971 | Chivers |
| 3,619,294 | A | 11/1971 | Black et al. |
| 3,362,357 | A | 1/1972 | Childs |
| 3,655,442 | A | 4/1972 | Schwer et al. |
| 3,745,682 | A | 7/1973 | Waldeisen |

(Continued)

FOREIGN PATENT DOCUMENTS

AU 714998 1/1997

(Continued)

OTHER PUBLICATIONS translation of WO 97/26863.*

(Continued)

*Primary Examiner* — Sharmila G. Landau
*Assistant Examiner* — Rachel Welter
(74) *Attorney, Agent, or Firm* — Janah & Associates, P.C.

(57) ABSTRACT

Engineered particles are provided may be used for the delivery of a bioactive agent to the respiratory tract of a patient. The particles may be used in the form of dry powders or in the form of stabilized dispersions comprising a nonaqueous continuous phase. In particularly preferred embodiments the particles may be used in conjunction with an inhalation device such as a dry powder inhaler, metered dose inhaler or a nebulizer.

44 Claims, 6 Drawing Sheets

U.S. PATENT DOCUMENTS

| | | |
|---|---|---|
| 3,812,854 A | 5/1974 | Michaels et al. |
| 3,948,263 A | 4/1976 | Drake, Jr. et al. |
| 3,957,964 A | 5/1976 | Grimm, III |
| 3,964,483 A | 6/1976 | Mathes |
| 3,975,512 A | 8/1976 | Long, Jr. |
| 4,009,280 A | 2/1977 | Macarthur et al. |
| 4,036,223 A | 7/1977 | Obert |
| 4,089,120 A | 5/1978 | Kozischek |
| 4,098,273 A | 7/1978 | Glenn |
| 4,102,999 A | 7/1978 | Umezawa et al. |
| 4,127,502 A | 11/1978 | Li Mutti et al. |
| 4,127,622 A | 11/1978 | Watanabe et al. |
| 4,158,544 A | 6/1979 | Louderback |
| 4,159,319 A | 6/1979 | Bachmann et al. |
| 4,161,516 A | 7/1979 | Bell |
| 4,180,593 A | 12/1979 | Cohan |
| 4,201,774 A * | 5/1980 | Igarashi et al. ............... 424/180 |
| 4,211,769 A | 7/1980 | Okada et al. |
| 4,244,949 A | 1/1981 | Gupta |
| 4,253,468 A | 3/1981 | Lehmbeck |
| 4,326,524 A | 4/1982 | Drake, Jr. et al. |
| 4,327,076 A | 4/1982 | Puglia et al. |
| 4,327,077 A | 4/1982 | Puglia et al. |
| 4,358,442 A | 11/1982 | Wirtz-Peitz et al. |
| 4,371,557 A | 2/1983 | Oppy et al. |
| 4,397,799 A | 8/1983 | Edgren et al. |
| 4,404,228 A | 9/1983 | Cloosterman et al. |
| 4,407,786 A | 10/1983 | Drake et al. |
| 4,452,239 A | 6/1984 | Malem |
| 4,484,577 A | 11/1984 | Sackner et al. |
| 4,534,343 A | 8/1985 | Nowacki et al. |
| 4,571,334 A | 2/1986 | Yoshida et al. |
| 4,588,744 A | 5/1986 | McHugh |
| 4,590,206 A | 5/1986 | Forrester et al. |
| 4,591,552 A | 5/1986 | Neurath |
| 4,613,500 A | 9/1986 | Suzuki et al. |
| 4,617,272 A | 10/1986 | Kirkwood et al. |
| 4,620,847 A | 11/1986 | Shishov et al. |
| 4,659,696 A | 4/1987 | Hirai et al. |
| 4,680,027 A | 7/1987 | Parsons et al. |
| 4,684,719 A | 8/1987 | Nishikawa et al. |
| 4,701,417 A | 10/1987 | Portenhauser et al. |
| 4,713,249 A | 12/1987 | Schröder |
| 4,721,709 A | 1/1988 | Seth et al. |
| 4,739,754 A | 4/1988 | Shaner |
| 4,758,583 A | 7/1988 | Cerami et al. |
| 4,761,400 A | 8/1988 | Doat et al. |
| 4,762,857 A | 8/1988 | Bollin, Jr. et al. |
| 4,765,987 A | 8/1988 | Bonte et al. |
| 4,790,824 A | 12/1988 | Morrow et al. |
| 4,793,997 A | 12/1988 | Drake et al. |
| 4,812,444 A | 3/1989 | Mitsuhashi et al. |
| 4,814,436 A | 3/1989 | Shibata et al. |
| 4,818,542 A | 4/1989 | DeLuca et al. |
| 4,819,629 A | 4/1989 | Jonson |
| 4,824,938 A | 4/1989 | Koyama et al. |
| 4,830,858 A | 5/1989 | Payne et al. |
| 4,847,079 A | 7/1989 | Kwan |
| 4,855,326 A | 8/1989 | Fuisz |
| 4,861,627 A | 8/1989 | Mathiowitz et al. |
| 4,865,871 A | 9/1989 | Livesey et al. |
| 4,866,051 A | 9/1989 | Hunt |
| 4,883,762 A | 11/1989 | Hoskins |
| 4,891,319 A | 1/1990 | Roser |
| 4,904,479 A | 2/1990 | Illum |
| 4,906,463 A | 3/1990 | Cleary et al. |
| 4,907,583 A | 3/1990 | Wetterlin et al. |
| 4,942,544 A | 7/1990 | McIntosh et al. |
| 4,950,477 A | 8/1990 | Schmitt et al. |
| 4,952,402 A | 8/1990 | Sparks et al. |
| 4,971,787 A | 11/1990 | Cherukuri et al. |
| 4,984,158 A | 1/1991 | Hillsman |
| 4,988,683 A | 1/1991 | Corbiere |
| 4,995,385 A | 2/1991 | Valentini et al. |
| 4,999,384 A | 3/1991 | Roberts et al. |
| 5,006,343 A * | 4/1991 | Benson et al. ............... 424/450 |
| 5,011,678 A | 4/1991 | Wang et al. |
| 5,013,557 A | 5/1991 | Tai |
| 5,017,372 A | 5/1991 | Hastings |
| 5,026,566 A | 6/1991 | Roser |
| 5,026,772 A | 6/1991 | Kobayashi et al. |
| 5,032,585 A | 7/1991 | Lichtenberger |
| 5,033,463 A | 7/1991 | Cocozza |
| 5,043,165 A | 8/1991 | Radhakrishnan |
| 5,049,388 A | 9/1991 | Knight et al. |
| 5,049,389 A | 9/1991 | Radhakrishnan |
| 5,069,936 A | 12/1991 | Yen |
| 5,089,181 A | 2/1992 | Hauser |
| 5,098,893 A | 3/1992 | Franks et al. |
| 5,112,596 A | 5/1992 | Malfroy-Camine |
| 5,112,598 A | 5/1992 | Biesalski |
| 5,118,494 A | 6/1992 | Schultz et al. |
| 5,126,123 A | 6/1992 | Johnson |
| 5,145,684 A | 9/1992 | Liversidge |
| 5,149,543 A * | 9/1992 | Cohen et al. ............... 424/499 |
| 5,149,653 A | 9/1992 | Roser |
| 5,160,745 A | 11/1992 | DeLuca et al. |
| 5,173,298 A | 12/1992 | Meadows |
| 5,182,097 A | 1/1993 | Byron et al. |
| 5,190,029 A | 3/1993 | Byron et al. |
| 5,200,399 A | 4/1993 | Wettlaufer et al. |
| 5,202,159 A | 4/1993 | Chen et al. |
| 5,202,333 A | 4/1993 | Berger et al. |
| 5,204,108 A | 4/1993 | Illum |
| 5,208,226 A | 5/1993 | Palmer |
| 5,215,079 A | 6/1993 | Fine et al. |
| 5,225,183 A | 7/1993 | Purewal et al. |
| 5,230,884 A | 7/1993 | Evans et al. |
| 5,239,993 A | 8/1993 | Evans |
| 5,240,712 A | 8/1993 | Smith et al. |
| 5,240,843 A | 8/1993 | Gibson et al. |
| 5,240,846 A | 8/1993 | Collins et al. |
| 5,254,330 A | 10/1993 | Ganderton et al. |
| 5,260,306 A | 11/1993 | Boardman et al. |
| 5,262,405 A | 11/1993 | Girod-Vaquez et al. |
| 5,270,048 A | 12/1993 | Drake |
| 5,284,656 A | 2/1994 | Platz et al. |
| 5,290,765 A | 3/1994 | Wettlaufer |
| 5,299,566 A | 4/1994 | Davis et al. |
| 5,306,483 A | 4/1994 | Mautone |
| 5,306,506 A | 4/1994 | Zema et al. |
| 5,308,620 A | 5/1994 | Yen |
| 5,309,900 A | 5/1994 | Knoch et al. |
| 5,312,335 A | 5/1994 | McKinnon et al. |
| 5,312,909 A | 5/1994 | Driessen et al. |
| 5,342,625 A | 8/1994 | Hauer et al. |
| 5,348,730 A | 9/1994 | Greenleaf et al. |
| 5,348,852 A | 9/1994 | Bonderman |
| 5,354,562 A | 10/1994 | Platz et al. |
| 5,354,934 A | 10/1994 | Pitt et al. |
| 5,366,734 A | 11/1994 | Hutchinson |
| 5,376,359 A | 12/1994 | Johnson |
| 5,380,473 A | 1/1995 | Bogue et al. |
| 5,380,519 A | 1/1995 | Schneider et al. |
| 5,384,345 A | 1/1995 | Naton |
| 5,387,431 A | 2/1995 | Fuisz |
| 5,403,861 A | 4/1995 | Goldin et al. |
| 5,404,871 A | 4/1995 | Goodman et al. |
| 5,422,360 A | 6/1995 | Miyajima et al. |
| 5,422,384 A | 6/1995 | Samuels et al. |
| 5,425,951 A | 6/1995 | Goodrich, Jr. et al. |
| 5,437,272 A | 8/1995 | Fuhrman |
| 5,451,569 A | 9/1995 | Wong et al. |
| 5,453,514 A | 9/1995 | Niigata et al. |
| 5,458,135 A | 10/1995 | Patton et al. |
| 5,470,885 A | 11/1995 | Fuhrman et al. |
| 5,474,759 A | 12/1995 | Fassberg et al. |
| 5,482,927 A | 1/1996 | Maniar et al. |
| 5,490,498 A | 2/1996 | Faithfull et al. |
| 5,492,688 A | 2/1996 | Byron et al. |
| 5,506,203 A | 4/1996 | Backstrom et al. |
| 5,512,547 A | 4/1996 | Johnson et al. |
| 5,518,709 A | 5/1996 | Sutton et al. |
| 5,518,731 A | 5/1996 | Meadows |
| 5,518,998 A | 5/1996 | Backstrom et al. |
| 5,527,521 A | 6/1996 | Unger et al. |
| 5,540,225 A | 7/1996 | Schutt |

| Patent | Date | Inventor |
|---|---|---|
| 5,542,935 A | 8/1996 | Unger et al. |
| 5,547,656 A | 8/1996 | Unger |
| 5,547,696 A | 8/1996 | Sorensen |
| 5,552,160 A | 9/1996 | Liversidge et al. |
| 5,562,608 A | 10/1996 | Sekins et al. |
| 5,567,439 A | 10/1996 | Myers et al. |
| 5,569,448 A | 10/1996 | Wong et al. |
| 5,569,450 A | 10/1996 | Duan et al. |
| 5,571,499 A | 11/1996 | Hafler et al. |
| 5,580,575 A | 12/1996 | Unger et al. |
| 5,580,859 A | 12/1996 | Felgner et al. |
| 5,589,167 A | 12/1996 | Cleland et al. |
| 5,591,453 A | 1/1997 | Ducheyne et al. |
| 5,605,673 A | 2/1997 | Schutt et al. |
| 5,605,674 A | 2/1997 | Purewal et al. |
| 5,607,915 A | 3/1997 | Patton et al. |
| 5,611,344 A | 3/1997 | Bernstein et al. |
| 5,612,053 A | 3/1997 | Baichwal |
| 5,616,311 A | 4/1997 | Yen |
| 5,618,786 A | 4/1997 | Roosdorp et al. |
| 5,621,094 A | 4/1997 | Roser et al. |
| 5,631,225 A | 5/1997 | Sorensen |
| 5,635,159 A | 6/1997 | Fu Lu et al. |
| 5,635,161 A | 6/1997 | Adjei et al. |
| 5,642,728 A | 7/1997 | Andersson et al. |
| 5,648,095 A | 7/1997 | Illum et al. |
| 5,653,961 A | 8/1997 | McNally et al. |
| 5,653,962 A | 8/1997 | Akehurst et al. |
| 5,654,007 A | 8/1997 | Johnson et al. |
| 5,654,278 A | 8/1997 | Sorensen |
| 5,655,521 A | 8/1997 | Faithfull et al. |
| 5,656,297 A | 8/1997 | Bernstein et al. |
| 5,658,549 A | 8/1997 | Akehurst et al. |
| 5,667,808 A | 9/1997 | Johnson et al. |
| 5,667,809 A | 9/1997 | Trevino et al. |
| 5,673,686 A | 10/1997 | Villax et al. |
| 5,674,471 A | 10/1997 | Akehurst et al. |
| 5,674,472 A | 10/1997 | Akehurst et al. |
| 5,674,473 A | 10/1997 | Purewal et al. |
| 5,676,929 A | 10/1997 | Akehurst et al. |
| 5,681,545 A | 10/1997 | Purewal et al. |
| 5,681,746 A | 10/1997 | Bodner et al. |
| 5,683,676 A | 11/1997 | Akehurst et al. |
| 5,683,677 A | 11/1997 | Purewal et al. |
| 5,688,782 A | 11/1997 | Neale et al. |
| 5,690,954 A | 11/1997 | Illum |
| 5,695,743 A | 12/1997 | Purewal et al. |
| 5,695,744 A | 12/1997 | Neale et al. |
| 5,698,537 A | 12/1997 | Pruss |
| 5,705,482 A | 1/1998 | Christensen et al. |
| 5,707,352 A | 1/1998 | Sekins et al. |
| 5,707,644 A | 1/1998 | Illum |
| 5,718,222 A | 2/1998 | Lloyd et al. |
| 5,718,921 A | 2/1998 | Mathiowitz et al. |
| 5,720,940 A | 2/1998 | Purewal et al. |
| 5,724,957 A | 3/1998 | Rubsamen et al. |
| 5,725,841 A | 3/1998 | Duan et al. |
| 5,725,871 A | 3/1998 | Illum |
| 5,728,574 A | 3/1998 | Legg |
| 5,733,555 A | 3/1998 | Chu |
| 5,735,263 A | 4/1998 | Rubsamen et al. |
| 5,736,124 A | 4/1998 | Akehurst et al. |
| 5,741,478 A | 4/1998 | Osborne et al. |
| 5,741,522 A | 4/1998 | Violante et al. |
| 5,743,250 A | 4/1998 | Gonda et al. |
| 5,743,252 A | 4/1998 | Rubsamen et al. |
| 5,744,123 A | 4/1998 | Akehurst et al. |
| 5,744,166 A | 4/1998 | Illum |
| 5,747,001 A | 5/1998 | Wiedmann et al. |
| 5,747,445 A | 5/1998 | Backstrom et al. |
| 5,755,218 A | 5/1998 | Johansson et al. |
| 5,756,104 A | 5/1998 | de Haan et al. |
| 5,766,520 A | 6/1998 | Bronshtein |
| 5,766,573 A | 6/1998 | Purewal et al. |
| 5,770,187 A | 6/1998 | Hasebe et al. |
| 5,770,222 A | 6/1998 | Unger et al. |
| 5,770,559 A | 6/1998 | Manning et al. |
| 5,770,585 A | 6/1998 | Kaufman et al. |
| 5,775,320 A | 7/1998 | Patton et al. |
| 5,776,496 A | 7/1998 | Violante et al. |
| 5,780,014 A | 7/1998 | Eljamal et al. |
| 5,780,295 A | 7/1998 | Livesey et al. |
| 5,804,212 A | 9/1998 | Illum |
| 5,811,406 A | 9/1998 | Szoka, Jr. et al. |
| 5,814,607 A | 9/1998 | Patton |
| 5,817,293 A | 10/1998 | Akehurst et al. |
| 5,820,883 A | 10/1998 | Tice et al. |
| 5,829,435 A | 11/1998 | Rubsamen et al. |
| 5,830,430 A | 11/1998 | Unger et al. |
| 5,830,853 A | 11/1998 | Backstrom et al. |
| 5,849,700 A | 12/1998 | Sorensen et al. |
| 5,851,453 A | 12/1998 | Hanna et al. |
| 5,853,698 A | 12/1998 | Straub et al. |
| 5,853,752 A | 12/1998 | Unger et al. |
| 5,853,763 A | 12/1998 | Tice et al. |
| 5,855,913 A | 1/1999 | Hanes et al. |
| 5,856,367 A | 1/1999 | Barrows et al. |
| 5,858,784 A | 1/1999 | Debs et al. |
| 5,863,554 A | 1/1999 | Illum |
| 5,874,063 A | 2/1999 | Briggner et al. |
| 5,874,064 A | 2/1999 | Edwards et al. |
| 5,891,844 A | 4/1999 | Hafner |
| 5,891,873 A | 4/1999 | Colaco et al. |
| 5,898,028 A | 4/1999 | Jensen et al. |
| 5,921,447 A | 7/1999 | Barger et al. |
| 5,925,334 A | 7/1999 | Rubin et al. |
| 5,928,469 A | 7/1999 | Franks et al. |
| 5,948,411 A | 9/1999 | Koyama et al. |
| 5,955,143 A | 9/1999 | Wheatley |
| 5,955,448 A | 9/1999 | Colaco et al. |
| 5,972,366 A | 10/1999 | Haynes et al. |
| 5,976,436 A | 11/1999 | Livesley et al. |
| 5,985,309 A | 11/1999 | Edwards et al. |
| 5,993,783 A | 11/1999 | Eljamal et al. |
| 5,993,805 A | 11/1999 | Sutton et al. |
| 5,994,314 A | 11/1999 | Eljamal et al. |
| 5,994,318 A | 11/1999 | Gould-Fogerite et al. |
| 5,997,848 A | 12/1999 | Patton |
| 6,013,638 A | 1/2000 | Crystal et al. |
| 6,017,310 A | 1/2000 | Johnson et al. |
| 6,019,968 A | 2/2000 | Platz et al. |
| 6,034,080 A | 3/2000 | Colaco et al. |
| 6,041,777 A | 3/2000 | Faithful et al. |
| 6,048,546 A | 4/2000 | Sasaki et al. |
| 6,051,256 A | 4/2000 | Platz et al. |
| 6,051,259 A | 4/2000 | Johnson et al. |
| 6,060,069 A | 5/2000 | Hill et al. |
| 6,068,600 A | 5/2000 | Johnson et al. |
| 6,071,428 A | 6/2000 | Franks et al. |
| 6,077,543 A | 6/2000 | Gordon et al. |
| 6,086,376 A | 7/2000 | Moussa et al. |
| 6,113,948 A | 9/2000 | Heath et al. |
| 6,116,237 A | 9/2000 | Schultz et al. |
| 6,120,751 A * | 9/2000 | Unger ................... 424/9.51 |
| 6,123,924 A | 9/2000 | Mistry et al. |
| 6,123,936 A | 9/2000 | Platz et al. |
| 6,129,934 A | 10/2000 | Egan et al. |
| 6,136,295 A | 10/2000 | Edwards et al. |
| 6,136,346 A | 10/2000 | Eljamal et al. |
| 6,138,668 A | 10/2000 | Patton et al. |
| 6,139,819 A | 10/2000 | Unger et al. |
| 6,142,216 A | 11/2000 | Lannes |
| 6,165,463 A | 12/2000 | Platz et al. |
| 6,165,508 A | 12/2000 | Tracy et al. |
| RE37,053 E | 2/2001 | Hanes et al. |
| 6,187,344 B1 | 2/2001 | Eljamal et al. |
| 6,190,859 B1 | 2/2001 | Putnak et al. |
| 6,207,135 B1 | 3/2001 | Rossling et al. |
| 6,231,851 B1 | 5/2001 | Platz et al. |
| 6,248,720 B1 * | 6/2001 | Mathiowitz et al. ........... 514/44 |
| 6,254,854 B1 | 7/2001 | Edwards et al. |
| 6,258,341 B1 | 7/2001 | Foster et al. |
| 6,284,282 B1 | 9/2001 | Maa et al. |
| 6,290,991 B1 | 9/2001 | Roser et al. |
| 6,303,581 B2 | 10/2001 | Pearlman |
| 6,303,582 B1 | 10/2001 | Eljamal et al. |
| 6,309,623 B1 | 10/2001 | Weers et al. |
| 6,309,671 B1 | 10/2001 | Foster et al. |

| | | | | | |
|---|---|---|---|---|---|
| 6,313,102 B1 | 11/2001 | Colaco et al. | EP | 0520748 | 10/1992 |
| 6,331,310 B1 | 12/2001 | Roser et al. | EP | 0372777 | 1/1993 |
| 6,344,182 B1 | 2/2002 | Sutton et al. | EP | 0391896 | 3/1994 |
| 6,358,530 B1 | 3/2002 | Eljamal et al. | EP | 0536204 | 4/1994 |
| 6,365,190 B1 | 4/2002 | Gordon et al. | EP | 0600730 | 8/1994 |
| 6,372,258 B1 | 4/2002 | Platz et al. | EP | 0611567 | 8/1994 |
| 6,416,739 B1 | 7/2002 | Rogerson et al. | EP | 0611567 A1 | 8/1994 |
| 6,423,334 B1 | 7/2002 | Brayden et al. | EP | 0616524 | 9/1994 |
| 6,423,344 B1 | 7/2002 | Platz et al. | EP | 0553298 | 11/1994 |
| 6,426,210 B1 | 7/2002 | Franks et al. | EP | 0653205 | 5/1995 |
| 6,433,040 B1 | 8/2002 | Dellamary et al. | EP | 0655237 | 5/1995 |
| 6,468,782 B1 | 10/2002 | Tunnacliffe et al. | EP | 0656206 | 6/1995 |
| 6,479,049 B1 | 11/2002 | Platz et al. | EP | 0658101 | 6/1995 |
| 6,503,411 B1 | 1/2003 | Franks et al. | EP | 0513127 | 7/1995 |
| 6,503,480 B1 | 1/2003 | Edwards et al. | EP | 0493437 | 8/1995 |
| 6,509,006 B1 | 1/2003 | Platz et al. | EP | 0556256 | 8/1995 |
| 6,514,496 B1 | 2/2003 | Platz et al. | EP | 0616525 | 9/1995 |
| 6,518,239 B1 | 2/2003 | Kuo et al. | EP | 0499344 | 10/1995 |
| 6,565,871 B2 | 5/2003 | Kampinga et al. | EP | 0587790 | 1/1996 |
| 6,565,885 B1 | 5/2003 | Tarara et al. | EP | 0605578 | 1/1996 |
| 6,569,406 B2 | 5/2003 | Stevenson et al. | EP | 0588897 | 2/1996 |
| 6,569,458 B1 | 5/2003 | Gombotz et al. | EP | 0714905 | 6/1996 |
| 6,572,893 B2 | 6/2003 | Gordon et al. | EP | 0536235 | 1/1997 |
| 6,582,728 B1 | 6/2003 | Platz et al. | EP | 0257956 | 3/1998 |
| 6,586,006 B2 | 7/2003 | Duffy et al. | EP | 0539522 | 12/1998 |
| 6,589,560 B2 | 7/2003 | Foster et al. | ES | 84-03520 | 6/1984 |
| 6,592,904 B2 | 7/2003 | Platz et al. | FR | 2238476 | 2/1975 |
| 6,630,169 B1 | 10/2003 | Bot et al. | GB | 1288094 | 9/1972 |
| 6,649,911 B2 | 11/2003 | Kawato | GB | 1381588 | 1/1975 |
| 6,652,837 B1 | 11/2003 | Edwards et al. | GB | 1477775 | 6/1977 |
| 6,655,379 B2 | 12/2003 | Clark et al. | GB | 1533012 | 11/1978 |
| 6,673,335 B1 | 1/2004 | Platz et al. | GB | 2065659 | 7/1981 |
| 6,681,767 B1 | 1/2004 | Patton et al. | GB | 2126588 | 3/1984 |
| 6,685,967 B1 | 2/2004 | Patton et al. | GB | 2187191 | 1/1987 |
| 6,737,045 B2 | 5/2004 | Patton et al. | GB | 21878191 | 1/1987 |
| 6,737,066 B1 | 5/2004 | Moss | GB | 206569 | 7/1991 |
| 6,752,893 B2 | 6/2004 | Frieder | JP | 52-139789 | 11/1977 |
| 6,797,258 B2 | 9/2004 | Platz et al. | JP | 58-216695 | 12/1983 |
| 6,811,792 B2 | 11/2004 | Roser et al. | JP | 59-095885 | 6/1984 |
| 6,825,031 B2 | 11/2004 | Franks et al. | JP | 60-244288 | 12/1985 |
| 6,893,657 B2 | 5/2005 | Roser et al. | JP | 62-228272 | 10/1987 |
| 6,921,527 B2 | 7/2005 | Platz et al. | JP | 62-255434 | 11/1987 |
| 2002/0052310 A1 | 5/2002 | Edwards et al. | JP | 03038592 | 2/1991 |
| 2002/0127188 A1 | 9/2002 | Platz et al. | JP | 06-100464 | 4/1994 |
| 2002/0132787 A1 | 9/2002 | Eljamal et al. | SE | 84-03520 | 6/1984 |
| 2002/0192164 A1 | 12/2002 | Patton et al. | WO | 86/04095 | 7/1986 |

FOREIGN PATENT DOCUMENTS

| | | | | | |
|---|---|---|---|---|---|
| AU | 714990 | 1/2000 | WO | 87/00196 | 1/1987 |
| BE | 902257 | 8/1985 | WO | 87/02038 | 4/1987 |
| DE | 161072 | 10/1904 | WO | 87/05300 | 9/1987 |
| DE | 471490 | 8/1931 | WO | 88/08/298 | 11/1988 |
| DE | 1080265 | 4/1960 | WO | 89/06976 | 8/1989 |
| DE | 3141498 | 4/1983 | WO | 90/05182 | 5/1990 |
| EP | 0282179 | 9/1888 | WO | 90/11756 | 10/1990 |
| EP | 0015123 | 3/1980 | WO | 90/15635 | 12/1990 |
| EP | 0072046 | 2/1983 | WO | 91/04715 | 4/1991 |
| EP | 0090356 | 10/1983 | WO | WO 91/04011 | 4/1991 |
| EP | 0111216 | 6/1984 | WO | 91/06282 | 5/1991 |
| EP | 0136030 | 4/1985 | WO | WO 91/11173 | 8/1991 |
| EP | 0139286 | 5/1985 | WO | WO 91/12823 | 9/1991 |
| EP | 0140489 | 5/1985 | WO | 91/16038 | 10/1991 |
| EP | 0222313 | 5/1987 | WO | WO 91/16444 | 10/1991 |
| EP | 0229810 | 7/1987 | WO | 91/16882 | 11/1991 |
| EP | 0274431 | 7/1988 | WO | 91/18091 | 11/1991 |
| EP | 0274431 A2 | 7/1988 | WO | WO 91/16882 | 11/1991 |
| EP | 0325936 | 8/1989 | WO | WO 92/00107 | 1/1992 |
| EP | 0356154 | 2/1990 | WO | 92/02133 | 2/1992 |
| EP | 0360340 | 3/1990 | WO | WO 92/11050 | 7/1992 |
| EP | 0366303 | 5/1990 | WO | WO 92/14444 | 9/1992 |
| EP | 0372777 | 6/1990 | WO | WO 92/18164 | 10/1992 |
| EP | 0372777 A2 | 6/1990 | WO | 92/19243 | 11/1992 |
| EP | 0383569 | 8/1990 | WO | 93/00951 | 1/1993 |
| EP | 0415567 | 3/1991 | WO | 93/02834 | 2/1993 |
| EP | 0430045 | 6/1991 | WO | 93/09832 | 5/1993 |
| EP | 0433679 | 6/1991 | WO | 93/10758 | 6/1993 |
| EP | 2036844 | 8/1991 | WO | 93/11746 | 6/1993 |
| EP | 0463653 | 1/1992 | WO | 93/12240 | 6/1993 |
| EP | 0474874 | 3/1992 | WO | WO 93/11744 | 6/1993 |
| | | | WO | WO 93/11745 | 6/1993 |
| | | | WO | 93/13752 | 7/1993 |

| | | |
|---|---|---|
| WO | WO 93/14172 | 7/1993 |
| WO | 93/17663 | 9/1993 |
| WO | 93/23065 | 11/1993 |
| WO | 93/23110 | 11/1993 |
| WO | 94/04133 * | 3/1994 |
| WO | 94/07514 | 4/1994 |
| WO | 94/08552 | 4/1994 |
| WO | WO 94/08627 | 4/1994 |
| WO | 94/13271 | 6/1994 |
| WO | 94/22423 | 10/1994 |
| WO | 94/24263 | 10/1994 |
| WO | 95/00127 | 1/1995 |
| WO | 95/01324 | 1/1995 |
| WO | WO 95/00128 | 1/1995 |
| WO | WO 95/05194 | 2/1995 |
| WO | 95/06126 | 3/1995 |
| WO | WO 95/15118 | 6/1995 |
| WO | WO 95/17195 | 6/1995 |
| WO | 95/20979 | 8/1995 |
| WO | 95/24183 | 9/1995 |
| WO | WO 95/23613 | 9/1995 |
| WO | WO 95/24892 | 9/1995 |
| WO | WO 95/27476 | 10/1995 |
| WO | 95/31479 | 11/1995 |
| WO | WO 95/28944 | 11/1995 |
| WO | WO 95/31182 | 11/1995 |
| WO | WO 95/31964 | 11/1995 |
| WO | 95/33488 | 12/1995 |
| WO | 96/03978 | 2/1996 |
| WO | 96/09085 | 3/1996 |
| WO | WO 96/37399 | 3/1996 |
| WO | WO 96/09814 | 4/1996 |
| WO | WO 96/15814 | 5/1996 |
| WO | 96/11745 | 6/1996 |
| WO | 9619198 | 6/1996 |
| WO | WO 96/18388 | 6/1996 |
| WO | WO 96/19197 | 6/1996 |
| WO | WO 96/19198 | 6/1996 |
| WO | WO 96/19199 | 6/1996 |
| WO | WO 96/19968 | 7/1996 |
| WO | 96/27393 | 9/1996 |
| WO | WO 96/26746 | 9/1996 |
| WO | 96/32096 | 10/1996 |
| WO | WO 96/32149 | 10/1996 |
| WO | 96/40049 | 12/1996 |
| WO | 96/40077 | 12/1996 |
| WO | WO 96/40068 | 12/1996 |
| WO | WO 96/40277 | 12/1996 |
| WO | WO 97/03649 | 2/1997 |
| WO | WO 97/26863 * | 7/1997 |
| WO | 97/34689 | 9/1997 |
| WO | 9736574 | 10/1997 |
| WO | 9736578 | 10/1997 |
| WO | WO 97/35562 | 10/1997 |
| WO | WO 97/36574 | 10/1997 |
| WO | WO 97/36578 | 10/1997 |
| WO | 9744012 | 11/1997 |
| WO | WO 97/40819 | 11/1997 |
| WO | WO 97/41833 | 11/1997 |
| WO | WO 97/44012 | 11/1997 |
| WO | WO 97/44013 | 11/1997 |
| WO | WO 98/00111 | 1/1998 |
| WO | WO 98/01161 | 1/1998 |
| WO | WO 98/05302 | 2/1998 |
| WO | WO 98/07414 | 2/1998 |
| WO | WO 98/08519 | 3/1998 |
| WO | WO 98/13031 | 4/1998 |
| WO | WO 98/16205 | 4/1998 |
| WO | WO 98/17257 | 4/1998 |
| WO | 98/24882 | 6/1998 |
| WO | WO 98/29097 | 7/1998 |
| WO | WO 98/29098 | 7/1998 |
| WO | WO 98/29099 | 7/1998 |
| WO | WO 98/29140 | 7/1998 |
| WO | WO 98/30207 | 7/1998 |
| WO | WO 98/31346 | 7/1998 |
| WO | WO 98/31348 | 7/1998 |
| WO | WO 98/33480 | 8/1998 |
| WO | WO 98/33487 | 8/1998 |
| WO | WO 98/41188 | 9/1998 |
| WO | 98/58989 | 12/1998 |
| WO | WO 99/06026 | 2/1999 |
| WO | 9916419 | 4/1999 |
| WO | 9916420 | 4/1999 |
| WO | 9916421 | 4/1999 |
| WO | 9916422 | 4/1999 |
| WO | 99/32098 | 7/1999 |
| WO | WO 99/32083 | 7/1999 |
| WO | 99/38493 | 8/1999 |
| WO | 99/66903 | 12/1999 |
| WO | 0000176 | 1/2000 |
| WO | 00/10541 | 3/2000 |
| WO | 00/21594 | 4/2000 |
| WO | 0000215 | 6/2000 |
| WO | 00/72904 | 12/2000 |
| WO | 01/00263 | 1/2001 |
| WO | 0113092 | 3/2001 |
| WO | 01/87278 | 11/2001 |
| WO | 01/95874 | 12/2001 |

OTHER PUBLICATIONS

Papahadjopoulos et al (Cochleate lipid cylinders: Formation by fusion of unilamellar lipid vesicles, Biochimica et Biophysics, 394 (1975), 483-491).*

Coacervate-Wilkipedia.*

C. Roth et al., "Production of Hollow Spheres," Pargamon Press, vol. 19 (No. 7), p. 939-942, 1988.

Dellamary et al. "Hollow Porous Particles in Metered Dose Inhalers" Pharm Research 17(2): 168-174 (2000).

Ahlneck et al. "The Molecular Basis of Moisture Effects on the Physical and Chemical Stability of Drugs in the Solid State" Int. J. of Pharmaceuticals 62: 87-95 (1990).

Altenbach et al., "$Ca^{2a}$ Binding to Phosphatidycholine Bilayers as Studied by Deuterium Magnetic Resonance. Evidence for the Formation of a $Ca^{2a}$ Complex with Two Phospholipid Molecules" Biochemistry 23: 3913-3920 (1984).

Babincova et al. "Dextran Enhances Calcium-Induced Aggregation of Phosphatidyserine Liposomes: Possible Implications for Exocytosis" Physiol Res 48(4): 319-321 (1999).

Bucktoss et al. "The Use of Gravimetric Studies to Assess the Degree of Crystallinity of Predominantly Crystalline Powders" Int. J. of Pharmaceutics 123: 265-271 (1995).

Buldt et al. "Neutron Diffraction Studies pn Phosphatidylcholine Model Membranes" J. Mol. Biol. 134: 673-691 (1979).

Cevc, G. "Membrane Electrostatics" Biochim Biophys Acta 1031(3): 311-382 (1990)., in particular pp. 330-338.

Duzgunes et al. "Studies on the Mechanism of Membrane Fusion. Role of Head-Group Composition in Calcium- and Magnesium-Induced Fusion of Mixed Phospholipid Vesicles" Biochim Biophys Acta 642: 182-195 (1981).

Ebara et al. "Interactions of Calcium Ions with Phospholipid Membranes" Langmuir 10: 2267-2271 (Apr. 1994).

Eizenberg et al. "Adsorption of Monovalent Cations to Bilayer Membranes Containing Negative Phospholipids" Biochemistry 18(23): 5213-5223 (1979).

Goldbach et al. "Spray-Drying of Liposomes for a Pulmonary Administration I. Chemical Stability of Phospholipids" Drug Develop Ind Pharm 19(19): 2611-2622 (1993).

Gordon et al. "Ideal Copolymers and the Second-Order Transitions of Synthetic Rubbers. I. Non-Crystalline Copolymers" J. Appl. Chem. 2: 493-500 (Sep. 1952).

Hancock et al. "Characteristics and Significance of the Amorphous State in Pharmaceutical Systems" J. of Pharmaceutical Sciences 36(1): 1-12 (Jan. 1997).

Hancock et al. The Relationship Between the Glass Transition Temperature and the Water Content Amorphous Pharmaceutical Solid. Pharm Research 11(4): 471-477 (1994).

Hauser et al. "Comparative Structural Aspects of Cation Binding to Phosphatidylserine Bilayers" Biochim Biophys Acta 813: 343-346 (1985).

Hauser et al. "Interactions of Divalent Cations with Phosphatidylserine Bilayer Membranes" Biochemistry 23: 34-41 (1984).

Huster et al. "Investigation of Phospholipid Area Compression Induced by Calcium-Mediated Dextran Sulfate Interaction" Biophys J. 77(2): 879-887 (Aug. 1999).
Huster et al. "Strength of Ca(2+) Binding to Retinal Lipid Membranes: Consequences for Lipid Organization" Biophys J. 78(6): 3011-3018 (Jun. 2000).
Jacobson et al. "Phase Transitions and Phase Separations in Phospholipid Membranes Induced by Changes in Temperature, pH. and Concentration of Bivalent Cations" Biochemistry 14(1): 152-161 (1975).
Kwon et al. "Calcium Ion Adsorption on Phospholipid Bilayers—Theoretical Interpretation" J Jap Oil Chem Soc 43(1): 23-30 (1994).
Lis et al. "Adsorption of Divalent Cations to a Variety of Phosphatidylcholine Bilayers" Biochemistry 20: 1771-1777 (1981).
Lis et al. "Binding of Divalent Cations to Dipalmitoylphosphatidylcholine Bilayers and Its Effect on Bilayer Interactions" Biochemistry 20: 1761-1770 (1981).
Millqvist-Fureby et al. "Surface Characterisation of Freeze-Dried Protein/Carbohydrate Mixtures" Int. J. Pharm. 191: 103-114 (1999).
1. Joachim Seelig, *Handb. Met.—Ligand Interact. Biol. Fluids: Bioinorg. Chem.* & Metal Ion Interactions with Lipids: 698-706 (1995).
Shah et al. "The Ionic Structure of Sphingomyelin Monolayers" Biochim Biophys Acta 135: 184-187 (1967).
Shavnin et al. "Cholesterol Affects Divalent Cation-Induced Fusion and Isothermal Phase Transitions of Phospholipid Membranes" Biochim Biophys Acta 946:405-416 (1988).
Simba et al. "On a General Relation Involving the Glass Temperature and Coefficients of Expansion of Polymers" J. Chem. Physics 37(5): 1003-1007 (Sep. 1962).
Sugisaki et al. "Calorimetric Study of the Glassy State. IV. Heat Capacities of Glassy Water and Cubic Ice" Bulletin of the Chemical Society of Japan 41: 2591-2599 (Nov. 1968).
Tatulian. S.A. "Evalutation of Divalent Cation Binding to Phosphatidylserine Membranes by an Analysis of Concentration Dependence Surface Potential" J. Colloid Interface Science 175: 131-137 (1995).
Verstraaten et al. "Effects of Al(3+) and Related Metals on Membrane Phase State and Hydration: Correlation with Lipid Oxidation" Arch Biochem Biophys 375(2): 340-346 (Mar. 15, 2000).
Whipps at al. "Growth of Calcium Monohydrate at Phospholipid Langmuir Monolayers" J Cryst Growth 192: 243.249 (1998).
Yamaguchi at al. "Adsorption of Divalent Cations onto the Membrane Surface of Lipid Emulsion" Colloids and Surfaces B: Biolaterfaces 5: 49-55 (1995).
Zaril, et al. (1999) Amphotericin B cochioates as a novel oral delivery system for the treatment of fungal infections. Proceedings of the International Symposium on Controlled Release Bioactive Materials. pp. 964-965, XP-002145322.
Courtesy PCT International Search Report dated Feb. 28, 2002 in 3 pages.
Belopol'skaya, T.V., et al., The Effect of Water as Natural Plasticizer on Thermal Properties of Denaturated DNA Studied by Calorimetry 4 Vestnik Sankt-petersburgskogo Universiteta Seriya, pp. 16-22, abstract only, 2 pgs. (1999).
Ben-Jenria, Abdellaziz, et al., "Large Powous Particles for Sustained Protection from Carbochol-Induced Bronchoconstriction in Guinea Pigs", *Pharma. Res.*, vol. 16, No. 4, p. 555-561.
Bigsbee, et al. "Solid State Liability of Insulin: Comparison of Crystalline and Amorphous Forms", *Pharmaceutical Research* 10(10): Abstract No. PDD 7418, p. S-279 (1993).
Blakeley, et al., "Dry instant blood typing for bedside use", *Lancet*, 336: 854-855 (1990).
Bootsma, H.P.R., et al., "β-Cyclodestrin as an Excipient in Solid Oral Dosage Forms: In Vitro and In Vivo Evaluation of Spray-Dried Diazepan-β-Cyclodestrin Products", *International Journal of Pharmaceutics* 51:213-223 (1989).
Borgstrom, et al., "Lung Deposition of Budesonide Inhaled via Turbuhaler", *Eur. Respir. J.*, p. 69-73 (Feb. 26, 1994).
Branchu, S., et al., "The Effect of Cyclodestrins on Monomeric Protein Unfolding", *Biocalorimetry: Applications of Calorimetry in the Biological Sciences*, J.E. Ladbury and B.Z. Chowdhry (eds.), John Wiley & Sons, Ltd., 297-301 (1998).

Branchu, S., et al., "Hydroxypropyl-β-Cyclodextrin Inhibits Spray-Drying-Induced Inactivation of β-Galactosidase", *Journal of Pharmaceutical Sciences* 88(9): 905-911 (1999).
Brange, et al., "Chemical Stability of Insulin. I. Hydrolytic Degradation During Storage of Pharmaceutical Preparations", *Pharmaceutical Research* 9(6): 715-726 (1992).
Broadhead, J., et al., The Effect of Process and Formulation Variable on the Properties of Spray-Drive β-Galactosidase, *J. Pharm. Pharmacol.* 46(6): 458-567 (Jun. 1994).
Broadhead, J., et al., *The Spray Drying of Pharmaceuticals*, 18 Drug Development and Industrial Pharmacy, p. 1169-1206 (1992).
Brown, "A Therapeutic Panorama of the Spongiform Encephalopathies", *Antiviral Chem. Chemother.* 1(2): 75-83 (1990).
Buitink, Julia, et al., *High Critical Temperature above Tg May Contribute to the Stability of Biological Systems*, 79 Biophysical Journal, 1119-1128 (Aug. 2000).
Burvall, et al., "Storage of Lactose-Hydrolised Dried Milk: Effect of Water Activity on the Protein Nutritional Value", *Journal of Dairy Research* 45: 381-389 (1978).
Byron, Peter R., et al., *Drug Carrier Selection—Important Physicochemical Characteristics* Respiratory Drug Delivery, 5$^{th}$ Ed., Interpharm Press., 103-113 (1996).
Byström, et al., "Microcalorimetry—A Novel Technique for Characterization of Powders", *Respiratory Drug Delivery IV*, p. 297-302 (1994).
Eleutherio, et al., "Role of the Trehalose Carrier in Dehydration Resistence of *Saccharomyces cerevisiae*", *Biochimica et Biophysica Acta*, 1156: 263-266 (1993).
Fahy, et al., "Vitrification as an Approach to Cryopreservation", *Cryobiology*, 21: 407-426 (1984).
Finar, I.L., "§14. Trehalose, m.p. 203°C", under "Carbohydrate" Organic Chemistry, vol. 2, Stereochemistry and the Chemistry of Natural Products, 5$^{th}$ edition, Longman, p. 323 (1996).
Forbes, R.T., et al., "Water Vapor Sorption Studies on the Physical Stability of a Series of Spray-Dried Protein/Sugar Powders for Inhalation", *Journal of Pharmaceutical Sciences*, 87(11): 1316-1321 (1998).
Franks, "Freeze Drying: From Empiricism to Predictability", *Cyro-Letters*, 11: 93-110 (1990).
Franks, "Materials Science and the Production of Shelf-Stable Biologicals", *Pharmaceutical Technological International*, 24: 24-34 (Oct. 1991).
Franks, "Separation, Improved Freeze-Drying, an Analysis of the Basic Scientific Principles", *Process Biochemistry*, 24(1): iii-vii (1989).
Franks, "Accelerated Stability Testing of Bioproducts: Attractions and Pitfalls", *TIBTECH*, 12: 114-117 (1994).
French, Donna L., et al., "The Influence of Formulation on Emission, Deaggregation and Deposition of Dry Powders for Inhalation," *J. Aerosol Science*, vol. 27, No. 5, pp. 769-783 (1996).
"Chapter 89—Oral Solid Dosage Forms," In *Remington's Pharmaceutical Sciences*, 18$^{th}$ Edition, Mack Publishing Co., Gennaro, A.R., pp. 1646-1647.
Gonda, et al., "Characterization of Hygroscopic Inhalation Aerosols", In: Particle Size Analysis, (Eds. N.G. Stanley-Wood and T. Allen, Wiley Heyden Ltd., NY), pp. 31-43 (1981).
Green, et al., "The Protein-Glass Analogy: Some Insights from Homopeptide omparisons", *J. Phys. Chem.*, 98: 13780-13790 (Apr. 1994).
Green, et al., "Phase Relations and Vitrification in Saccharide-Water Solutions and the Anomaly", *J. Phys. Chem.*, 93: 2880-2882 (1989).
Hahn, et al., "Solid Surfactant Solutions of Active Ingredients in Sugar Esters", *Pharmaceutical Research*, 6: 958-959 (1989).
Hancock, et al., "The Use of Solution Theories for Predicting Water Vapor Absorption by Amorphous Pharmaceutical Solids: A Test of the Flory-Huggins and Vrentas Models", *Pharmaceutical Research*, 10(9): 1262-1267 (1993).
Hancock, et al., "Molecular Mobility of Amorphous Pharmaceutical Solids Below Their Glass Transition Temperatures", *Pharmaceutical Research*, 12(6): 799-806 (1995).
Hancock, B.C., et al., "The Effect of Temperature on Water Vapor Sorption by Some Amorphous Pharmaceutical Sugars", *Pharmaceutical Development and Technology*, 4(1): 125-131 (1999).

Hancock, B.C., et al., "The Relationship Between the Glass Transition Temperature and Water Content of Amorphous Pharmaceutical Solids", *Pharmaceutical Research*, 11(4): 471-477 (1994).

Hancock, et al., "A Pragmatic Test of Simple Calorimetric Method for Determining the Fragility of some Amorphous Pharmaceutical Materials", *Pharm. Res.*, 15(5): 762-767 (1998).

Hanes, et al., "Porous Dry-Powder PLGA Microspheres coated with Lung Surfactant for Systematic Insulin Delivery via the Lung", *Proc. Int'l. Symp. Control Rel. Bioactive Matter*, 24: 57-58 (1997).

Harwood, C.F., "Compaction Effect on Flow Property Indexes for Powders", *J. Pharm. Sci.*, 60:161-163 (1971).

Hatley, R.H.M., et al., "Stabilization of Labile Materials by Amorphous Carbohydrates Glass Fragility and the Physiochemcial Properties that make Trehalose a Superior Excipient", *Pharmaceutical Research*, 13(9 Suppl.) PDD 7165: S274 (1996).

"Pfizer and Inhale Therapeutic Systems Enter Pulmonary Insulin Collaboration for Dry Powder Aerosol Delivery", Health News Daily, vol. 7, No. 13, pp. 4-5 (Jan. 1995).

Heitefuss, R., et al., "The Stabilization of Extracts of Cabbage Leaf Proteins by Polyhydroxy Compounds for Electrophoretic and Immunological Studies", Archives of Biochemistry and Biophysics, 85: 200-208 (1959).

Heller, Martin C., et al., *Protein Formulation and Lypophilization Cycle Design: Prevention of Damage Due to Freeze-Concentration Induced Phase Separation* 63 Biotechnology & Bioengineeting, 166-174 (1999).

Herrington, T.M., et al., "Physico-Chemical Studies on Sugar Glasses. I. Rates of Crystallization", *Journal of Food Technology*, 19: 409-425 (1984).

Hickey, A. J. et al., "Behavoir of Hygroscopic Pharmaceutical Aerosols and the Influence of Hydrophobic Additives," *Pharmaceutical Research* 10(1):1-7 (1993).

Hoener, Betty-Ann et al., "Factors Influencing Drug Absorption and Availability" *Modern Pharmaceutics*, Gilber S. Banker et al., eds., Marcel Dekker Inc., Chapter 4, pp. 121-153 (1996).

Ibrahim, A. L. et al., "Sprah Vaccination With an Improved F Newcastle Disease Vaccine. A Comparison of Efficacy With the B1 and La Sota Vaccines," *Br. Vet. J.* 139:213-219 (1983).

Igaki, N. et al., "The Inhibition of the Maillard Reaction by L Lysine In-Vitro," *J. Jpn. Diabetes Soc.* 34(5):403-407 (1991) including English abstract.

Iglesias et al., "Adsorption Isotherm of Amorphous Trehalos", *J. Sci. food Agric.* 75:183-186 (1997).

Jameel, F. et al., "Freeze Drying Properties of Some Oligonucleotides", *Pharmaceutical Development and Technology* 6(2):151-157 (2001).

Mutterlein, et al., "New Technology for Generating Inhalation Aerosols—Preliminary Results with the Piezoelectrical Pocket-Inhaler", *J. Aerosol Med.*, 1: 231 (1988).

Nebel, G. J. et al., "Direct Gene Transfer With DNA-Liposome Complexes in Melanoma," Proc. Nat. Acad. Sci. 90:11307-11311.

Nabel, G. J. et al., "Immunotherapy of Malignancy by in Vivo Gene Transfer Into Tumors," *Hum. Gene. Ther.* 3(4): 3 99-4 10 (Aug. 1992) Abstract only [on-line] [retrieved 112/21/04] Retrieved from the Internet < URL: http://www.ncbi.nlm.nih.gov/entrez/query.fcgi?cmd=Retrieve&db=pubmed&dopt=Abstr>.

Naini, V. et al., "Particles for Inhalation Produced by Spray Drying and Electrostatic Precipitation of Different Protein-Sugar Solutions", *Respiratory Drug Delivery V*, pp. 382-384 (1996).

Naini, V. et al., "Physicochemical Stability of Crystalline Sugars and Their Spray-Dried Forms: Dependence Upon Relative Humidity and Suitability for Use in Powder Inhalers", *Drug Development and Industrial Pharmacy* 24(10):895-909 (1998).

Niven, R. W., "Delivery of Biotherapeutics by Inhalation Aerosol," *Critical Reviews in Therapeutic Drug Carrier Systems*, 12(2&3):151-231 (1995).

Niven, R. W., "Delivery of Biotherapeutics by Inhalation Aerosols," *Pharmaceutical Technology* 72-75, 80 (Jul. 1993).

Norberg, J. et al., "Glass Transition in DNA From Molecular Dynamics Simulation", *Proc. Natl. Acad. Sci. USA* 93:10173-10176 (1996).

Notter, R.H., "Physical Chemistry and Physiological Activity of Pulmonary Surfactants", In: Surfactant Replacement Therapy (Eds. Shapiro and Notter, Alan R. Liss, Inc., New York), Chapter 2, pp. 19-71 (1989).

Oksanen et al., "The Relationship between the Glass Transition Temperature and Water Vapor Absorption by Poly(Vinylpyrrolidone)," *Pharmaceutical Research* 7(6): 654-657 and errata on p. 974(1990).

Okumura, K. et al., "Intratracheal Delivery of Calcitonin Dry Powder in Rats and Human Volunteers," *S.T.P. Pharmaceutical Sciences* 4(I):5 pages (Jan., Feb. 1994).

Onodera et al., "Glass Transition of Dehydrated Amorphous Solid", *Bull. Chem. Soc. Japan* 41(9):222 (1968).

Palmer, K.J., et al., "X-Ray Diffractometer and Microscopic Investigation of Crystallization of Amorphous Sucrose", *Agricultural and Food Chemistry* 4(1): 77-81 (Jan. 1956).

Parks, "Studies on Glass. II The Transition Between the Glassy and Liquid States in the Case of Glucose", *Journal of Physical Chemistry* 1366-1379 (1928).

Pearlman et al., "Formulation Strategies for Recombinant Proteins: Human Growth Hormone and Tissue Plasminogen Activator", *Therapeutic Peptides and Proteins, Formulation, Delivery and Targeting*, Cold Spring Harbour, New York, pp. 23-30 (1989).

Phillips, E. et al., "Size Reduction of Peptides and Proteins by Jet-Milling", *Respiratory Drug Delivery VI*, pp. 161-167 (1998).

Saleki-Gerhardt, A. et al., "Hydration and Dehydration of Crystalline and Amorphous Forms of Raffinose," *Journal of Pharmaceutical Sciences*, 84(3):318-323 (Mar. 1995).

Sambrook, et al., *Molecular Cloning: A Laboratory Manual*, 2nd. ed., "Concentrating Nucleic Acids: Precipitation with Ethynol or Isopropanol", pp. E.10-E.17, Cold Spring Harbor Laboratory Press (1989).

Sanchez, J. et al., "Recombinant System for Overexpression of Cholera Toxin B Subunit In Vibrio Cholerae as a Basis for Vaccine Development" *Proc. Natl. Acad. Sci.* USA 86:481-485 (1989).

Sarkar and Moore, "Immunization of Mice Against Murine Mammary Tumor Virus Infection and Mammary Tumor Development," *Cancer Research* 38:1470-1472 included.

Schamblin and Zografi. "Enthalpy Relaxation in Binary Amorphous Mixtures Containing Sucrose", *Pharmaceutical Research* 15(12): 1828-1834 (Dec. 1998).

Schebor, C. et al., "Color Formation Due to Non-Enzymatic Browning in Amorphous, Glassy, Anhydrous, Model Systems", *Food Chemistry* 65:427432 (1999).

Sciarra et al., "Aerosols", *Remington's Pharmaceutical Sciences*, Chap. 93, 17 Ed., Mack Publishing Company, Alfonso R. Gennaro, editor, pp. 1662-1677 (1985).

Sebhatu, T. et al., "Assessment of the Degree of Disorder in Crystalline Solids by Isothermal Microcalorimetry," *International Journal of Pharmaceutics* 104:135-144 (1994).

Sellers, S. P. et al., "Dry Powders of Stable Protein Formulations From Aqueous Solutions Prepared Using Supercritical C02-Assisted Aerosolization", *Journal of Pharmaceutical Sciences*, 90(6): 785-797 (2001).

Serajuddin, A. T. M. et al., "Effect of Thermal History on the Glassy State of Indapamide," *J. Pharm. Pharmacol.* 38:219-220 (1986).

Shalaev, E.Y. et al., "How Does Residual Water Affect the Solid-State Degradation of Drugs in The Amorphous State", *Journal of Pharmaceutical Sciences*, 85(11): 1137-111 (1996).

Shalaev, E.Y. et al., "Structural Glass Transitions and Thermophysical Processes in Amorphous Carbohydrates and Their Supersaturated Solutions," *J. Chem. Soc. Faraday Trans.* 91(10):1511-1517 (1995).

Singer et al., "Thermotolerance in *Saccharomyces cerevisiae*: the Yin and Yang of Trehalose", *Tibtech* 16:460-468. (1998).

Skrabanja et al., "Lyophilization of Biotechnology Products" *PDA J. Pharm. Sci. Technol.* 48(6):311.

Slade and Levine, "The Glassy State Phenomenon in Food Molecules," *The Glassy State in Foods*, Blanshard & Lillford, editors: 35-101 (1993).

Slade and Levine, "Non-Equilibrium Behavior of Small Carbohydrate-Water Systems," *Pure and Applied Chemistry*, 60(12): 1841-1864 (1988).

Sokolov et al., "Glassy Dynamics in DNA: Ruled by Water of Hydration" *Journal of Chemical Physics* 110(14):7053-7057 (1999).

Sola-Penna, Mauro et al, *Stabilization Against Thermal Inactivation Promoted by Sugars on Enzyme Structure and Function: Why is Trehalose More Effective Than Other Sugars?* 360(I) Archives of Biochemistry and Biophysics 10-14, Article No. BB9809606, (Dec. 1998).

Stribling, R. et al., "Aerosol Gene Delivery in Vivo," *Proc. Natl. Acad. Sci.* 89:11277-11281 (Dec. 1992).

Strickley, R. G. et al., "Solid-State Stability of Human Insulin II. Effect of Water on Reactive Intermediate Partitioning in Lyophiles from pH 2-5 Solutions: Stabilization Against Covalent Dimer Formation", *Journal of Pharmaceutical Sciences* 86(6):645-653 (1997).

Strom, A. R. and Kaasen. L. "Trehalose Metabolism in *Escherichia coli*: Stress Protection and Stress Regulation of Gene Expression", *Molecular Microbiology* 8(2):205-210 (1993).

Stubberud, L. et al., "The Use of Gravimetry for The Study of the Effect of Additives on the Moisture-Induced Recrystallisation of Amorphous State", *International Journal of Pharmaceutics* 163:145-156 (1998).

Sukenik et al., "Enhancement of a Chemical Reaction Rate by Proper Orientation of Reacting Molecules in the Solid State", *J. Am. Chem. Soc.* 97: 5290-5291 (Sep. 1975).

Sussich, F. et al., "Reversible Dehydration of Trehalose and Anhydrobiosis: From Solution State to an Exotic Crystal?", *Carbohydrate Research* 334:165-176 (2001).

Takahashi et al., "Induction of CD8+ cytotoxic T cells by immunization with purified HIV-1 envelope protein in ISCOMs", *Nature* 344:873-875 (Apr. 1990).

Tarelli, E. et al., "Additives to Biological Substances. 111. The Moisture Content and Moisture Uptake of Commonly Used Carrier Agents Undergoing Processing Conditions Similar to Those Used in the Preparation of International Biological Standards, " *Journal of Biological Standardization* 15:331-340 (1987).

Timko et al., "Thermal Analysis Studies of Glass Dispersion Systems", *Drug Devel. Ind. Pharm.* 10:425451 (1984).

Timsina, T. et al., "Drug Delivery to the Respiratory Tract Using Dry Powder Inhalers," *International Journal of Pharmaceutics* 101:1-13 (1994).

To et al., "Collapse. a Structural Transition in Freeze Dried Carbohydrates", *J. Fd. Technol.* 13: 567-581 (1978).

Toyama, A. (ed) *Handbook of Natural Product for food processing*, 9th Edition, Osaka, Japan, Shokuhin to Kagaku Sha, pp. 384 and 495 (ISBN4-87994-048-8),(1986).

Tsourouflis, S. et al., "Loss of Structure in Freeze-Dried Carbohydrates Solutions: Effect of Temperature, Moisture Content and Composition," *J. Sci. Fd. Agric.* 27:509 519 (1976).

Underwood et al., "A Novel Technique for the Administration of Bronchodilator Drugs Formulated as Dry Powders to the Anaesthetized Guinea Pig", *J. of Pharmacological Methods*, vol. 26, pp. 203-210, 1991.

Uritani, M. et al., "Protective Effect of Disaccharides on Restriction Endonucleases During Drying Under Vacuum." *J. Biochem.* 117:774-779 (1995).

Advertisement for "Stop 'n Grow" manufactured by The Mentholatum Co. Ltd., East Kilbride, Scotland G74 5P3.

Agrimi, U., et al. "Amyloid, Amyloid-Inducers, Cytokines and Heavy Metals in Scrapie and Other Human and Animal Subacute Spongiform Encephalopathies: Some Hypotheses", *Med. Hypotheses*, 40(2): 113-116 (1993).

Akers, M.J., et al., "Glycine Crystallization During Freezing: The Effects of Salt Form, pH, and Ionic Strength", *Pharmaceutical Research* 12(10):1457-1461 (1995).

Akoh, et al., "One-stage synthesis of raffinose fatty acid polyesters", *J. Food Sci.*, 52:1570-1576 (1987).

Alberts, B., et al., *Molecular Biology of the Cell*, $2^{nd}$ ed., Garland Publishing, Inc., Ch. 2, p. 58 (1989).

Aldous, et al., "The Crystallization of Hydrates from Amorphous Carbohydrates", *Cryo-Letters*, 16:181-186 (1995).

Allen, D.J., et al. "Determination of the Degree of Crystallinity in Solid-Solid Equilibria", *J. Pharm. Sci.*, 58:1190-1193 (1969).

Allison, S.D., et al., "Mechanisms of Protection of Cationic Lipid-DNA Complexes During Lyophilization", *Journal of Pharmaceutical Sciences* 89(5): 682-691 (2000).

Allison, S.D. and Anchordoquy, Thomas J., *Lyophilization of Nonviral Gene Delivery Systems*, Methods in Molecular Medicine, Nonviral Vectors for Gene Therapy, Ch. 18, p. 225-252 (Mark A. Findeis ed., Humana Press, 2001).

Amidon, G.E., et al., "Powder Flow Testing in Preformulation and Formulation Development", *Pharm. Manuf.*, 2: 20-31 (1985).

Anchordoquy, Thomas J., Physical Stabilization of DNA Based Therapeutics, 6(9): DDT 463-470 (May 2001).

Anekwe, J., et al., "Relaxation Constants as a Predictor of Protein Stabilization", *Biocalorimetry: Applications of Calorimetry in the Biological Science*, J.E. Ladbury and B.Z. Chowdhry, editors, John Wiley & Sons, pp. 243-251 (1998).

"Drug Absorption and Availability", Modern Pharmaceutics, $3^{rd}$ edition, G.S. Banker, et al. (eds), Marcel Dekker, Inc., pp. 145 (1996).

Bandara, G., et al., "Interarticular Expression of Biologically Active Interleukin 1-Receptor-Antagonist Protein by Ex Vivo Gene Transfer", *Proc. Natl. Acad. Sci.*, 90:10764-10768 (Nov. 1993).

Bell, J.H., et al., "Dry Powder Aerosols I: A New Powder Inhalation Device", *J. Pharm. Sci.*, 60(10): 1559-1564 (Oct. 1971).

Carpenter, John F., et al., "Rational Design of Stable Lyophilized Protein Formulations: Some Practical Advice", *Pharmaceutical Res.*, 14(8): 969-975 (1997).

Caughey, et al., "Sulphated Polyanion Inhibition of Scrapie-Associated PrP Accumulation in Cultured Cells", *J. Virol.*, 67(2): 643-650 (1993).

Chan, et al., "Formulation of Vaccine Ajuvant Muramyldipeptides (MDP). 1. Characterization of Amorphous and Crystalline Forms of a Muramyldipeptide Analogue", *Pharmaceutical Research*, 5(8): 523-527 (1988).

Chan, Hak-Kim, et al., "Solid State Characterization of Spray-Dried Powders of Recombinant Human Deoxyribonuclease (RhDNase)", *Journal of Pharmaceutical Sciences*, 87(5): 647-654 (1998).

Chavan, V., et al., "Effect of Rise in Simulated Inspiratory Flow Rate and Carrier Particle Size on Poweder Emptying From Dry Powder Inhalers", *AAPS Pharmsci 2000*; 2(2) article 10 [on-line] Retrieved from the Internet <URL: http://www.pharmsci.org> 7 pages (2000).

Chavan, V., et al, Effect of Particle Size and Rise in Simulated Inspiratory Flow Rate on Device Emptying in a Dry Powder Inhaler SYstem, [on-line] [retrieved Jan. 7, 2005] Retrieved from the Internet <URL: http://www.aapspharmsci.org/abstracts/AM_1999/1001.htm> 1 page (1999).

Chawla, et al., "Production of Spray Dried Salbutamol Sulphate for Use in Dry Powder Aerosol Formulation", *International Journal of Pharmaceutics*, 108: 233-240 (1994).

Chiou, et al., "Pharmaceutical Applications of Solid Dispersion Systems", *J. Pharm.*, 60(9): 1281-1302 (1971).

Cleland, et al., "The Development of Stable Protein Formulations: A Close Look at Protein Aggregation, Deamidation and Oxidation", *Critical Reviews in Therapeutic Drug Carrier Systems*, 10(4): 307-377 (1993).

Colaco, et al., "Extraordinary Stability of Enzymes Dreid in Trehalose: Simplified Molecular Biology", *Bio/Technology* 10: 1007-1011 (1992).

Colaco, et al., "Trehalose Stabilization of Biological Molecules", *Biotechnol. Internet.*, pp. 345, 347-350 (1992).

Colaco, et al., "Chapter 14: Chemistry of Protein Stabilization by Trehalose", *ACS Symposium Series 567, Formulation and Delivery of Proteins and Peptides*, J.L. Cleland & R. Langer, pp. 222-240 (1994).

Constantino, et al., "Moisture-Induced Aggregation of Lyophilized Insulin", *Pharmaceutical Research*, 11(1): 21-29 (1994).

Constantino, H.R., et al., "Effect of Mannitol Crystallization on the Stability and Aerosol Performance of a Spray-Dried Pharmaceutical Protein, Recombinant Humanized Anti-IgE Monoclonal Antibody", *Journal of Pharmaceutical Sciences*, 87(11): 1406-1411 (1998).

Craig, I.D., et al., "Maillard Reaction Kinetics in Model Preservation Systems in the Vicinity of the Glass Transition: Experiment and Theory", *J. Agric. Food Chem.* 49(10: 4706-4712 (2001).

Crommelin, et al., "Liposomes", Chapter 3, *Colloidal Drug Delivery Systems*, J. Kreuter, editor: 73-190 (1994).

Crowe, et al., "Are Freezing and Dehydration Similar Stress Vectors? A Comparison of Modes of Interaction of Stabilizing Solutes with Biomolecules", *Cryobiol.* 27: 219-231 (1990).

Crowe, et al., "Interactions of Sugars with Membranes", *Biochimica et Biophysica Acta*, 947: 367-384 (1988).

Crowe, John H., et al., "The Role of Vitrification in Anhydrobiosis", *Annu. Rev. Physiol.*, 60: 73-103 (1998).

Crowe, Lois M., et al., "Is Trehalose Special for Preserving Dry Biomaterials?", *Biophysical Journal*, 71: 2087-2093 (1996).

D'Hondt, "Possible Approaches to Develop Vaccines Against Hepatitis A", *Vaccine* 10 (Supplement 1): S48-S52 (1992).

Daemen, et al., "The Destruction of Enzymes and Bacteria During the Spray-Drying of Milk and Whey, 2. The Effect of the Drying Conditions", *Neth. Milk Dairy J.*, 36: 211-229 (1982).

Dalby, R.N., et al., "Droplets Drying and Electrostatic Collection a Novel Alternative to Conventional Comminution Techniques", *Journal of Biopharmaceutical Sciences* 3 (1/2): 091-099 (1992).

Dalby, et al., "Relationship Between Particles Morphology and Drug Release Properties After Hydration of Aerosols Properties Containing Liposome Forming Ingredients", *Pharmaceutical Research*, 5(10): S-94, Abstract PD 888 (1988).

Darrington, et al., "Evidence for a Common Intermediate in Insulin Deamidation and Covalent Dimer Formation: Effects of pH and Aniline Trapping in Dilute Acidic Solutions", *Journal of Pharmaceutical Sciences*, 84(3): 275-282 (1995).

DeCarlo, S., et al., "Unexpected Property of Trehakose as Observed by Cyro-Electron Microscopy", *Journal of Microscopy*, 196(1): 40-45 (1995).

DeYoung, "The AeroDose Multidose Inhaler Device Design and Delivery Characteristics", *Respiratory Drug Delivery VI*, p. 91 (1998).

Dose, et al., "Survival in Extreme Dryness and DNA-Single-Strand Breaks", *Advances in Space Research*, 12(4)221-229 (1992).

Dunbar, et al., "Dispersion and Characterization of Pharmaceutical Dry Powder Aerosols", *KONA* (Feb. 26, 2998).

During, M.J., et al., "Long-Term Behavioral Recovery in Parkinsonian Rats by an HSV Vector Expressing Tyrosine Hydrosylase", *Science*, 266(5189): 856-857 (Nov. 1994).

Edwards, A.D., et al., "Crystallization of Pure Anhydrous Polymorphs of Carbamazepine by Solution Enhanced Dispersion with Supercritical Fluids (SEDS™)", *Journal of Pharmaceutical Sciences*, 90(8): 1115-1124 (2001).

Edwards, et al., "Large Porous Particles for Pulmonary Drug Delivery", *Science*, vol. 276, pp. 1868-1871 (Jun. 1997).

Jovanovic-Peterson, L. et al., "Jet-injected insulin is associated with decreased antibody production and postprandial glucose variability when compared with needle injected insulin in gestational diabetic women," *Diabetes Care* 16(11):1479-1484 (Nov. 1993).

Kachura, "Method of Drying Lactic Acid Bacteria," Vinodelie I Vinogradarstvo SSSR 2:49-50, English Abstract only, one page (1985).

Kanna, K. et al., "Denaturation of Fish Muscle Protein by Dehydration" *Bull. Tokai Reg. Fish. Res. Lab.* 77:70-76 English abstract (1974).

Karmas. R. et al., "Effect of Glass Transition on Rates of Nonenzymatic Browning in Food Systems," *J. Agric. Food Chem.* 40:873-879 (1992).

Khan, R. "Chemistry and New Uses of Sucrose: How Important?" *Pure & Appl. Chem.* 56(7):833-844 (1984).

Khan, R. "Cyclic Acetals of 4,1',6'-Tricholoro-4,1',6'-Trideoxy-Galacto-Sucrose and Their Conversion Into Methyl Ether Derivatives," *Carb. Res.* 198:275-283 (1990).

Klein, T. M. et al., "High Velocity Microprojectiles for Delivering Nucleic Acids Into Living Cells," *Nature* 327:70-73 (1987).

Labuza el al., "Glass Transition Temperatures of Food Systems", [on-line] [retrieved Sep. 2005] Retrieved from the Internet <URL: http://faculty.che.umn.edu/fscn/TedLebuza/PDF_files/Isotherm_Folder/Tg%20compilation.pdf > pp. 1-31 (Jan. 1992).

Labrude, P. et al., "Protective Effect of Sucrose on Spray Drying of Ocxyhemoglobin," *Journal of Pharmaceutical Sciences.* 78(3):223-229 (1989).

Lai, M. C. et al., "Solid-State Chemical Stability of Proteins and Peptides", *Journal of Pharmaceutical Sciences* 88(5):489-500 (1999).

Laube, B. L. et al., "Targeting Aerosol Deposition in Patients With Cystic Fibrosis, Effects of Alterations in Particle Size and Inspiratory Flow Rate", *Chest* 118(4): 1069-1076 (2000).

Ledl, F., et al., "New Aspects of the Maillard Reaction in Foods and in the Human Body," *Ang. Chem. Int. Ed.* Engl. 29:565-594 (Jun. 1990).

Lee, C. K. *Developments in Food Carbohydrate* —2nd edition Applied Science Publishers, London, Table of Contents, 4 pages (1980).

Lehninger, Albert L. *The Molecular Basis of Cell Structure and Function Biochemistry*, Chapter 31, 859-890 (Worth Publishers Inc., 2nd edition, 1975).

Leslie, S. B. et al., "Trehalose and sucrose protect both membranes and proteins in intact bacteria during drying", *Appl. Env. Microbiol.* 61(10): 3592-3597 (1995).

Leuner, C. et al., "Improving Drug Solubility for Oral Delivery Using Solid Dispersions", *European Journal of Pharmaceutics and Biopharmaceutics* 50:47-60 (2000).

Levine et al., "Another View of Trehalose for Drying and Stabilizing Biological Materials," *Biopharm* 5:36-40 (1992).

Lin, S.-Y. et al., "Solid Particles of Drug-β-Cyclodextrin Inclusion Complexes Directly Prepared by a Spray-Drying Technique", *International Journal of Pharmaceutics*, 56:249-259 (1989).

Louis, P. et al., "Survival of *Escherichia coli* During Drying and Storage in The Presence of Compatible Solutes" *Appl. Microbiol. Biotechnol.* 41:684-688 (1994).

Lueckel, B. et al., "Effects of Formulation and Process Variables on the Aggregation of Freeze-Dried Interleukin-6 (IL-6) After Lyophilization and on Storage", *Pharmaceutical Development and Technology* 3(3):337-346 (1998).

Masinde, Lwandiko E., et al., "Aerosolized Aqueous Suspension of Poly(L-lactic Acid) Microspheres,", *100 International Journal of Pharmaceutics*, pp. 123-131 (1993).
MacKenzie, "Collapse During Freeze Drying-Qualitative and Quantitative Aspects." *Freeze Drying and Advanced Food Technology*, edited by Goldblith, Rey and Rothmayr: 277-307 (1975).
Makower, B. et al., "Equilibrium Moisture Content and Crystallization of Amorphous Sucrose and Glucose," *Agric. And Food Chem.* 4(I):72-77 (1956).
Martin, A. et at., States of Matter and Phase Equilibria Physical Pharmacy, Physical Chemical Principles in the Pharmaceutical Sciences, 3rd. ed., Chapter 4, 62-92 (1983).
Masters, K. *Spray Drying Handbook*, England; Longman Scientific & Technical, 5th ed., pp. 640-642 (1991).
Masters, K. *Spray Drying Handbook*, England; Longman Scientific & Technical and John Wiley & Sons, Inc., 5th ed., pp. 309-352 (1991).
Masters, K *Spray Drying Handbook*, 5th ed., Chapters 13 and 15, pp. 491-537 and 587-642 (1991).
Matsuda, Y. et al., "Amorphism and Physicochemical Stability of Spray Dried Frusemide," *J. Pharm. Pharmacol.* 44:627-633, received Nov. 7, 1991 (1992).
Mattern et al., "Formulation of Proteins in Vacuum-Dried Glasses. II. Process and Storage Stability in Sugar-Free Amino Acid Systems", Pharmaceutical Development & Technology 4(2):199-208 (1999).
Miller, D. P. et al., "Stabilization of Lactate Dehydrogenase Following Freeze Thawing and Vacuum-Drying in the Presence of Trehalose and Borate", *Pharmaceutical Research* 15(8):1215-1221(1998).
Monnier et al., *Mechanisms of Protection Against Damage Mediated by the Maillard Reaction in Aging Gerontology* 37:152-165 (1991).
Mouradian, R. et al., "Degradation of Functional Integrity During Long-Term. Storage of a Freeze-Dried Biological Membrane", *Cryobiology* 22: 119-127 (1985).
Moynihan et al., "Dependence of the Glass Transition Temperature on Heating and Cooling Rate", *J. Physical. Chem.* 78(26): 2673-2677 (1974).
Muller, et al., "On the Influence of Molecular Forces on the Deformation of an Elastic Sphere and It's Sticking to a Rigid Plane", *J. Colloid Interface Sci.*, 77: 91 (1980).
Mumenthaler, M. et al., "Feasibility Study on Spray-Drying Protein Pharmaceuticals: Recombinant Human Growth Hormone and Tissue-Type Plasminogen Activator," *Clinical Research* 11(l): 12-20 (1994).

Murphy, B. R. et al., "Chapter 19: Immunization Against Viruses", in *Fields of Virology*, 2nd Edition, vol. 1, Raven Press, pp. 469-502 (1990).

Murphy, Brian R. et al., *Fields Virology*, vol. 1, Chapter 16, *Immunization Against Virus Disease*, 467, at p. 468, first full paragraph, first column, lines 26-33 (Bernard N. Fields et al. eds., Lippincott-Raven Publishers, 3rd ed. 1996).

Mutterlein, et al., "New Technology for Generating Inhalation Aerosols—Preliminary Results with the Piezoelectrical Pocket-Inhaler", *J. Aerosol Med.*, 1: 231 (1988).

Nabel, G. J. et al., "Immunotherapy of Malignancy by In Vivo Gene Transfer Into Tumors," *Hum. Gene. Ther.* 3(4): 3 99-4 10 (Aug. 1992) Abstract only [on-line] [retrieved 112/21/04] Retrieved from the Internet < URL: http://www.ncbi.nlm.nih.gov/entrez/query.fcgi?cmd=Retrieve&db=pubmed&dopt=Abstr>.

Naini, V. et al., "Particles for Inhalation Produced by Spray Drying and Electrostatic Precipitation of Different Protein-Sugar Solutions", *Respiratory Drug Delivery V*, pp. 382-384 (1996).

Naini, V. et al., "Physicochemical Stability of Crystalline Sugars and Their Spray-Dried Forms: Dependence Upon Relative Humidity and Suitability for Use in Powder Inhalers", *Drug Development and Industrial Pharmacy* 24(10):895-909 (1998).

Niven, R. W., "Delivery of Biotherapeutics by Inhalation Aerosol," *Critical Reviews in Therapeutic Drug Carrier Systems*, 12(2&3):151-231 (1995).

Niven, R. W., "Delivery of Biotherapeutics by Inhalation Aerosols," *Pharmaceutical Technology* 72-75, 80 (Jul. 1993).

Norberg, J. et al., "Glass Transition in DNA From Molecular Dynamics Simulation", *Proc. Natl. Acad. Sci. USA* 93:10173-10176 (1996).

Notter, R.H., "Physical Chemistry and Physiological Activity of Pulmonary Surfactants", In: Surfactant Replacement Therapy (Eds. Shapiro and Notter, Alan R. Liss, Inc., New York), Chapter 2, pp. 19-71 (1989).

Oksanen et al., "The Relationship between the Glass Transition Temperature and Water Vapor Absorption by Poly(Vinylpyrrolidone)," *Pharmaceutical Research* 7(6): 654-657 and errata on p. 974(1990).

Okumura, K. et al., "Intratracheal Delivery of Calcitonin Dry Powder in Rats and Human Volunteers," *S.T.P. Pharmaceutical Sciences* 4(I):5 pages (Jan., Feb. 1994).

Onodera et al., "Glass Transition of Dehydrated Amorphous Solid", *Bull. Chem. Soc. Japan* 41(9):222 (1968).

Palmer, K.J., et al., "X-Ray Diffractometer and Microscopic Investigation of Crystallization of Amorphous Sucrose", *Agricultural and Food Chemistry* 4(1): 77-81 (Jan. 1956).

Parks, "Studies on Glass. II The Transition Between the Glassy and Liquid States in the Case of Glucose", *Journal of Physical Chemistry* 1366-1379 (1928).

Pearlman et al., "Formulation Strategies for Recombinant Proteins: Human Growth Hormone and Tissue Plasminogen Activator", *Therapeutic Peptides and Proteins, Formulation, Delivery and Targeting*, Cold Spring Harbour, New York, pp. 23-30 (1989).

Pekarek et al., "Double-walled polymer microspheres for controlled drug release," *Nature* 367:258-260 (1994).

Phillips, E. et al., "Size Reduction of Peptides and Proteins by Jet-Milling", *Respiratory Drug Delivery VI*, pp. 161-167 (1998).

Pikal, M. J., "Freeze-Drying of Proteins Part II: Formulation Selections," *Biopharm* 3(8):26-30 (Oct. 1990).

Pikal, M. J. et al., "The Stability of Insulin in Crystalline and Amorphous Solids: Observation of Greater Stability for the Amorphous Form", *Pharmaceutical Research* 14(10):1379-1387 (1997).

Pikal et al., "Thermal Decomposition of Amorphous β-Lactam Antibacterials", *Journal of Pharmaceutical Science* 66(9): 1312-1316 (Sep. 1977).

Pikal, M. J. et al., Errata of "The Stability of Insulin in Crystalline and Amorphous Solids: Observation of Greater Stability for the Amorphous Form," *Pharmaceutical Research* 15(2):362-363 (1998).

Pine, S. H. et al., "15-3 Oligosaccharides and Polysaccharides," *Organic Chemistry*, 4a' edition. McGraw-Hill International Book Company, p. 763 (1980).

Pisecky, J., "2. Evaporation and Membrane Filtration", *Handbook of Milk Powder Manufacture*, Niro A/S, Denmark, p. 3 (1997).

Pocchiari, M. et al., "Amphotericin B: A Novel Class of Antiscrapie Drugs," *J Infect. Dis.* 160(5):795-802 (Nov. 1989).

Prestrelski, S. J. el al., "Optimization of Lyophilization Conditions for Recombinant Human Interleukin-2 by Dried-State Conformational Analysis Using Fourier-Transform Infrared Spectroscopy," *Pharmaceutical Research* 12(9):1250-1259 (1995).

Prestrelski, S. J. et al., "Separation of Freezing- and Drying-Induced Denaturation of Lyophilized Proteins Using Stress-Specific Stabilization," *Archives of Biochemistry and Biophysics* 303(2 :465-473 (Jun. 1993).

"Aerosols, Metered-Dose Inhalers, and Dry Powder Inhalers", *Pharmacopeial Previews*, 22(6): 3065 (1996).

Quan. C. *Protein Science* 4(2):148, Abstract No. 490-T (1995).

Ramanujam, R. et al., "Ambient-Temperature-Stable Molecular Biology Reagents," *Biotechniques* 14(3):470-473 (1993).

Roos, "Phase Transitions of Mixtures of Amorphous Polysaccharides and Sugars," *Biotechnology Progress* 7(I): 49-53 (1991).

Rosen, Surfactants and Interfacial Phenomena, Second Edition, John Wiley & Sons, New York, pp. 326-329 (1989).

Roser, et al., "A Sweeter Way to Fresher Food" *New Scientist* pp. 25-28 (May 15, 1993).

Roser, B., "Trehalose, A New Approach to Premium Dried Foods," *Trends in Food Sci. and Tech.* pp. 166-169 (Jul. 1991).

Roser, B., "Trehalose Drying: A Novel Replacement for Freeze Drying" *Biopharm* 4:47-53 (1991).

Sacchetti, et al., "Spray-Drying and Supercritical Fluid Particle Generation Techniques", *Inhalation Aerosols: Physical and Biological Basis for Therapy*, A.J. Hickey, ed., Marcel Dekkar, New York, Chapter 11, p. 337 (1996).

Saleki-Gerhardt, A. et al., "Non-Isothermal and Isothermal Crystallization of Sucrose From the Amorphous State," *Pharmaceutical Research* 11 (8):1166-1173 (1994).

Sola-Penna, Mauro et al., *Stabilization Against Thermal Inactivation Promoted by Sugars on Enzyme Structure and Function: Why is Trehalose More Effective Than Other Sugars?* 360(1) Archives of Biochemistry and Biophysics 10-14, Article No. BB9809606, (Dec. 1998).

Stribling, R. et al., "Aerosol Gene Delivery in Vivo," *Proc. Natl. Acad. Sci.* 89:11277-11281 (Dec. 1992).

Strickley, R. G. et al., "Solid-State Stability of Human Insulin II. Effect of Water on Reactive Intermediate Partitioning in Lyophiles from pH 2-5 Solutions: Stabilization Against Covalent Dimer Formation", *Journal of Pharmaceutical Sciences* 86(6):645-653 (1997).

Strom, A. R. and Kaasen. L. "Trehalose Metabolism in *Escherichia coli*: Stress Protection and Stress Regulation of Gene Expression", *Molecular Microbiology* 8(2):205-210 (1993).

Stubberud, L. et al., "The Use of Gravimetry for the Study of the Effect of Additives on the Moisture-Induced Recrystallisation of Amorphous State", *International Journal of Pharmaceutics* 163:145-156 (1998).

Sukenik et al., "Enhancement of a Chemical Reaction Rate by Proper Orientation of Reacting Molecules in the Solid State", *J. Am. Chem. Soc.* 97: 5290-5291 (Sep. 1975).

Sussich, F. et al., "Reversible Dehydration of Trehalose and Anhydrobiosis: From Solution State to an Exotic Crystal?", *Carbohydrate Research* 334:165-176 (2001).

Takahashi et al., "Induction of CD8+ cytotoxic T cells by immunization with purified HIV-1 envelope protein in ISCOMs", *Nature* 344:873-875 (Apr. 1990).

Tarelli, E. et al., "Additives to Biological Substances. 111. The Moisture Content and Moisture Uptake of Commonly Used Carrier Agents Undergoing Processing Conditions Similar to Those Used in the Preparation of International Biological Standards, " *Journal of Biological Standardization* 15:331-340 (1987).

Timko et al., "Thermal Analysis Studies of Glass Dispersion Systems", *Drug Devel. Ind. Pharm.* 10:425451 (1984).

Timsina, T. et al., "Drug Delivery to the Respiratory Tract Using Dry Powder Inhalers", *International Journal of Pharmaceutics* 101:1-13 (1994).

To et al., "Collapse. a Structural Transition in Freeze Dried Carbohydrates", *J. Fd. Technol.* 13: 567-581 (1978).

Toyama, A. (ed) *Handbook of Natural Product for food processing*, 9th Edition, Osaka, Japan, Shokuhin to Kagaku Sha, pp. 384 and 495 (ISBN4-87994-048-8),(1986).

Tsourouflis, S. et al., "Loss of Structure in Freeze-Dried Carbohydrates Solutions: Effect of Temperature, Moisture Content and Composition," *J. Sci. Fd. Agric.* 27:509 519 (1976).

Underwood et al., "A Novel Technique for the Administration of Bronchodilator Drugs Formulated as Dry Powders to the Anaesthetized Guinea Pig", *J. of Pharmacological Methods*, vol. 26, pp. 203-210, 1991.

Uritani, M. et al., "Protective Effect of Disaccharides on Restriction Endonucleases During Drying Under Vacuum." *J. Biochem.* 117:774-779 (1995).

Vain et al., "Development of the particle inflow gun", *Plant Cell, Tissue and Organ Culture* 33:237-246 (1993).

Vavelyuk, O.L. et al., "Thermostability of DNA and Its Association with Vitrification", *Tsitologiya* 41(11):958-965 (1999).

Vidgrén, M. T. et al., "Comparison of Physical and Inhalation Properties of Spray-Dried and Mechanically Micronized Disodium Cromoglycate," *International Journal of Pharmaceutics* 35:139-144 (1987).

Vromans, H. et al., "Studies on Tableting Properties of Lactose. VII. The Effect of Variations in Primary Particle Size and Percentage of Amorphous Lactose in Spray Dried Lactose Products," *International Journal of Pharmaceutics* 35:29-36 (1987).

Wang, et al. eds. *Stability and characterization of protein and peptide drugs*, Table of Contents, 6 pages (1993).

Welsh, D. T., "The Role of Compatible Solutes in the Adaptation and Survival of *Escherichia coli*," Ph.D. Thesis Submitted to Department of Biological Sciences, University of Dundee. pp. 1-262 . (Aug. 1992).

Whittier, E., "Lactose and its Utilization: A Review," *J. Dairy Sci.* 27(7)505-537 (Jul. 1994).

William and Leopold, "The Glassy State in Corn Embryos" *Plant Physiology* 89:977-981 (1979).

Williams et al., "The Temperature Dependence of Relaxation Mechanisms in Amorphous Polymers and Other Glass Forming Liquids", *The Journal of the American Chemical Society* 77: 3701-3707 (1955).

Wolff, J. A. et al., "Grafting Fibroblasts Genetically Modified to Produce L-Dopa in a Rat Model of Parkinson Disease," *Proc. Natl. Acad. Sci.* 86:9011-9014 (Nov. 1989).

Xi, Y. G. et al., "Amphotericin B Treatment Dissociates in Vivo Replication of the Scrapie Agent From PrP Acummulation", *Nature* 356:598-601 (Apr. 1992).

York, "Powdered Raw Materials: Characterizing Batch Uniformity," *Respiratory Drug Delivery IV, Programs and Proceedings*, edited by Byron, Dalby and Farr: 83-91 (1994).

Yoshida, H. et al., "Absorption of Insulin Delivered to Rabbit Trachea Using Aerosol Dosage Form," *Journal of Pharmaceutical Sciences* 68(5): 670-671 (May 1979).

Yoshioka, M. el al., "Crystallisation of Indomethacin From the Amorphous State Below and Above Its Glass Transition Membrane," *Journal of Pharmaceutical Sciences* 83(12):1700-1705 (Dec. 1994).

Zubay, G. Biochemistry, Second Edition, pp. 39 & 169, Table 5-6 Major Steroid Hormones (1988).

Zubay, G. Biochemistry, Second Edition, pp. 216-232 "Structural Properties of DNA" (1988).

Nektar U.S. Appl. No. 08/044,358, "Compositions and Methods for Nucleic Acid Delivery to the Lung" filed by Patton et al. on Apr. 7, 1993, assigned to Inhale Therapeutic Systems.

Nektar U.S. Appl. No. 08/422,563, filed Apr. 14, 1995, Paper No. 17, Office communication mailed Apr. 3, 1998 (Patent No. 5,994,314).

Millqvist-Fureby et al. "Spray-Drying of Trypsin—Surface Characterisation and Activity Preservation" *Int. J. Pharm.* 108: 243-253 (1999).

Parasassi et al. "Calcium-Induced Phase Separation in Phospholipid Bilayers. A Fluoresence Anisotrophy" Cellular and Molecular Bio 32(3): 261-266 (1986).

Reboriraa, M.D. "Activity Coefficients of $CaCl_3$ and $MgCl_2$ in the Presence of Dipalmitoylphosphatidylcholine-Phosphatidylinositol Vesicles in Aqueous Media" Bioelectrochemistry and Bioenergetics 39: 101-108 (1996).

Royall et al. "Characterisation of Moisture Uptake Effects on the Glass Transitional Behavious of an Amorphous Drug Using Modulated Temperature DSC" Int. J. Pharm. 192: 39-46 (1999).

Satoh, Koichi. "Determination of Binding Constants of $Ca^{3+}$, $Na^+$Ions to Liposomal Membranes of Dipalmitoylphosphatidylcholine at Gel Phase by Patrick Electrophoresis" Biochim Biophys Acto 1239: 239-248 (1995).

Seddon, J.M. "Structure of the Inverted Hexagonal ($H_{11}$) Phase, and Non-Lamellar Phase Transitions of Lipids" Biochim Biophys Acto 1031: 1-69 (1990)., in particular p. 43-44 and 49-50.

* cited by examiner

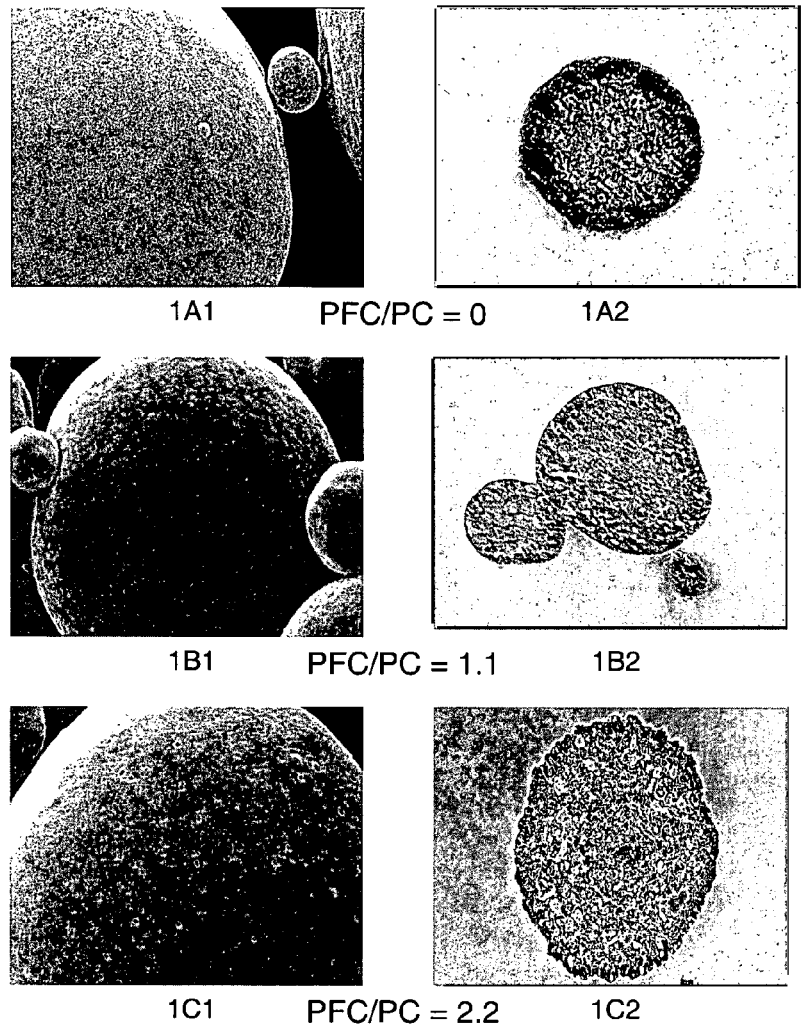
FIG. 1 (SHEET 1 OF 2)

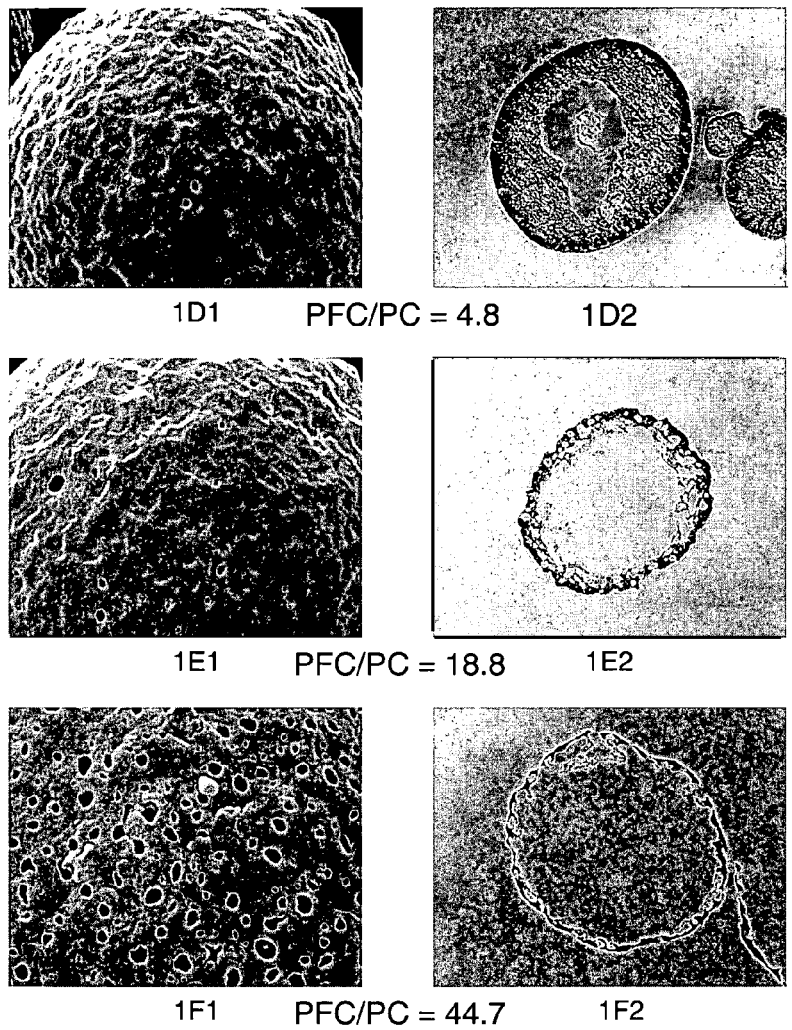
FIG. 1 (SHEET 2 OF 2)

ENGINEERED PARTICLES AND METHODS OF USE

CROSS REFERENCE TO RELATED APPLICATIONS

The present application is a divisional of U.S. application Ser. No. 09/219,736, filed Dec. 22, 1998 now U.S. Pat. No. 6,565,885, which is a continuation of PCT Application No.: US98/20602, filed Sep. 29, 1998, which is a continuation-in-part of U.S. patent application Ser. No. 09/133,848, filed Aug. 14, 1998 now abandoned, which is a continuation-in-part of U.S. patent application Ser. No. 09/106,932 filed Jun. 29, 1998 now abandoned which claims priority from U.S. Provisional Application Serial No.: 60/060,337 filed Sep. 29, 1997 and now lapsed.

FIELD OF THE INVENTION

One or more embodiments of the present invention relate to the formulation, methods of production, and methods of delivery, of perforated microstructures comprising an active agent.

BACKGROUND OF THE INVENTION

Targeted drug delivery means are particularly desirable where toxicity or bioavailability of the pharmaceutical compound is an issue. Specific drug delivery methods and compositions that effectively deposit the compound at the site of action potentially serve to minimize toxic side effects, lower dosing requirements and decrease therapeutic costs. In this regard, the development of such systems for pulmonary drug delivery has long been a goal of the pharmaceutical industry.

The three most common systems presently used to deliver drugs locally to the pulmonary air passages are dry powder inhalers (DPIs), metered dose inhalers (MDIs) and nebulizers. MDIs, the most popular method of inhalation administration, may be used to deliver medicaments in a solubilized form or as a dispersion. Typically MDIs comprise a Freon or other relatively high vapor pressure propellant that forces aerosolized medication into the respiratory tract upon activation of the device. Unlike MDIs, DPIs generally rely entirely on the patient's inspiratory efforts to introduce a medicament in a dry powder form to the lungs. Finally, nebulizers form a medicament aerosol to be inhaled by imparting energy to a liquid solution. More recently, direct pulmonary delivery of drugs during liquid ventilation or pulmonary lavage using a fluorochemical medium has also been explored. While each of these methods and associated systems may prove effective in selected situations, inherent drawbacks, including formulation limitations, can limit their use.

The MDI is dependent on the propulsive force of the propellant system used in its manufacture. Traditionally, the propellant system has consisted of a mixture of chlorofluorocarbons (CFCs) which are selected to provide the desired vapor pressure and suspension stability. Currently, CFCs such as Freon 11, Freon 12, and Freon 114 are the most widely used propellants in aerosol formulations for inhalation administration. While such systems may be used to deliver solubilized drug, the selected bioactive agent is typically incorporated in the form of a fine particulate to provide a dispersion. To minimize or prevent the problem of aggregation in such systems, surfactants are often used to coat the surfaces of the bioactive agent and assist in wetting the particles with the aerosol propellant. The use of surfactants in this way to maintain substantially uniform dispersions is said to "stabilize" the suspensions.

Unfortunately, traditional chlorofluorocarbon propellants are now believed to deplete stratospheric ozone and, as a consequence, are being phased out. This, in turn, has led to the development of aerosol formulations for pulmonary drug delivery employing so-called environmentally friendly propellants. Classes of propellants which are believed to have minimal ozone-depletion potential in comparison with CFCs are perfluorinated compounds (PFCs) and hydrofluoroalkanes (HFAs). While selected compounds in these classes may function effectively as biocompatible propellants, many of the surfactants that were effective in stabilizing drug suspensions in CFCs are no longer effective in these new propellant systems. As the solubility of the surfactant in the HFA decreases, diffusion of the surfactant to the interface between the drug particle and HFA becomes exceedingly slow, leading to poor wetting of the medicament particles and a loss of suspension stability. This decreased solubility for surfactants in HFA propellants is likely to result in decreased efficacy with regard to any incorporated bioactive agent.

More generally, drug suspensions in liquid fluorochemicals, including HFAs, comprise heterogeneous systems which usually require redispersion prior to use. Yet, because of factors such as patient compliance obtaining a relatively homogeneous distribution of the pharmaceutical compound is not always easy or successful. In addition, prior art formulations comprising micronized particulates may be prone to aggregation of the particles which can result in inadequate delivery of the drug. Crystal growth of the suspensions via Ostwald ripening may also lead to particle size heterogeneity and can significantly reduce the shelf-life of the formulation. Another problem with conventional dispersions comprising micronized dispersants is particle coarsening. Coarsening may occur via several mechanisms such as flocculation, fusion, molecular diffusion, and coalescence. Over a relatively short period of time these processes can coarsen the formulation to the point where it is no longer usable. As such, while conventional systems comprising fluorochemical suspensions for MDIs or liquid ventilation are certainly a substantial improvement over prior art non-fluorochemical delivery vehicles, the drug suspensions may be improved upon to enable formulations with improved stability that also offer more efficient and accurate dosing at the desired site.

Similarly, conventional powdered preparations for use in DPIs often fail to provide accurate, reproducible dosing over extended periods. In this respect, those skilled in the art will appreciate that conventional powders (i.e. micronized) tend to aggregate due to hydrophobic or electrostatic interactions between the fine particles. These changes in particle size and increases in cohesive forces over time tend to provide powders that give undesirable pulmonary distribution profiles upon activation of the device. More particularly, fine particle aggregation disrupts the aerodynamic properties of the powder, thereby preventing large amounts of the aerosolized medicament from reaching the deeper airways of the lung where it is most effective.

In order to overcome the unwanted increases in cohesive forces, prior art formulations have typically used large carrier particles comprising lactose to prevent the fine drug particles from aggregating. Such carrier systems allow for at least some of the drug particles to loosely bind to the lactose surface and disengage upon inhalation. However, substantial amounts of the drug fail to disengage from the large lactose particles and are deposited in the throat. As such, these carrier systems are relatively inefficient with respect to the fine particle fraction provided per actuation of the DPI. Another solution to particle aggregation is proposed in WO 98/31346 wherein particles having relatively large geometric diameters (i.e. preferably greater than 10 μm) are used to reduce the amount of particle interactions thereby preserving the flowability of the powder. As with the prior art carrier systems, the use of large particles apparently reduces the overall surface area of the powder preparation reportedly resulting in improvements in flowability and fine particle fraction. Unfortunately, the use of relatively large particles may result in dosing limitations when used in standard DPIs and provide for less than optimal dosing due to the potentially prolonged dissolution times. As such, there still remains a need for standard sized particles that resist aggregation and preserve the flowability and dispersibility of the resulting powder.

Accordingly, it is an object of the present invention to provide methods and preparations that advantageously allow for the nasal or pulmonary administration of powders having relatively high fine particle fractions.

It is a further object of the present invention to provide stabilized preparations suitable for aerosolization and subsequent administration to the pulmonary air passages of a patient in need thereof.

It is yet another object of the present invention to provide powders that may be used to provide stabilized dispersions.

It is still a further object of the present invention to provide powders exhibiting relatively low cohesive forces that are compatible for use in dry powder inhalers.

SUMMARY

An inhaleable powder composition comprises a plurality of particulate microstructures, the microstructures comprising a structural matrix comprising an active agent, calcium and a phospholipid, wherein said microstructures have a mean geometric diameter of 1-30 microns, a mean aerodynamic diameter of less than 5 microns, and a bulk density of less than about 0.5 g/cm$^3$.

In one version, the phospholipid comprises a gel to liquid crystal transition temperature of greater than 40° C.

BRIEF DESCRIPTION OF THE DRAWINGS

FIGS. 1A1 to 1F2 illustrate changes in particle morphology as a function of variation in the ratio of fluorocarbon blowing agent to phospholipid (PFC/PC) present in the spray dry feed. The micrographs, produced using scanning electron microscopy and transmission electron microscopy techniques, show that in the absence of FCs, or at low PFC/PC ratios, the resulting spray dried microstructures comprising gentamicin sulfate are neither particularly hollow nor porous. Conversely, at high PFC/PC ratios, the particles contain numerous pores and are substantially hollow with thin walls.

FIG. 2 depicts the suspension stability of gentamicin particles in Perflubron as a function of formulation PFC/PC ratio or particle porosity. The particle porosity increased with increasing PFC/PC ratio. Maximum stability was observed with PFC/PC ratios between 3 to 15, illustrating a preferred morphology for the perflubron suspension media.

DETAILED DESCRIPTION PREFERRED EMBODIMENTS

Figure 2:
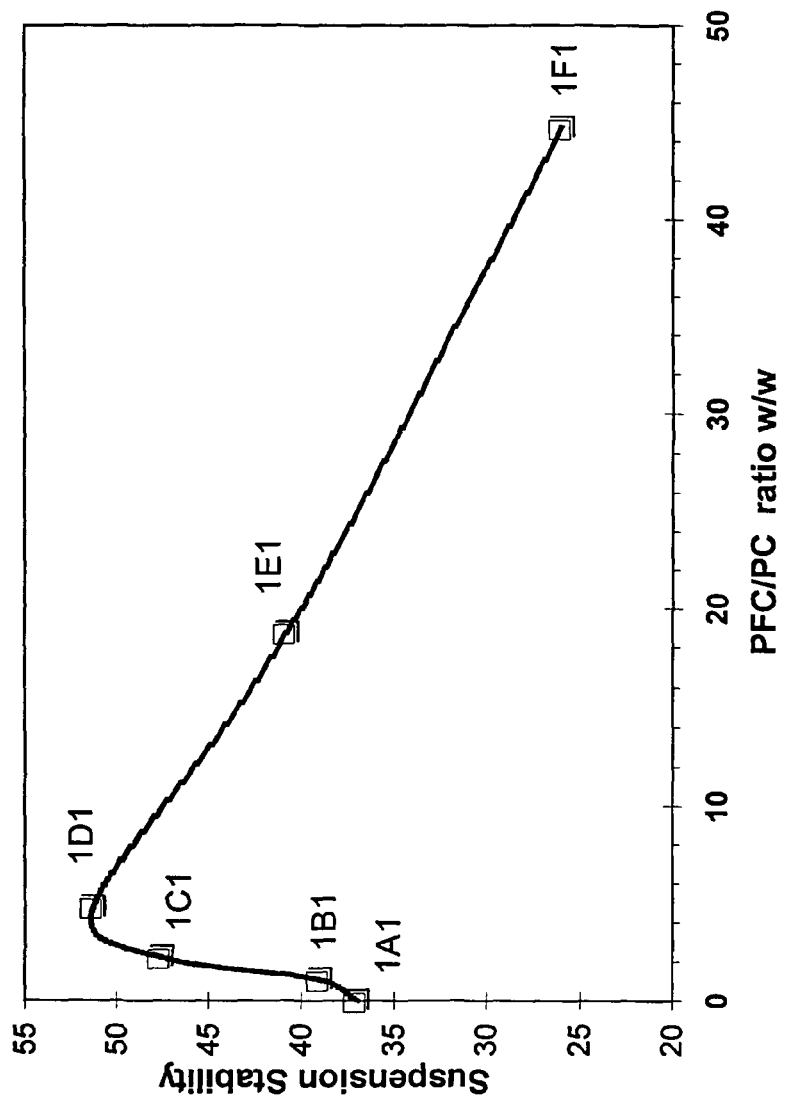
Figure 3:
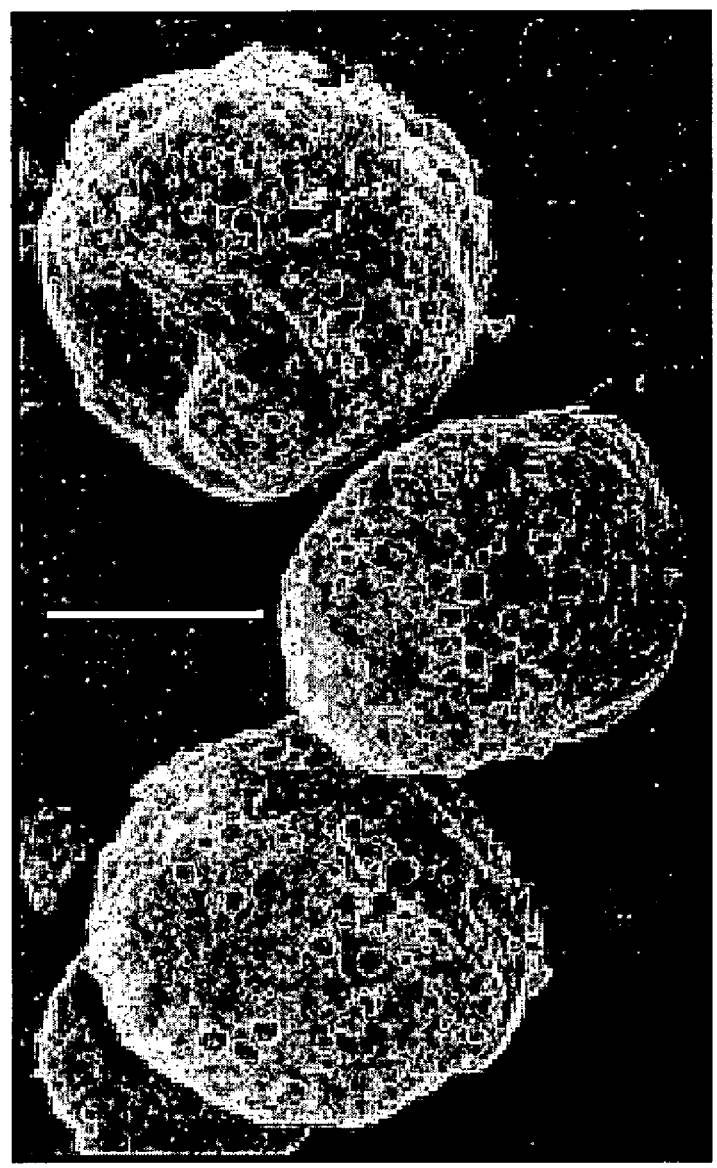
FIG. 3 is a scanning electron microscopy image of perforated microstructures comprising cromolyn sodium illustrating a preferred hollow/porous morphology.
Figure 4:
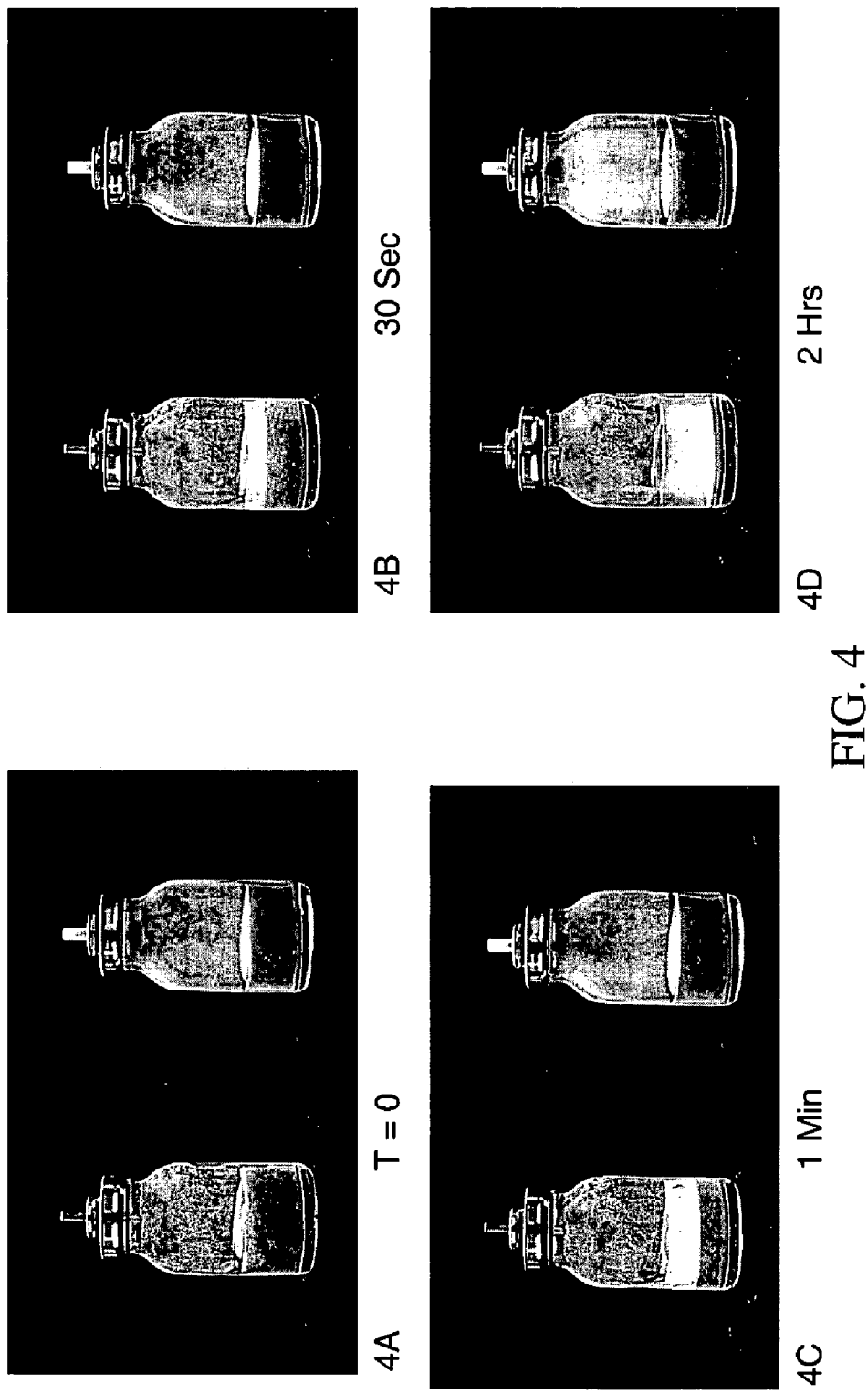
FIGS. 4A to 4D are photographs illustrating the enhanced stability provided by the dispersions of the present invention over time as compared to a commercial cromolyn sodium formulation (Intal®, Rhone-Poulenc-Rorer). In the photographs, the commercial formulation on the left rapidly sepa-
rates while the dispersion on the right, formed in accordance with the teachings herein, remains stable over an extended period.

While the present invention may be embodied in many different forms, disclosed herein are specific illustrative embodiments thereof that exemplify the principles of the invention. It should be emphasized that the present invention is not limited to the specific embodiments illustrated.

As discussed above, the present invention provides methods, systems and compositions that comprise perforated microstructures which, in preferred embodiments, may advantageously be used for the delivery of bioactive agents. More particularly, the present invention may provide for the delivery of bioactive agents to selected physiological target sites using perforated microstructure powders. In preferred embodiments, the bioactive agents are in a form for administration to at least a portion of the pulmonary air passages of a patient in need thereof. In particularly preferred embodiments, the disclosed perforated microstructure powders may be used in a dry state (e.g. as in a DPI) or in the form of a stabilized dispersion (e.g. as in a MDI, LDI or nebulizer formulation) to deliver bioactive agents to the nasal or pulmonary air passages of a patient. It will be appreciated that the perforated microstructures disclosed herein comprise a structural matrix that exhibits, defines or comprises voids, pores, defects, hollows, spaces, interstitial spaces, apertures, perforations or holes. The absolute shape (as opposed to the morphology) of the perforated microstructure is generally not critical and any overall configuration that provides the desired characteristics is contemplated as being within the scope of the invention. Accordingly, preferred embodiments can comprise approximately microspherical shapes. However, collapsed, deformed or fractured particulates are also compatible. With this caveat, it will further be appreciated that, particularly preferred embodiments of the invention comprise spray dried hollow, porous microspheres. In any case the disclosed powders of perforated microstructures provide several advantages including, but not limited to, increases in suspension stability, improved dispersibility, superior sampling characteristics, elimination of carrier particles and enhanced aerodynamics.

Those skilled in the art will appreciate that many of these aspects are of particular use for dry powder inhaler applications. Unlike prior art formulations, the present invention provides unique methods and compositions to reduce cohesive forces between dry particles, thereby minimizing particulate aggregation which can result in an improved delivery efficiency. To that end, the present invention provides for the formation and use of perforated microstructures and delivery systems comprising such powders, as well as individual components thereof. The disclosed powders may further be dispersed in selected suspension media to provide stabilized dispersions. Unlike prior art powders or dispersion for drug delivery, the present invention preferably employs novel techniques to reduce attractive forces between the particles. As such, the disclosed powders exhibit improved flowability and dispersibility while the disclosed dispersions exhibit reduced degradation by flocculation, sedimentation or creaming. As such, the disclosed preparations provide a highly flowable, dry powders that can be efficiently aerosolized, uniformly delivered and penetrate deeply in the lung or nasal passages. Furthermore, the perforated microstructures of the present invention result in surprisingly low throat deposition upon administration.

In preferred embodiments, the perforated microstructure powders have relatively low bulk density, allowing the powders to provide superior sampling properties over compositions known in the art. Currently, as explained above, many commercial dry powder formulations comprise large lactose particles which have micronized drug aggregated on their surface. For these prior art formulations, the lactose particles serve as a carrier for the active agents and as a bulking agent, thereby providing means to partially control the fine particle dose delivered from the device. In addition, the lactose particles provide the means for the commercial filling capability of dry particles into unit dose containers by adding mass and volume to the dosage form.

By way of contrast, the present invention uses methods and compositions that yield powder formulations having extraordinarily low bulk density, thereby reducing the minimal filling weight that is commercially feasible for use in dry powder inhalation devices. That is, most unit dose containers designed for DPIs are filled using fixed volume or gravimetric techniques. Contrary to prior art formulations, the present invention provides powders wherein the active or bioactive agent and the incipients or bulking agents make-up the entire inhaled particle. Compositions according to the present invention typically yield powders with bulk densities less than 0.5 g/cm$^3$ or 0.3 g/cm$^3$, preferably less 0.1 g/cm$^3$ and most preferably less than 0.05 g/cm$^3$. By providing particles with very low bulk density, the minimum powder mass that can be filled into a unit dose container is reduced, which eliminates the need for carrier particles. That is, the relatively low density of the powders of the present invention provides for the reproducible administration of relatively low dose pharmaceutical compounds. Moreover, the elimination of carrier particles will potentially minimize throat deposition and any "gag" effect, since the large lactose particles will impact the throat and upper airways due to their size.

The dispersions or powders may be used, for example, in conjunction with metered dose inhalers, dry powder inhalers, atomizers, nebulizers or liquid dose instillation (LDI) techniques to provide for effective drug delivery.

With regard to particularly preferred embodiments, the hollow and/or porous perforated microstructures substantially reduce attractive molecular forces, such as van de Waals forces, which dominate prior art powdered preparations and dispersions. In this respect, the powdered compositions typically have relatively low bulk densities which contribute to the flowability of the preparations while providing the desired characteristics for inhalation therapies. More particularly, the use of relatively low density perforated (or porous) microstructures or microparticulates significantly reduces attractive forces between the particles thereby lowering the shear forces and increasing the flowability of the resulting powders. The relatively low density of the perforated microstructures also provides for superior aerodynamic performance when used in inhalation therapy. When used in dispersions, the physical characteristics of the powders provide for the formation of stable preparations. Moreover, by selecting dispersion components in accordance with the teachings herein, interparticle attractive forces may further be reduced to provide formulations having enhanced stability.

With respect to the disclosed powders, the selected agent or bioactive agent, or agents, may be used as the sole structural component of the perforated microstructures. Conversely, the perforated microstructures may comprise one or more components (i.e. structural materials, surfactants, excipients, etc.) in addition to the incorporated agent. In particularly preferred embodiments, the suspended perforated microstructures will comprise relatively high concentrations of surfactant (greater than about 10% w/w) along with an incorporated bioactive agent(s). Finally, it should be appreciated that the particulate or perforated microstructure may be coated, linked or otherwise associated with an agent or bioactive agent in a non-integral manner. Whatever configuration is selected, it will be appreciated that any associated bioactive agent may be used in its natural form, or as one or more salts known in the art.

While the powders or stabilized dispersions of the present invention are particularly suitable for the pulmonary administration of bioactive agents, they may also be used for the localized or systemic administration of compounds to any location of the body. Accordingly, it should be emphasized that, in preferred embodiments, the formulations may be administered using a number of different routes including, but not limited to, the gastrointestinal tract, the respiratory tract, topically, intramuscularly, intraperitoneally, nasally, vaginally, rectally, aurally, orally or ocularly.

In accordance with the teachings herein the perforated microstructures will preferably be provided in a "dry" state. That is the microparticles will possess a moisture content that allows the powder to remain chemically and physically stable during storage at ambient temperature and easily dispersible. As such, the moisture content of the microparticles is typically less than 6% by weight, and preferably less 3% by weight. In some instances the moisture content will be as low as 1% by weight. Of course it will be appreciated that the moisture content is, at least in part, dictated by the formulation and is controlled by the process conditions employed, e.g., inlet temperature, feed concentration, pump rate, and blowing agent type, concentration and post drying.

With respect to the composition of the structural matrix defining the perforated microstructures, they may be formed of any material which possesses physical and chemical characteristics that are compatible with any incorporated active agents. While a wide variety of materials may be used to form the particles, in particularly preferred pharmaceutical embodiments the structural matrix is associated with, or comprises, a surfactant such as phospholipid or fluorinated surfactant. Although not required, the incorporation of a compatible surfactant can improve powder flowability, increase aerosol efficiency, improve dispersion stability, and facilitate preparation of a suspension. It will be appreciated that, as used herein, the terms "structural matrix" or "microstructure matrix" are equivalent and shall be held to mean any solid material forming the perforated microstructures which define a plurality of voids, apertures, hollows, defects, pores, holes, fissures, etc. that provide the desired characteristics. In preferred embodiments, the perforated microstructure defined by the structural matrix comprises a spray dried hollow porous microsphere incorporating at least one surfactant. It will further be appreciated that, by altering the matrix components, the density of the structural matrix may be adjusted. Finally, as will be discussed in further detail below, the perforated microstructures preferably comprise at least one active or bioactive agent.

As indicated, the perforated microstructures of the present invention may optionally be associated with, or comprise, one or more surfactants. Moreover, miscible surfactants may optionally be combined in the case where the microparticles are formulated in a suspension medium liquid phase. It will be appreciated by those skilled in the art that the use of surfactants, while not necessary to practice the instant invention, may further increase dispersion stability, powder flowability, simplify formulation procedures or increase efficiency of delivery. Of course combinations of surfactants, including the use of one or more in the liquid phase and one or more associated with the perforated microstructures are contemplated as being within the scope of the invention. By "associated with or comprise" it is meant that the structural matrix or perforated microstructure may incorporate, adsorb, absorb, be coated with or be formed by the surfactant.

In a broad sense, surfactants suitable for use in the present invention include any compound or composition that aids in the formation of perforated microparticles or provides enhanced suspension stability, improved powder dispersibility or decreased particle aggregation. The surfactant may comprise a single compound or any combination of compounds, such as in the case of co-surfactants. Particularly preferred surfactants are nonfluorinated and selected from the group consisting of saturated and unsaturated lipids, nonionic detergents, nonionic block copolymers, ionic surfactants and combinations thereof. In those embodiments comprising stabilized dispersions, such nonfluorinated surfactants will preferably be relatively insoluble in the suspension medium. It should be emphasized that, in addition to the aforementioned surfactants, suitable fluorinated surfactants are compatible with the teachings herein and may be used to provide the desired preparations.

Lipids, including phospholipids, from both natural and synthetic sources are particularly compatible with the present invention and may be used in varying concentrations to form the structural matrix. Generally compatible lipids comprise those that have a gel to liquid crystal phase transition greater than about 40° C. Preferably the incorporated lipids are relatively long chain (i.e. $C_{16}$-$C_{22}$) saturated lipids and more preferably comprise phospholipids. Exemplary phospholipids useful in the disclosed stabilized preparations comprise dilauroylphosphatidylcholine, dioleoylphosphatidylcholine, dipalmitoylphosphatidylcholine, disteroylphosphatidylcholine, diarachidoylphosphatidylcholine, dibehenoylphosphatidylcholine, short-chain phosphatidylcholines, long-chain saturated phosphatidylethanolamines, long-chain saturated phosphatidylserines, long-chain saturated phosphatidyiglycerols, long-chain saturated phosphatidylinositols, glycolipids, ganglioside GM1, sphingomyelin, phosphatidic acid, cardiolipin; lipids bearing polymer chains such as polyethylene glycol, chitin, hyaluronic acid, or polyvinylpyrrolidone; lipids bearing sulfonated mono-, di-, and polysaccharides; fatty acids such as palmitic acid, stearic acid, and oleic acid; cholesterol, cholesterol esters, and cholesterol hemisuccinate. Due to their excellent biocompatibility characteristics, phospholipids and combinations of phospholipids and poloxamers are particularly suitable for use in the pharmaceutical embodiments disclosed herein.

Compatible nonionic detergents comprise: sorbitan esters including sorbitan trioleate (Span® 85), sorbitan sesquioleate, sorbitan monooleate, sorbitan monolaurate, polyoxyethylene (20) sorbitan monolaurate, and polyoxyethylene (20) sorbitan monooleate, oleyl polyoxyethylene (2) ether, stearyl polyoxyethylene (2) ether, lauryl polyoxyethylene (4) ether, glycerol esters, and sucrose esters. Other suitable nonionic detergents can be easily identified using McCutcheon's Emulsifiers and Detergents (McPublishing Co., Glen Rock, N.J.) which is incorporated herein in its entirety. Preferred block copolymers include diblock and triblock copolymers of polyoxyethylene and polyoxypropylene, including poloxamer 188 (Pluronic® F-68), poloxamer 407 (Pluronic® F-127), and poloxamer 338. Ionic surfactants such as sodium sulfosuccinate, and fatty acid soaps may also be utilized. In preferred embodiments the microstructures may comprise oleic acid or its alkali salt.

In addition to the aforementioned surfactants, cationic surfactants or lipids are preferred especially in the case of delivery or RNA or DNA. Examples of suitable cationic lipids include: DOTMA, N-[1-(2,3-dioleyloxy)propyl]-N,N,N-trimethylammonium chloride; DOTAP, 1,2-dioleyloxy-3-(trimethylammonio)propane; and DOTB, 1,2-dioleyl-3-(4'-trimethylammonio)butanoyl-sn-glycerol. Polycationic amino acids such as polylysine, and polyarginine are also contemplated.

Besides those surfactants enumerated above, it will further be appreciated that a wide range of surfactants may optionally be used in conjunction with the present invention. Moreover, the optimum surfactant or combination thereof for a given application can readily be determined by empirical studies that do not require undue experimentation. Finally, as discussed in more detail below, surfactants comprising the structural matrix may also be useful in the formation of precursor oil-in-water emulsions (i.e. spray drying feed stock) used during processing to form the perforated microstructures.

Unlike prior art formulations, it has surprisingly been found that the incorporation of relatively high levels of surfactants (e.g., phospholipids) may be used to improve powder dispersibility, increase suspension stability and decrease powder aggregation of the disclosed applications. That is, on a weight to weight basis, the structural matrix of the perforated microstructures may comprise relatively high levels of surfactant. In this regard, the perforated microstructures will preferably comprise greater than about 1%, 5%, 10%, 15%, 18%, or even 20% w/w surfactant. More preferably, the perforated microstructures will comprise greater than about 25%, 30%, 35%, 40%, 45%, or 50% w/w surfactant. Still other exemplary embodiments will comprise perforated microstructures wherein the surfactant or surfactants are present at greater than about 55%, 60%, 65%, 70%, 75%, 80%, 85%, 90% or even 95% w/w. In selected embodiments the perforated microstructures will comprise essentially 100% w/w of a surfactant such as a phospholipid. Those skilled in the art will appreciate that, in such cases, the balance of the structural matrix (where applicable) will likely comprise a bioactive agent or non surface active excipients or additives.

While such surfactant levels are preferably employed in perforated microstructures, they may be used to provide stabilized systems comprising relatively nonporous, or substantially solid, particulates. That is, while preferred embodiments will comprise perforated microstructures associated with high levels of surfactant, acceptable microspheres may be formed using relatively low porosity particulates of the same surfactant concentration (i.e. greater than about 20% w/w). In this respect such high surfactant embodiments are specifically contemplated as being within the scope of the present invention.

In other preferred embodiments, of the invention the structural matrix defining the perforated microstructure optionally comprises synthetic or natural polymers or combinations thereof. In this respect useful polymers comprise polylactides, polylactide-glycolides, cyclodextrins, polyacrylates, methylcellulose, carboxymethylcellulose, polyvinyl alcohols, polyanhydrides, polylactams, polyvinyl pyrrolidones, polysaccharides (dextrans, starches, chitin, chitosan, etc.), hyaluronic acid, proteins, (albumin, collagen, gelatin, etc.). Examples of polymeric resins that would be useful for the preparation of perforated ink microparticles include: styrene-butadiene, styrene-isoprene, styrene-acrylonitrile, ethylene-vinyl acetate, ethylene-acrylate, ethylene-acrylic acid, ethylene-methylacrylatate, ethylene-ethyl acrylate, vinyl-methyl methacrylate, acrylic acid-methyl methacrylate, and vinyl chloride-vinyl acetate. Those skilled in the art will appreciate that, by selecting the appropriate polymers, the delivery efficiency of the perforated microparticles and/or the stability of the dispersions may be tailored to optimize the effectiveness of the active or bioactive agent.

Besides the aforementioned polymer materials and surfactants, it may be desirable to add other excipients to a microsphere formulation to improve particle rigidity, production yield, delivery efficiency and deposition, shelf-life and patient acceptance. Such optional excipients include, but are not limited to: coloring agents, taste masking agents, buffers, hygroscopic agents, antioxidants, and chemical stabilizers. Further, various excipients may be incorporated in, or added to, the particulate matrix to provide structure and form to the perforated microstructures (i.e. microspheres such as latex particles). In this regard it will be appreciated that the rigidifying components can be removed using a post-production technique such as selective solvent extraction.

Other rigidifying excipients may include, but are not limited to, carbohydrates including monosaccharides, disaccharides and polysaccharides. For example, monosaccharides such as dextrose (anhydrous and monohydrate), galactose, mannitol, D-mannose, sorbitol, sorbose and the like; disaccharides such as lactose, maltose, sucrose, trehalose, and the like; trisaccharides such as raffinose and the like; and other carbohydrates such as starches (hydroxyethylstarch), cyclodextrins and maltodextrins. Amino acids are also suitable excipients with glycine preferred. Mixtures of carbohydrates and amino acids are further held to be within the scope of the present invention. The inclusion of both inorganic (e.g. sodium chloride, calcium chloride, etc.), organic salts (e.g. sodium citrate, sodium ascorbate, magnesium gluconate, sodium gluconate, tromethamine hydrochloride, etc.) and buffers is also contemplated. The inclusion of salts and organic solids such as ammonium carbonate, ammonium acetate, ammonium chloride or camphor are also contemplated.

Yet other preferred embodiments include perforated microstructures that may comprise, or may be coated with, charged species that prolong residence time at the point of contact or enhance penetration through mucosae. For example, anionic charges are known to favor mucoadhesion while cationic charges may be used to associate the formed microparticulate with negatively charged bioactive agents such as genetic material. The charges may be imparted through the association or incorporation of polyanionic or polycationic materials such as polyacrylic acids, polylysine, polylactic acid and chitosan.

In addition to, or instead of, the components discussed above, the perforated microstructures will preferably comprise at least one active or bioactive agent. As used herein, the term "active agent" simply refers to a substance that enables the perforated microstructures to perform the desired function. Further, the term "active agent" shall be held inclusive of the term "bioactive agent" unless otherwise dictated by contextual restraints. As to the term "bioactive agent" it shall be held to comprise any substance that is used in connection with an application that is therapeutic or diagnostic in nature, such as methods for diagnosing the presence or absence of a disease in a patient, the diagnosis or treatment of a disease, and a condition or physiological abnormality in a patient. Particularly preferred bioactive agents for use in accordance with the invention include anti-allergics, peptides and proteins, pulmonary lung surfactants, bronchodilators and anti-inflammatory steroids for use in the treatment of respiratory disorders such as asthma by inhalation therapy. Preferred active agents for use in accordance with the present invention include pigments, dyes, inks, paints, detergents, food sweeteners, spices, adsorbants, antiinflammatories, antineoplastics, anesthetics, anti-tuberculars, imaging agents, cardiovascular agents, enzymes, steroids, genetic material, viral vectors, antisense scents, proteins, peptides and combinations thereof. In preferred embodiments the bioactive agents comprise compounds which are to be administered systemically (i.e. to the systemic circulation of a patient) such as peptides, proteins or polynucleotides. absorbents, catalysts, nucleating agents, thickening agents, polymers, resins, insulators, fillers, fertilizers, phytohormones, insect pheromones, insect repellents, pet repellents, antifouling agents, pesticides, fungicides, disinfectants, perfumes, deodorants, and combinations of thereof. As will be disclosed in more detail below, the bioactive agent may be incorporated, blended in, coated on or otherwise associated with the perforated microstructure.

It will be appreciated that the perforated microstructures of the present invention may exclusively comprise one or more active or bioactive agents (i.e. 100% w/w). However, in selected embodiments the perforated microstructures may incorporate much less bioactive agent depending on the activity thereof. Accordingly, for highly active materials the perforated microstructures may incorporate as little as 0.001% by weight although a concentration of greater than about 0.1% w/w is preferred. Other embodiments of the invention may comprise greater than about 5%, 10%, 15%, 20%, 25%, 30% or even 40% w/w active or bioactive agent. Still more preferably the perforated microstructures may comprise greater than about 50%, 60%, 70%, 75%, 80% or even 90% w/w active or bioactive agent. The precise amount of active or bioactive agent incorporated in the perforated microstructures of the present invention is dependent upon the agent of choice, the required dose, and the form of the agent actually used for incorporation. Those skilled in the art will appreciate that such determinations may be made by using well-known pharmacological techniques in combination with the teachings of the present invention.

With regard to pharmaceutical preparations, any bioactive agent that may be formulated in the disclosed perforated microstructures is expressly held to be within the scope of the present invention. In particularly preferred embodiments, the selected bioactive agent may be administered in the form of an aerosolized medicaments. Accordingly, particularly compatible bioactive agents comprise any drug that may be formulated as a flowable dry powder or which is relatively insoluble in selected dispersion media. In addition, it is preferred that the formulated agents are subject to pulmonary or nasal uptake in physiologically effective amounts. Compatible bioactive agents comprise hydrophilic and lipophilic respiratory agents, pulmonary surfactants, bronchodilators, antibiotics, antivirals, anti-inflammatories, steroids, antihistaminics, leukotriene inhibitors or antagonists, anticholinergics, antineoplastics, anesthetics, enzymes, cardiovascular agents, genetic material including DNA and RNA, viral vectors, immunoactive agents, imaging agents, vaccines, immunosuppressive agents, peptides, proteins and combinations thereof. Particularly preferred bioactive agents for inhalation therapy comprise mast cell inhibitors (anti-allergics), bronchodilators, and anti-inflammatory steroids such as, for example, cromoglycate (e.g. the sodium salt), and albuterol (e.g. the sulfate salt).

More specifically, exemplary medicaments or bioactive agents may be selected from, for example, analgesics, e.g. codeine, dihydromorphine, ergotamine, fentanyl, or morphine; anginal preparations, e.g. diltiazem; mast cell inhibitors, e.g. cromolyn sodium; antiinfectives, e.g. cephalosporins, macrolides, quinolines, penicillins, streptomycin, sulphonamides, tetracyclines and pentamidine; antihistamines, e.g. methapyrilene; anti-inflammatories, e.g. fluticasone propionate, beclomethasone dipropionate, flunisolide, budesonide, tripedane, cortisone, prednisone, prednisilone, dexamethasone, betamethasone, or triamcinolone acetonide; antitussives, e.g. noscapine; bronchodilators, e.g. ephedrine, adrenaline, fenoterol, formoterol, isoprenaline, metaproterenol, salbutamol, albuterol, salmeterol, terbutaline; diuretics, e.g. amiloride; anticholinergics, e.g. ipatropium, atropine, or oxitropium; lung surfactants e.g. Surfaxin, Exosurf, Survanta; xanthines, e.g. aminophylline, theophylline, caffeine; therapeutic proteins and peptides, e.g. DNAse, insulin, glucagon, LHRH, nafarelin, goserelin, leuprolide, interferon, rhu IL-1 receptor, macrophage activation factors such as lymphokines and muramyl dipeptides, opioid peptides and neuropeptides such as enkaphalins, endophins, renin inhibitors, cholecystokinins, DNAse, growth hormones, leukotriene inhibitors and the like. In addition, bioactive agents that comprise an RNA or DNA sequence, particularly those useful for gene therapy, genetic vaccination, genetic tolerization or antisense applications, may be incorporated in the disclosed dispersions as described herein. Representative DNA plasmids include, but are not limited to pCMVβ (available from Genzyme Corp, Framington, Mass.) and pCMV-β-gal (a CMV promotor linked to the *E. coli* Lac-Z gene, which codes for the enzyme β-galactosidase).

In any event, the selected active or bioactive agent(s) may be associated with, or incorporated in, the perforated microstructures in any form that provides the desired efficacy and is compatible with the chosen production techniques. As used herein, the terms "associate" or "associating" mean that the structural matrix or perforated microstructure may comprise, incorporate, adsorb, absorb, be coated with or be formed by the active or bioactive agent. Where appropriate, the actives may be used in the form of salts (e.g. alkali metal or amine salts or as acid addition salts) or as esters or as solvates (hydrates). In this regard the form of the active or bioactive agents may be selected to optimize the activity and/or stability of the actives and/or to minimize the solubility of the agent in the suspension medium and/or to minimize particle aggregation.

It will further be appreciated that the perforated microstructures according to the invention may, if desired, contain a combination of two or more active ingredients. The agents may be provided in combination in a single species of perforated microstructure or individually in separate species of perforated microstructures. For example, two or more active or bioactive agents may be incorporated in a single feed stock preparation and spray dried to provide a single microstructure species comprising a plurality of active agents. Conversely, the individual actives could be added to separate stocks and spray dried separately to provide a plurality of microstructure species with different compositions. These individual species could be added to the suspension medium or dry powder dispensing compartment in any desired proportion and placed in the aerosol delivery system as described below. Further, as alluded to above, the perforated microstructures (with or without an associated agent) may be combined with one or more conventional (e.g. a micronized drug) active or bioactive agents to provide the desired dispersion stability or powder dispersibility.

Based on the foregoing, it will be appreciated by those skilled in the art that a wide variety of active or bioactive agents may be incorporated in the disclosed perforated microstructures. Accordingly, the list of preferred active agents above is exemplary only and not intended to be limiting. It will also be appreciated by those skilled in the art that the proper amount of bioactive agent and the timing of the dosages may be determined for the formulations in accordance with already existing information and without undue experimentation.

As seen from the passages above, various components may be associated with, or incorporated in the perforated microstructures of the present invention. Similarly, several techniques may be used to provide particulates having the desired morphology (e.g. a perforated or hollow/porous configuration), dispersibility and density. Among other methods, perforated microstructures compatible with the instant invention may be formed by techniques including spray drying, vacuum drying, solvent extraction, emulsification or lyophilization, and combinations thereof. It will further be appreciated that the basic concepts of many of these techniques are well known in the prior art and would not, in view of the teachings herein, require undue experimentation to adapt them so as to provide the desired perforated microstructures.

While several procedures are generally compatible with the present invention, particularly preferred embodiments typically comprise perforated microstructures formed by spray drying. As is well known, spray drying is a one-step process that converts a liquid feed to a dried particulate form. With respect to pharmaceutical applications, it will be appreciated that spray drying has been used to provide powdered material for various administrative routes including inhalation. See, for example, M. Sacchetti and M. M. Van Oort in: Inhalation Aerosols: Physical and Biological Basis for Therapy, A. J. Hickey, ed. Marcel Dekkar, New York, 1996, which is incorporated herein by reference.

In general, spray drying consists of bringing together a highly dispersed liquid, and a sufficient volume of hot air to produce evaporation and drying of the liquid droplets. The preparation to be spray dried or feed (or feed stock) can be any solution, course suspension, slurry, colloidal dispersion, or paste that may be atomized using the selected spray drying apparatus. In preferred embodiments the feed stock will comprise a colloidal system such as an emulsion, reverse emulsion, microemulsion, multiple emulsion, particulate dispersion, or slurry. Typically the feed is sprayed into a current of warm filtered air that evaporates the solvent and conveys the dried product to a collector. The spent air is then exhausted with the solvent. Those skilled in the art will appreciate that several different types of apparatus may be used to provide the desired product. For example, commercial spray dryers manufactured by Buchi Ltd. or Niro Corp. will effectively produce particles of desired size.

It will further be appreciated that these spray dryers, and specifically their atomizers, may be modified or customized for specialized applications, i.e. the simultaneous spraying of two solutions using a double nozzle technique. More specifically, a water-in-oil emulsion can be atomized from one nozzle and a solution containing an anti-adherent such as mannitol can be co-atomized from a second nozzle. In other cases it may be desirable to push the feed solution though a custom designed nozzle using a high pressure liquid chromatography (HPLC) pump. Provided that microstructures comprising the correct morphology and/or composition are produced the choice of apparatus is not critical and would be apparent to the skilled artisan in view of the teachings herein.

While the resulting spray-dried powdered particles typically are approximately spherical in shape, nearly uniform in size and frequently are hollow, there may be some degree of irregularity in shape depending upon the incorporated medicament and the spray drying conditions. In many instances dispersion stability and dispersibility of the perforated microstructures appears to be improved if an inflating agent (or blowing agent) is used in their production. Particularly preferred embodiments may comprise an emulsion with the inflating agent as the disperse or continuous phase. The inflating agent is preferably dispersed with a surfactant solution, using, for instance, a commercially available microfluidizer at a pressure of about 5000 to 15,000 psi. This process forms an emulsion, preferably stabilized by an incorporated surfactant, typically comprising submicron droplets of water immiscible blowing agent dispersed in an aqueous continuous phase. The formation of such emulsions using this and other techniques are common and well known to those in the art. The blowing agent is preferably a fluorinated compound (e.g. perfluorohexane, perfluorooctyl bromide, perfluorodecalin, perfluorobutyl ethane) which vaporizes during the spray-drying process, leaving behind generally hollow, porous aerodynamically light microspheres. As will be discussed in more detail below, other suitable liquid blowing agents include nonfluorinated oils, chloroform, Freons, ethyl acetate, alcohols and hydrocarbons. Nitrogen and carbon dioxide gases are also contemplated as a suitable blowing agent.

Besides the aforementioned compounds, inorganic and organic substances which can be removed under reduced pressure by sublimation in a post-production step are also compatible with the instant invention. These sublimating compounds can be dissolved or dispersed as micronized crystals in the spray drying feed solution and include ammonium carbonate and camphor. Other compounds compatible with the present invention comprise rigidifying solid structures which can be dispersed in the feed solution or prepared in-situ. These structures are then extracted after the initial particle generation using a post-production solvent extraction step. For example, latex particles can be dispersed and subsequently dried with other wall forming compounds, followed by extraction with a suitable solvent.

With regard to the formation of the perforated microstructures it will be appreciated that, in preferred embodiments, the particles will be spray dried using commercially available equipment. In this regard the feed stock will preferably comprise a blowing agent that may be selected from fluorinated compounds and nonfluorinated oils. Preferably, the fluorinated compounds will have a boiling point of greater than about 60° C. Within the context of the instant invention the fluorinated blowing agent may be retained in the perforated microstructures to further increase the dispersibility of the resulting powder or improve the stability of dispersions incorporating the same. Further, nonfluorinated oils may be used to increase the solubility of selected bioactive agents (e.g. steroids) in the feed stock, resulting in increased concentrations of bioactive agents in the perforated microstructures.

The blowing agent may be dispersed in the carrier using techniques known in the art for the production of homogenous dispersions such a sonication, mechanical mixing or high pressure homogenization. Other methods contemplated for the dispersion of blowing agents in the feed solution include co-mixing of two fluids prior to atomization as described for double nebulization techniques. Of course, it will be appreciated that the atomizer can be customized to optimize the desired particle characteristics such as particle size. In special cases a double liquid nozzle may be employed. In another embodiment, the blowing agent may be dispersed by introducing the agent into the solution under elevated pressures such as in the case of nitrogen or carbon dioxide gas.

Although the perforated microstructures are preferably formed using a blowing agent as described above, it will be appreciated that, in some instances, no additional blowing agent is required and an aqueous dispersion of the medicament and/or excipients and surfactant(s) are spray dried directly. In such cases, the formulation may be amenable to process conditions (e.g., elevated temperatures) that may lead to the formation of hollow, relatively porous microparticles. Moreover, the medicament may possess special physicochemical properties (e.g., high crystallinity, elevated melting temperature, surface activity, etc.) that makes it particularly suitable for use in such techniques.

When a blowing agent is employed, the degree of porosity and dispersibility of the perforated microstructure appears to depend, at least in part, on the nature of the blowing agent, its concentration in the feed stock (e.g. as an emulsion), and the spray drying conditions. With respect to controlling porosity and, in suspensions, dispersibility it has surprisingly been found that the use of compounds, heretofore unappreciated as blowing agents, may provide perforated microstructures having particularly desirable characteristics. More particularly, in this novel and unexpected aspect of the present invention it has been found that the use of fluorinated compounds having relatively high boiling points (i.e. greater than about 40° C.) may be used to produce particulates that are particularly porous. Such perforated microstructures are especially suitable for inhalation therapies. In this regard it is possible to use fluorinated or partially fluorinated blowing agents having boiling points of greater than about 40° C., 50° C., 60° C., 70° C., 80° C., 90° C. or even 95° C. Particularly preferred blowing agents have boiling points greater than the boiling point of water, i.e. greater than 100° C. (e.g. perflubron, perfluorodecalin). In addition blowing agents with relatively low water solubility ($<10^{-6}$ M) are preferred since they enable the production of stable emulsion dispersions with mean weighted particle diameters less than 0.3 µm.

As previously described, these blowing agents will preferably be incorporated in an emulsified feed stock prior to spray drying. For the purposes of the present invention this feed stock will also preferably comprise one or more active or bioactive agents, one or more surfactants or one or more excipients. Of course, combinations of the aforementioned components are also within the scope of the invention. While high boiling (>100° C.) fluorinated blowing agents comprise one preferred aspect of the present invention, it will be appreciated that nonfluorinated blowing agents with similar boiling points (>100° C.) may be used to provide perforated microstructures. Exemplary nonfluorinated blowing agents suitable for use in the present invention comprise the formula:

$$R^1-X-R^2 \text{ or } R^1-X$$

wherein: $R^1$ or $R^2$ is hydrogen, alkyl, alkenyl, alkynl, aromatic, cyclic or combinations thereof, X is any group containing carbon, sulfur, nitrogen, halogens, phosphorus, oxygen and combinations thereof.

While not limiting the invention in any way it is hypothesized that, as the aqueous feed component evaporates during spray drying it leaves a thin crust at the surface of the particle. The resulting particle wall or crust formed during the initial moments of spray drying appears to trap any high boiling blowing agents as hundreds of emulsion droplets (ca. 200-

300 nm). As the drying process continues, the pressure inside the particulate increases thereby vaporizing at least part of the incorporated blowing agent and forcing it through the relatively thin crust. This venting or outgassing apparently leads to the formation of pores or other defects in the microstructure. At the same time remaining particulate components (possibly including some blowing agent) migrate from the interior to the surface as the particle solidifies. This migration apparently slows during the drying process as a result of increased resistance to mass transfer caused by an increased internal viscosity. Once the migration ceases the particle solidifies, leaving voids, pores, defects, hollows, spaces, interstitial spaces, apertures, perforations or holes. The number of pores or defects, their size, and the resulting wall thickness is largely dependent on the formulation and/or the nature of the selected blowing agent (e.g. boiling point), its concentration in the emulsion, total solids concentration, and the spray-drying conditions. It can be greatly appreciated that this type of particle morphology in part contributes to the improved powder dispersibility, suspension stability and aerodynamics.

It has been surprisingly found that substantial amounts of these relatively high boiling blowing agents may be retained in the resulting spray dried product. That is, spray dried perforated microstructures as described herein may comprise as much as 1%, 3%, 5%, 10%, 20%, 30% or even 40% w/w of the blowing agent. In such cases, higher production yields were obtained as a result an increased particle density caused by residual blowing agent. It will be appreciated by those skilled in the art that retained fluorinated blowing agent may alter the surface characteristics of the perforated microstructures, thereby minimizing particle aggregation during processing and further increasing dispersion stability. Residual fluorinated blowing agent in the particle may also reduce the cohesive forces between particles by providing a barrier or by attenuating the attractive forces produced during manufacturing (e.g., electrostatics). This reduction in cohesive forces may be particularly advantageous when using the disclosed microstructures in conjunction with dry powder inhalers.

Furthermore, the amount of residual blowing agent can be attenuated through the process conditions (such as outlet temperature), blowing agent concentration, or boiling point. If the outlet temperature is at or above the boiling point, the blowing agent escapes the particle and the production yield decreases. Preferred outlet temperature will generally be operated at 20, 30, 40, 50, 60, 70, 80, 90 or even 100° C. less than the blowing agent boiling point. More preferably the temperature differential between the outlet temperature and the boiling point will range from 50 to 150° C. It will be appreciated by those skilled in the art that particle porosity, production yield, electrostatics and dispersibility can be optimized by first identifying the range of process conditions (e.g., outlet temperature) that are suitable for the selected active agents and/or excipients. The preferred blowing agent can be then chosen using the maximum outlet temperature such that the temperature differential with be at least 20 and up to 150° C. In some cases, the temperature differential can be outside this range such as, for example, when producing the particulates under supercritical conditions or using lyophilization techniques. Those skilled in the art will further appreciate that the preferred concentration of blowing agent can be determined experimentally without undue experimentation using techniques similar to those described in the Examples herein.

While residual blowing agent may be advantageous in selected embodiments it may be desirable to substantially remove any blowing agent from the spray dried product. In this respect, the residual blowing agent can easily be removed with a post-production evaporation step in a vacuum oven. Moreover, such post production techniques may be used to provide perforations in the particulates. For example, pores may be formed by spray drying a bioactive agent and an excipient that can be removed from the formed particulates under a vacuum.

In any event, typical concentrations of blowing agent in the feed stock are between 2% and 50% v/v, and more preferably between about 10% to 45% v/v. In other embodiments blowing agent concentrations will preferably be greater than about 5%, 10%, 15%, 20%, 25% or even 30% v/v. Yet other feed stock emulsions may comprise 35%, 40%, 45% or even 50% v/v of the selected high boiling point compound.

In preferred embodiments, another method of identifying the concentration of blowing agent used in the feed is to provide it as a ratio of the concentration of the blowing agent to that of the stabilizing surfactant (e.g. phosphatidylcholine or PC) in the precursor or feed emulsion. For fluorocarbon blowing agents (e.g. perfluorooctyl bromide), and for the purposes of explanation, this ratio has been termed the PFC/PC ratio. More generally, it will be appreciated that compatible blowing agents and/or surfactants may be substituted for the exemplary compounds without falling outside of the scope of the present invention. In any event, the typical PFC/PC ratio will range from about 1 to about 60 and more preferably from about 10 to about 50. For preferred embodiments the ratio will generally be greater than about 5, 10, 20, 25, 30, 40 or even 50. In this respect, FIG. 1 shows a series of pictures taken of perforated microstructures formed of phosphatidylcholine (PC) using various amounts of perfluorooctyl bromide (PFC), a relatively high boiling point fluorocarbon as the blowing agent. The PFC/PC ratios are provided under each subset of pictures, i.e. from 1A to 1F. Formation and imaging conditions are discussed in greater detail in Examples I and II below. With regard to the micrographs, the column on the left shows the intact microstructures while the column on the right illustrates cross-sections of fractured microstructures from the same preparations.

As may easily be seen in the FIG. 1, the use of higher PFC/PC ratios provides structures of a more hollow and porous nature. More particularly, those methods employing a PFC/PC ratio of greater than about 4.8 tended to provide structures that are particularly compatible with the dry power formulations and dispersions disclosed herein. Similarly, FIG. 3, a micrograph which will be discussed in more detail in Example XII below, illustrates a preferably porous morphology obtained by using higher boiling point blowing agents (in this case perfluorodecalin).

While relatively high boiling point blowing agents comprise one preferred aspect of the instant invention, it will be appreciated that more conventional and unconventional blowing or inflating agents may also be used to provide compatible perforated microstructures. The blowing agent comprises any volatile substance, which can be incorporated into the feed solution for the purpose of producing a perforated foam-like structure in the resulting dry microspheres. The blowing agent may be removed during the initial drying process or during a post-production step such as vacuum drying or solvent extraction. Suitable agents include:

1. Dissolved low-boiling (below 100° C.) agents miscible with aqueous solutions, such as methylene chloride, acetone, ethyl acetate, and alcohols used to saturate the solution.
2. A gas, such as $CO_2$ or $N_2$, or liquid such as Freons, CFCs, HFAs, PFCs, HFCs, HFBs, fluoroalkanes, and hydrocarbons used at elevated pressure.

3. Emulsions of immiscible low-boiling (below 100° C.) liquids suitable for use with the present invention are generally of the formula:

$$R^1—X—R^2 \text{ or } R^1—X$$

wherein: $R^1$ or $R^2$ is hydrogen, alkyl, alkenyl, alkynl, aromatic, cyclic or combinations thereof, X is any groups containing carbon, sulfur, nitrogen, halogens, phosphorus, oxygen and combinations thereof. Such liquids include: Freons, CFCs, HFAs, PFCs, HFCs, HFBs, fluoroalkanes, and hydrocarbons.

4. Dissolved or dispersed salts or organic substances which can be removed under reduced pressure by sublimation in a post-production step, such as ammonium salts, camphor, etc.

5. Dispersed solids which can be extracted after the initial particle generation using a post-production solvent extraction step, such particles include latex, etc.

With respect to these lower boiling point inflating agents, they are typically added to the feed stock in quantities of about 1% to 40% v/v of the surfactant solution. Approximately 15% v/v inflating agent has been found to produce a spray dried powder that may be used to form the stabilized dispersions of the present invention.

Regardless of which blowing agent is ultimately selected, it has been found that compatible perforated microstructures may be produced particularly efficiently using a Büchi mini spray drier (model B-191, Switzerland). As will be appreciated by those skilled in the art, the inlet temperature and the outlet temperature of the spray drier are not critical but will be of such a level to provide the desired particle size and to result in a product that has the desired activity of the medicament. In this regard, the inlet and outlet temperatures are adjusted depending on the melting characteristics of the formulation components and the composition of the feed stock. The inlet temperature may thus be between 60° C. and 170° C., with the outlet temperatures of about 40° C. to 120° C. depending on the composition of the feed and the desired particulate characteristics. Preferably these temperatures will be from 90° C. to 120° C. for the inlet and from 60° C. to 90° C. for the outlet. The flow rate which is used in the spray drying equipment will generally be about 3 ml per minute to about 15 ml per minute. The atomizer air flow rate will vary between values of 25 liters per minute to about 50 liters per minute. Commercially available spray dryers are well known to those in the art, and suitable settings for any particular dispersion can be readily determined through standard empirical testing, with due reference to the examples that follow. Of course, the conditions may be adjusted so as to preserve biological activity in larger molecules such as proteins or peptides.

Though the perforated microstructures are preferably formed using fluorinated blowing agents in the form of an emulsion, it will be appreciated that nonfluorinated oils may be used to increase the loading capacity of active or bioactive agents without compromising the microstructure. In this case, selection of the nonfluorinated oil is based upon the solubility of the active or bioactive agent, water solubility, boiling point, and flash point. The active or bioactive agent will be dissolved in the oil and subsequently emulsified in the feed solution. Preferably the oil will have substantial solubilization capacity with respect to the selected agent, low water solubility (<$10^{-3}$ M), boiling point greater than water and a flash point greater than the drying outlet temperature. The addition of surfactants, and co-solvents to the nonfluorinated oil to increase the solubilization capacity is also within the scope of the present invention.

In particularly preferred embodiments nonfluorinated oils may be used to solubilize agents or bioactive agents that have limited solubility in aqueous compositions. The use of non-fluorinated oils is of particular use for increasing the loading capacity of steroids such as beclomethasone dipropionate and triamcinolone acetonide. Preferably the oil or oil mixture for solubilizing these clathrate forming steroids will have a refractive index between 1.36 and 1.41 (e.g. ethyl butyrate, butyl carbonate, dibutyl ether). In addition, process conditions, such as temperature and pressure, may be adjusted in order to boost solubility of the selected agent. It will be appreciated that selection of an appropriate oil or oil mixtures and processing conditions to maximize the loading capacity of an agent are well within the purview of a skilled artisan in view of the teachings herein and may be accomplished without undue experimentation.

Particularly preferred embodiments of the present invention comprise spray drying preparations comprising a surfactant such as a phospholipid and at least one active or bioactive agent. In other embodiments the spray drying preparation may further comprise an excipient comprising a hydrophilic moiety such as, for example, a carbohydrate (i.e. glucose, lactose, or starch) in addition to any selected surfactant. In this regard various starches and derivatized starches suitable for use in the present invention. Other optional components may include conventional viscosity modifiers, buffers such as phosphate buffers or other conventional biocompatible buffers or pH adjusting agents such as acids or bases, and osmotic agents (to provide isotonicity, hyperosmolarity, or hyposmolarity). Examples of suitable salts include sodium phosphate (both monobasic and dibasic), sodium chloride, calcium phosphate, calcium chloride and other physiologically acceptable salts.

Whatever components are selected, the first step in particulate production typically comprises feed stock preparation. Preferably the selected drug is dissolved in water to produce a concentrated solution. The drug may also be dispersed directly in the emulsion, particularly in the case of water insoluble agents. Alternatively, the drug may be incorporated in the form of a solid particulate dispersion. The concentration of the active or bioactive agent used is dependent on the amount of agent required in the final powder and the performance of the delivery device employed (e.g., the fine particle dose for a MDI or DPI). As needed, cosurfactants such as poloxamer 188 or span 80 may be dispersed into this annex solution. Additionally, excipients such as sugars and starches can also be added.

In selected embodiments an oil-in-water emulsion is then formed in a separate vessel. The oil employed is preferably a fluorocarbon (e.g., perfluorooctyl bromide, perfluorodecalin) which is emulsified using a surfactant such as a long chain saturated phospholipid. For example, one gram of phospholipid may be homogenized in 150 g hot distilled water (e.g., 60° C.) using a suitable high shear mechanical mixer (e.g., Ultra-Turrax model T-25 mixer) at 8000 rpm for 2 to 5 minutes. Typically 5 to 25 g of fluorocarbon is added dropwise to the dispersed surfactant solution while mixing. The resulting perfluorocarbon in water emulsion is then processed using a high pressure homogenizer to reduce the particle size. Typically the emulsion is processed at 12,000 to 18,000 psi, 5 discrete passes and kept at 50 to 80° C.

The active or bioactive agent solution and perfluorocarbon emulsion are then combined and fed into the spray dryer. Typically the two preparations will be miscible as the emulsion will preferably comprise an aqueous continuous phase. While the bioactive agent is solubilized separately for the purposes of the instant discussion it will be appreciated that, in other embodiments, the active or bioactive agent may be solubilized (or dispersed) directly in the emulsion. In such cases, the active or bioactive emulsion is simply spray dried without combining a separate drug preparation.

In any event, operating conditions such as inlet and outlet temperature, feed rate, atomization pressure, flow rate of the drying air, and nozzle configuration can be adjusted in accordance with the manufacturer's guidelines in order to produce the required particle size, and production yield of the resulting dry microstructures. Exemplary settings are as follows: an air inlet temperature between 60° C. and 170° C.; an air outlet between 40° C. to 120° C.; a feed rate between 3 ml to about 15 ml per minute; and an aspiration air flow of 300 L/min. and an atomization air flow rate between 25 to 50 L/min. The selection of appropriate apparatus and processing conditions are well within the purview of a skilled artisan in view of the teachings herein and may be accomplished without undue experimentation. In any event, the use of these and substantially equivalent methods provide for the formation of hollow porous aerodynamically light microspheres with particle diameters appropriate for aerosol deposition into the lung. microstructures that are both hollow and porous, almost honeycombed or foam-like in appearance. In especially preferred embodiments the perforated microstructures comprise hollow, porous spray dried microspheres.

Along with spray drying, perforated microstructures useful in the present invention may be formed by lyophilization. Those skilled in the art will appreciate that lyophilization is a freeze-drying process in which water is sublimed from the composition after it is frozen. The particular advantage associated with the lyophilization process is that biologicals and pharmaceuticals that are relatively unstable in an aqueous solution can be dried without elevated temperatures (thereby eliminating the adverse thermal effects), and then stored in a dry state where there are few stability problems. With respect to the instant invention such techniques are particularly compatible with the incorporation of peptides, proteins, genetic material and other natural and synthetic macromolecules in particulates or perforated microstructures without compromising physiological activity. Methods for providing lyophilized particulates are known to those of skill in the art and it would clearly not require undue experimentation to provide dispersion compatible microstructures in accordance with the teachings herein. The lyophilized cake containing a fine foam-like structure can be micronized using techniques known in the art to provide 3 to 10 µm sized particles. Accordingly, to the extent that lyophilization processes may be used to provide microstructures having the desired porosity and size they are conformance with the teachings herein and are expressly contemplated as being within the scope of the instant invention.

Besides the aforementioned techniques, the perforated microstructures or particles of the present invention may also be formed using a method where a feed solution (either emulsion or aqueous) containing wall forming agents is rapidly added to a reservoir of heated oil (e.g. perflubron or other high boiling FCs) under reduced pressure. The water and volatile solvents of the feed solution rapidly boils and are evaporated. This process provides a perforated structure from the wall forming agents similar to puffed rice or popcorn. Preferably the wall forming agents are insoluble in the heated oil. The resulting particles can then separated from the heated oil using a filtering technique and subsequently dried under vacuum.

Additionally, the perforated microstructures of the present invention may also be formed using a double emulsion method. In the double emulsion method the medicament is first dispersed in a polymer dissolved in an organic solvent (e.g. methylene chloride) by sonication or homogenization. This primary emulsion is then stabilized by forming a multiple emulsion in a continuous aqueous phase containing an emulsifier such as polyvinylalcohol. Evaporation or extraction using conventional techniques and apparatus then removes the organic solvent. The resulting microspheres are washed, filtered and dried prior to combining them with an appropriate suspension medium in accordance with the present invention Whatever production method is ultimately selected for production of the perforated microstructures, the resulting powders have a number of advantageous properties that make them particularly compatible for use in devices for inhalation therapies. In particular, the physical characteristics of the perforated microstructures make them extremely effective for use in dry powder inhalers and in the formation of stabilized dispersions that may be used in conjunction with metered dose inhalers, nebulizers and liquid dose instillation. As such, the perforated microstructures provide for the effective pulmonary administration of bioactive agents.

In order to maximize dispersibility, dispersion stability and optimize distribution upon administration, the mean geometric particle size of the perforated microstructures is preferably about 0.5-50 µm, more preferably 1-30 µm. It will be appreciated that large particles (i.e. greater than 50 µm) may not be preferred in applications where a valve or small orifice is employed, since large particles tend to aggregate or separate from a suspension which could potentially clog the device. In especially preferred embodiments the mean geometric particle size (or diameter) of the perforated microstructures is less than 20 µm or less than 10 µm. More preferably the mean geometric diameter is less than about 7 µm or 5 µm, and even more preferably less than about 2.5 µm. Other preferred embodiments will comprise preparations wherein the mean geometric diameter of the perforated microstructures is between about 1 µm and 5 µm. In especially preferred embodiments the perforated microstructures will comprise a powder of dry, hollow, porous microspherical shells of approximately 1 to 10 µm or 1 to 5 µm in diameter, with shell thicknesses of approximately 0.1 µm to approximately 0.5 µm. It is a particular advantage of the present invention that the particulate concentration of the dispersions and structural matrix components can be adjusted to optimize the delivery characteristics of the selected particle size.

As alluded to throughout the instant specification the porosity of the microstructures may play a significant part is establishing dispersibility (e.g. in DPIs) or dispersion stability (e.g. for MDIs or nebulizers). In this respect, the mean porosity of the perforated microstructures may be determined through electron microscopy coupled with modern imaging techniques. More specifically, electron micrographs of representative samples of the perforated microstructures may be obtained and digitally analyzed to quantify the porosity of the preparation. Such methodology is well known in the art and may be undertaken without undue experimentation.

For the purposes of the present invention, the mean porosity (i.e. the percentage of the particle surface area that is open to the interior and/or a central void) of the perforated microstructures may range from approximately 0.5% to approximately 80%. In more preferred embodiments, the mean porosity will range from approximately 2% to approximately 40%. Based on selected production parameters, the mean porosity may be greater than approximately, 2%, 5%, 10%, 15%, 20%, 25% or 30% of the microstructure surface area. In other embodiments, the mean porosity of the microstructures may be greater than about 40%, 50%, 60%, 70% or even 80%.

As to the pores themselves, they typically range in size from about 5 nm to about 400 nm with mean pore sizes preferably in the range of from about 20 nm to about 200 nm. In particularly preferred embodiments the mean pore size will be in the range of from about 50 nm to about 100 nm. As may be seen in FIGS. 1A1 to 1F2 and discussed in more detail below, it is a significant advantage of the present invention that the pore size and porosity may be closely controlled by careful selection of the incorporated components and production parameters.

In this regard, the particle morphology and/or hollow design of the perforated microstructures also plays an important role on the dispersibility or cohesiveness of the dry powder formulations disclosed herein. That is, it has been surprisingly discovered that the inherent cohesive character of fine powders can be overcome by lowering the van der Waals, electrostatic attractive and liquid bridging forces that typically exist between dry particles. More specifically, in concordance with the teachings herein, improved powder dispersibility may be provided by engineering the particle morphology and density, as well as control of humidity and charge. To that end, the perforated microstructures of the present invention comprise pores, voids, hollows, defects or other interstitial spaces which reduce the surface contact area between particles thereby minimizing interparticle forces. In addition, the use of surfactants such as phospholipids and fluorinated blowing agents in accordance with the teachings herein may contribute to improvements in the flow properties of the powders by tempering the charge and strength of the electrostatic forces as well as moisture content.

Most fine powders (e.g. <5 μm) exhibit poor dispersibility which can be problematic when attempting to deliver, aerosolize and/or package the powders. In this respect the major forces which control particle interactions can typically be divided into long and short range forces. Long range forces include gravitational attractive forces and electrostatics, where the interaction varies as a square of the separation distance or particle diameter. Important short range forces for dry powders include van der Waals interactions, hydrogen bonding and liquid bridges. The latter two short range forces differ from the others in that they occur where there is already contact between particles. It is a major advantage of the present invention that these attractive forces may be substantially attenuated or reduced through the use of perforated microstructures as described herein.

In an effort to overcome these attractive forces, typical prior art dry powder formulations for DPIs comprise micronized drug particles that are deposited on large carrier particles (e.g., 30 to 90 μm) such as lactose or agglomerated units of pure drug particles or agglomeration of fine lactose particles with pure drug, since they are more readily fluidized than neat drug particles. In addition, the mass of drug required per actuation is typically less than 100 μg and is thus prohibitively too small to meter. Hence, the larger lactose particles in prior art formulations function as both a carrier particle for aerosolization and a bulking agent for metering. The use of large particles in these formulations are employed since powder dispersibility and aerosolization efficiency improves with increasing increasing particle size as a result of diminished interparticle forces (French, D. L., Edwards, D. A., sand Niven, R. W., J. Aerosol Sci. 27, 769-783, 1996 which is incorporated herein by reference). That is, prior art formulations often use large particles or carriers to overcome the principle forces controlling dispersibility such as van der Waals forces, liquid bridging, and electrostatic attractive forces that exists between particles.

Those skilled in the art will appreciate that the van der Waals (VDW) attractive force occurs at short range and depends, at least in part, on the surface contact between the interacting particles. When two dry particles approach each other the VDW forces increase with an increase in contact area. For two dry particles, the magnitude of the VDW interaction force, $F^0_{vdw}$, can be calculated using the following equation:

$$F^0_{vdw} = \frac{\hbar\omega}{8\pi d_0^2}\left[\frac{r_1 r_2}{r_1 + r_2}\right]$$

where h is Planck's constant, $\overline{\omega}$ is the angular frequency, $d_0$ is the distance at which the adhesional force is at a maximum, and $r_1$ and $r_2$ are the radii of the two interacting particles. Accordingly, it will be appreciated that one way to minimize the magnitude and strength of the VDW force for dry powders is to decrease the interparticle area of contact. It is important to note that the magnitude $d_0$ is a reflection of this area of contact. The minimal area of contact between two opposing bodies will occur if the particles are perfect spheres. In addition, the area of contact will be further minimized if the particles are highly porous. Accordingly, the perforated microstructures of the present invention act to reduce interparticle contact and corresponding VDW attractive forces. It is important to note that this reduction in VDW forces is largely a result of the unique particle morphology of the powders of the present invention rather than an increase in geometric particle diameter. In this regard, it will be appreciated that particularly preferred embodiments of the present invention provide powders having average or small particulates (e.g. mean geometric diameter <10 μm) exhibiting relatively low VDW attractive forces. Conversely, solid, non-spherical particles such as conventional micronized drugs of the same size will exert greater interparticle forces between them and, hence, will exhibit poor powder dispersibility.

Further, as indicated above, the electrostatic force affecting powders occurs when either or both of the particles are electrically charged. This phenomenon will result with either an attraction or repulsion between particles depending on the similarity or dissimilarity of charge. In the simplest case, the electric charges can be described using Coulomb's Law. One way to modulate or decrease the electrostatic forces between particles is if either or both particles have non-conducting surfaces. Thus, if the perforated microstructure powders comprise excipients, surfactants or active agents that are relatively non-conducting, then any charge generated in the particle will be unevenly distributed over the surface. As a result, the charge half-life of powders comprising non-conducting components will be relatively short since the retention of elevated charges is dictated by the resistivity of the material. Resistive or non-conducting components are materials which will neither function as an efficient electron donor or acceptor.

Derjaguin et al. (Muller, V. M., Yushchenko, V. S., and Derjaguin, B. V., J. Colloid Interface Sci. 1980, 77, 115-119), which is incorporated herein by reference, provide a list ranking molecular groups for their ability to accept or donate an electron. In this regard exemplary groups may be ranked as follows:

Donor: $—NH_2$>—OH>—OR>—COOR>$—CH_3$>
$—C_6H_5$>-halogen>—COOH>—CO>—CN
Acceptor:

The present invention provides for the reduction of electrostatic effects in the disclosed powders though the use of relatively non-conductive materials. Using the above rankings, preferred non-conductive materials would include halogenated and/or hydrogenated components. Materials such as phospholipids and fluorinated blowing agents (which may be retained to some extent in the spray dried powders) are preferred since they can provide resistance to particle charging. It will be appreciated that the retention of residual blowing agent (e.g. fluorochemicals) in the particles, even at relatively low levels, may help minimize charging of the perforated microstructures as is typically imparted during spray drying and cyclone separation. Based on general electrostatic principles and the teachings herein, one skilled in the art would be able to identify additional materials that serve to reduce the electrostatic forces of the disclosed powders without undue experimentation. Further, if needed, the electrostatic forces can also be manipulated and minimized using electrification and charging techniques.

In addition to the surprising advantages described above, the present invention further provides for the attenuation or reduction of hydrogen and liquid bonding. As known to those skilled in the art, both hydrogen bonding and liquid bridging can result from moisture that is absorbed by the powder. In general, higher humidities produce higher interparticle forces for hydrophilic surfaces. This is a substantial problem in prior art pharmaceutical formulations for inhalation therapies which tend to employ relatively hydrophilic compounds such as lactose. However, in accordance with the teachings herein, adhesion forces due to adsorbed water can be modulated or reduced by increasing the hydrophobicity of the contacting surfaces. One skilled in the art can appreciate that an increase in particle hydrophobicity can be achieved through excipient selection and/or use a post-production spray drying coating technique such as employed using a fluidized bed. Thus, preferred excipients include hydrophobic surfactants such as phospholipids, fatty acid soaps and cholesterol. In view of the teachings herein, it is submitted that a skilled artisan would be able to identify materials exhibiting similar desirable properties without undue experimentation.

In accordance with the present invention, methods such as angle of repose or shear index can be used to assess the flow properties of dry powders. The angle of repose is defined as the angle formed when a cone of powder is poured onto a flat surface. Powders having an angle of repose ranging from 45° to 20° are preferred and indicate suitable powder flow. More particularly, powders which possess an angle of repose between 33° and 20° exhibit relatively low shear forces and are especially useful in pharmaceutical preparations for use in inhalation therapies (e.g. DPIs). The shear index, though more time consuming to measure than angle of repose, is considered more reliable and easy to determine. Those skilled in the art will appreciate that the experimental procedure outlined by Amidon and Houghton (G. E. Amidon, and M. E. Houghton, Pharm. Manuf., 2, 20, 1985, incorporated herein by reference) can be used estimate the shear index for the purposes of the present invention. As described in S. Kocova and N. Pilpel, J. Pharm. Pharmacol. 8, 33-55, 1973, also incorporated herein by reference, the shear index is estimated from powder parameters such as, yield stress, effective angle of internal friction, tensile strength, and specific cohesion. In the present invention powders having a shear index less than about 0.98 are desirable. More preferably, powders used in the disclosed compositions, methods and systems will have shear indices less than about 1.1. In particularly preferred embodiments the shear index will be less than about 1.3 or even less than about 1.5. Of course powders having different shear indices may be used provided the result in the effective deposition of the active or bioactive agent at the site of interest.

It will also be appreciated that the flow properties of powders have been shown correlate well with bulk density measurements. In this regard, conventional prior art thinking (C. F. Harwood, J. Pharm. Sci., 60, 161-163, 1971) held that an increase in bulk density correlates with improved flow properties as predicted by the shear index of the material. Conversely, it has surprisingly been found that, for the perforated microstructures of the present invention, superior flow properties were exhibited by powders having relatively low bulk densities. That is, the hollow porous powders of the present invention exhibited superior flow properties over powders substantially devoid of pores. To that end, it has been found that it is possible to provide powders having bulk densities of less than 0.5 g/cm$^3$ that exhibit particularly favorable flow properties. More surprisingly, it has been found that it is possible to provide perforated microstructure powders having bulk densities of less than 0.3 g/cm$^3$ or even less than about 0.1 g/cm$^3$ that exhibit excellent flow properties. The ability to produce low bulk density powders having superior flowability further accentuates the novel and unexpected nature of the present invention.

In addition, it will be appreciated that the reduced attractive forces (e.g. van der Waals, electrostatic, hydrogen and liquid bonding, etc.) and excellent flowability provided by the perforated microstructure powders make them particularly useful in preparations for inhalation therapies (e.g. in inhalation devices such as DPIs, MDIs, nebulizers). Along with the superior flowability, the perforated or porous and/or hollow design of the microstructures also plays an important role in the resulting aerosol properties of the powder when discharged. This phenomenon holds true for perforated microstructures aerosolized as a suspension, as in the case of an MDI or a nebulizer, or delivery of perforated microstructures in dry form as in the case of a DPI. In this respect the perforated structure and relatively high surface area of the dispersed microparticles enables them to be carried along in the flow of gases during inhalation with greater ease for longer distances than non-perforated particles of comparable size.

More particularly, because of their high porosity, the density of the particles is significantly less than 1.0 g/cm$^3$, typically less than 0.5 g/cm$^3$, more often on the order of 0.1 g/cm$^3$, and as low as 0.01 g/cm$^3$. Unlike the geometric particle size, the aerodynamic particle size, $d_{aer}$, of the perforated microstructures depends substantially on the particle density, $\rho: d_{aer} = d_{geo}\rho$, where $d_{geo}$ is the geometric diameter. For a particle density of 0.1 g/cm$^3$, $d_{aer}$ will be roughly three times smaller than $d_{geo}$, leading to increased particle deposition into the peripheral regions of the lung and correspondingly less deposition in the throat. In this regard, the mean aerodynamic diameter of the perforated microstructures is preferably less than about 5 μm, more preferably less than about 3 μm, and, in particularly preferred embodiments, less than about 2 μm. Such particle distributions will act to increase the deep lung deposition of the bioactive agent whether administered using a DPI, MDI or nebulizer. Further, having a larger geometric diameter than aerodynamic diameter brings the particles closer to the wall of the alveolus thus increasing the deposition of small aerodynamic diameter particles.

As will be shown subsequently in the Examples, the particle size distribution of the aerosol formulations of the present invention are measurable by conventional techniques such as, for example, cascade impaction or by time of flight analytical methods. In addition, determination of the emitted dose from inhalation devices were done according to the proposed U.S. Pharmacopeia method (*Pharmacopeial Previews*, 22(1996) 3065) which is incorporated herein by reference. These and related techniques enable the "fine particle fraction" of the aerosol, which corresponds to those particulates that are likely to effectively deposited in the lung, to be calculated. As used herein the phrase "fine particle fraction" refers to the percentage of the total amount of active medicament delivered per actuation from the mouthpiece of a DPI, MDI or nebulizer onto plates 2-7 of an 8 stage Andersen cascade impactor. Based on such measurements the formulations of the present invention will preferably have a fine particle fraction of approximately 20% or more by weight of the perforated microstructures (w/w), more preferably they will exhibit a fine particle fraction of from about 25% to 80% w/w, and even more preferably from about 30 to 70% w/w. In selected embodiments the present invention will preferably comprise a fine particle fraction of greater than about 30%, 40%, 50%, 60%, 70% or 80% by weight.

Further, it has also been found that the formulations of the present invention exhibit relatively low deposition rates, when compared with prior art preparations, on the induction port and onto plates 0 and 1 of the impactor. Deposition on these components is linked with deposition in the throat in humans. More specifically, most commercially available MDIs and DPIs have simulated throat depositions of approximately 40-70% (w/w) of the total dose, while the formulations of the present invention typically deposit less than about 20% w/w. Accordingly, preferred embodiments of the present invention have simulated throat depositions of less than about 40%, 35%, 30%, 25%, 20%, 15% or even 10% w/w. Those skilled in the art will appreciate that significant decrease in throat deposition provided by the present invention will result in a corresponding decrease in associated local side-effects such as throat irritation and candidiasis.

With respect to the advantageous deposition profile provided by the instant invention it is well known that MDI propellants typically force suspended particles out of the device at a high velocity towards the back of the throat. Since prior art formulations typically contain a significant percentage of large particles and/or aggregates, as much as two-thirds or more of the emitted dose may impact the throat. Moreover, the undesirable delivery profile of conventional powder preparations is also exhibited under conditions of low particle velocity, as occurs with DPI devices. In general, this problem is inherent when aerosolizing solid, dense, particulates which are subject to aggregation. Yet, as discussed above, the novel and unexpected properties of the stabilized dispersions of the present invention result in surprisingly low throat deposition upon administration from inhalation device such as a DPI, MDI atomizer or nebulizer.

While not wishing to be bound by any particular theory, it appears that the reduced throat deposition provided by the instant invention results from decreases in particle aggregation and from the hollow and/or porous morphology of the incorporated microstructures. That is, the hollow and porous nature of the dispersed microstructures slows the velocity of particles in the propellant stream (or gas stream in the case of DPIs), just as a hollow/porous whiffle ball decelerates faster than a baseball. Thus, rather than impacting and sticking to the back of the throat, the relatively slow traveling particles are subject to inhalation by the patient. Moreover, the highly porous nature of the particles allows th propellant within the perforated microstructure to rapidly leave and the particle density to drop before impacting the throat. Accordingly, a substantially higher percentage of the administered bioactive agent is deposited in the pulmonary air passages where it may be efficiently absorbed.

With respect to inhalation therapies, those skilled in the art will appreciate that the perforated microstructure powders of the present invention are particularly useful in DPIs. Conventional DPIs, or dry powder inhalers, comprise powdered formulations and devices where a predetermined dose of medicament, either alone or in a blend with lactose carrier particles, is delivered as a fine mist or aerosol of dry powder for inhalation. The medicament is formulated in a way such that it readily disperses into discrete particles with a size rage between 0.5 to 20 µm. The powder is actuated either by inspiration or by some external delivery force, such as pressurized air. DPI formulations are typically packaged in single dose units or they employ reservoir systems capable of metering multiple doses with manual transfer of the dose to the device.

DPIs are generally classified based on the dose delivery system employed. In this respect, the two major types of DPIs comprise unit dose delivery devices and bulk reservoir delivery systems. As used herein, the term "reservoir" shall be used in a general sense and held to encompass both configurations unless otherwise dictated by contextual restraints. In any event, unit dose delivery systems require the dose of powder formulation presented to the device as a single unit. With this system, the formulation is prefilled into dosing wells which may be foil-packaged or presented in blister strips to prevent moisture ingress. Other unit dose packages include hard gelatin capsules. Most unit dose containers designed for DPIs are filled using a fixed volume technique. As a result, there are physical limitations (here density) to the minimal dose that can be metered into a unit package, which is dictated by the powder flowability and bulk density. Currently, the range of dry powder that can be filled into a unit dose container is in the range of 5 to 15 mg which corresponds to drug loading in the range of 25 to 500 µg per dose. Conversely, bulk reservoir delivery systems provide a precise quantity of powder to be metered upon individual delivery for up to approximately 200 doses. Again like the unit dose systems, the powder is metered using a fixed volume cell or chamber that the powder is filled into. Thus, the density of the powder is a major factor limiting the minimal dose that can be delivered with this device. Currently bulk reservoir type DPIs can meter between 200 µg to 20 mg powder per actuation.

DPIs are designed to be manipulated such that they break open the capsule/blister or to load bulk powder during actuation, followed by dispersion from a mouthpiece or actuator due to the patient's inspiration. When the prior art formulations are actuated from a DPI device the lactose/drug aggregates are aerosolized and the patient inhales the mist of dry powder. During the inhalation process, the carrier particles encounter shear forces whereby some of the micronized drug particles are separated from the lactose particulate surface. It will be appreciated that the drug particles are subsequently carried into the lung. The large lactose particles impact the throat and upper airways due to size and inertial force constraints. The efficiency of delivery of the drug particles is dictated by their degree of adhesion with the carrier particles and their aerodynamic property.

Deaggregation can be increased through formulation, process and device design improvements. For example fine particle lactose (FPL) is often mixed with coarse lactose carriers, wherein the FPL will occupy high-energy binding sites on the carrier particles. This process provides more passive sites for adhesion of the micronized drug particles. This tertiary blend with the drug has been shown to provide statistically significant increases in fine particle fraction. Other strategies include specialized process conditions where drug particles are mixed with FPL to produce agglomerated units. In order to further increase particulate deposition, many DPIs are designed to provide deaggregation by passing the dosage form over baffles, or through tortuous channels that disrupts the flow properties.

The addition of FPL, agglomeration with FPL and specialized device design provides an improvement in the deaggregation of formulations, however, the clinically important parameter is the fine particle dose received by the patient. Though improvements in deaggregation can be provided, a major problem still exists with current DPI devices in that there is an increase in respirable dose with an increased inspiratory effort. This is a result of an increased fine particle fraction corresponding to the increased disaggregation of particle agglomerates as the airflow increases through the inhaler with increasing inspiratory effort. Consequently dosing accuracy is compromised, leading to complications when the devices are used to administer highly efficacious drugs to sensitive populations such as children, adolescents and the elderly. Moreover, the dosing inaccuracy associated with conventional preparations could complicate regulatory approval.

In stark contrast, the perforated microstructure powders of the present invention obviate many of the difficulties associated with prior art carrier preparations. That is, an improvement in DPI performance may be provided by engineering the particle, size, aerodynamics, morphology and density, as well as control of humidity and charge. In this respect the present invention provides formulations wherein the medicament and the incipients or bulking agents are preferably associated with or comprise the perforated microstructures. As set forth above, preferred compositions according to the present invention typically yield powders with bulk densities less than 0.1 g/cm$^3$ and often less than 0.05 g/cm$^3$. It will be appreciated that providing powders having bulk densities an order of a magnitude less than conventional DPI formulations allows for much lower doses of the selected bioactive agent to be filled into a unit dose container or metered via reservoir-based DPIs. The ability to effectively meter small quantities is of particular importance for low dose steroid, long acting bronchodilators and new protein or peptide medicaments proposed for DPI delivery. Moreover, the ability to effectively deliver particulates without associated carrier particles simplifies product formulation, filling and reduces undesirable side effects.

As discussed above, the hollow porous powders of the present invention exhibit superior flow properties, as measured by the angle of repose or shear index methods described herein, with respect to equivalent powders substantially devoid of pores. That is, superior powder flow, which appears to be a function of bulk density and particle morphology, is observed where the powders have a bulk density less than 0.5 g/cm$^3$. Preferably the powders have bulk densities of less than about 0.3 g/cm$^3$, 0.1 g/cm$^3$ or even less than about 0.05 g/cm$^3$. In this regard, it is theorized that the perforated microstructures comprising pores, voids, hollows, defects or other interstitial spaces contribute to powder flow properties by reducing the surface contact area between particles and minimizing interparticle forces. In addition, the use of phospholipids in preferred embodiments and retention of fluorinated blowing agents may also contribute to improvements in the flow properties of the powders by tempering the charge and strength of the electrostatic forces as well as moisture content.

In addition to the aforementioned advantages, the disclosed powders exhibit favorable aerodynamic properties that make them particularly effective for use in DPIs. More specifically, the perforated structure and relatively high surface area of the microparticles enables them to be carried along in the flow of gases during inhalation with greater ease and for longer distances than relatively non-perforated particles of comparable size. Because of their high porosity and low density, administration of the perforated microstructures with a DPI provides for increased particle deposition into the peripheral regions of the lung and correspondingly less deposition in the throat. Such particle distribution acts to increase the deep lung deposition of the administered agent which is preferable for systemic administration. Moreover, in a substantial improvement over prior art DPI preparations the low-density, highly porous powders of the present invention preferably eliminate the need for carrier particles. Since the large lactose carrier particles will impact the throat and upper airways due to their size, the elimination of such particles minimizes throat deposition and any associated "gag" effect associated with conventional DPIs.

Along with their use in a dry powder configuration, it will be appreciated that the perforated microstructures of the present invention may be incorporated in a suspension medium to provide stabilized dispersions. Among other uses, the stabilized dispersions provide for the effective delivery of bioactive agents to the pulmonary air passages of a patient using MDIs, nebulizers or liquid dose instillation (LDI techniques).

As with the DPI embodiments, Administration of a bioactive agent using an MDI, nebulizer or LDI technique may be indicated for the treatment of mild, moderate or severe, acute or chronic symptoms or for prophylactic treatment. Moreover, the bioactive agent may be administered to treat local or systemic conditions or disorders. It will be appreciated that, the precise dose administered will depend on the age and condition of the patient, the particular medicament used and the frequency of administration, and will ultimately be at the discretion of the attendant physician. When combinations of bioactive agents are employed, the dose of each component of the combination will generally be that employed for each component when used alone.

Those skilled in the art will appreciate the enhanced stability of the disclosed dispersions or suspensions is largely achieved by lowering the van der Waals attractive forces between the suspended particles, and by reducing the differences in density between the suspension medium and the particles. In accordance with the teachings herein, the increases in suspension stability may be imparted by engineering perforated microstructures which are then dispersed in a compatible suspension medium. As discussed above, the perforated microstructures comprise pores, voids, hollows, defects or other interstitial spaces that allow the fluid suspension medium to freely permeate or perfuse the particulate boundary. Particularly preferred embodiments comprise perforated microstructures that are both hollow and porous, almost honeycombed or foam-like in appearance. In especially preferred embodiments the perforated microstructures comprise hollow, porous spray dried microspheres.

When the perforated microstructures are placed in the suspension medium (i.e. propellant), the suspension medium is able to permeate the particles, thereby creating a "homodispersion", wherein both the continuous and dispersed phases are indistinguishable. Since the defined or "virtual" particles (i.e. comprising the volume circumscribed by the microparticulate matrix) are made up almost entirely of the medium in which they are suspended, the forces driving particle aggregation (flocculation) are minimized. Additionally, the differences in density between the defined particles and the continuous phase are minimized by having the microstructures filled with the medium, thereby effectively slowing particle creaming or sedimentation. As such, the perforated microspheres and stabilized suspensions of the present invention are particularly compatible with many aerosolization techniques, such as MDI and nebulization. Moreover, the stabilized dispersions may be used in liquid dose instillation applications.

Typical prior art suspensions (e.g. for MDIs) comprise mostly solid particles and small amounts (<1% w/w) of surfactant (e.g. lecithin, Span-85, oleic acid) to increase electrostatic repulsion between particles or polymers to sterically decrease particle interaction. In sharp contrast, the suspensions of the present invention are designed not to increase repulsion between particles, but rather to decrease the attractive forces between particles. The principal forces driving flocculation in nonaqueous media are van der Waals attractive forces. As discussed above, VDW forces are quantum mechanical in origin, and can be visualized as attractions between fluctuating dipoles (i.e. induced dipole-induced dipole interactions). Dispersion forces are extremely short-range and scale as the sixth power of the distance between atoms. When two macroscopic bodies approach one another the dispersion attractions between the atoms sums up. The resulting force is of considerably longer range, and depends on the geometry of the interacting bodies.

More specifically, for two spherical particles, the magnitude of the VDW potential, $V_A$, can be approximated by:

$$V_A = \frac{-A_{eff}}{6H_0}\frac{R_1R_2}{(R_1+R_2)},$$

where $A_{eff}$ is the effective Hamaker constant which accounts for the nature of the particles and the medium, $H_0$ is the distance between particles, and $R_1$ and $R_2$ are the radii of spherical particles 1 and 2. The effective Hamaker constant is proportional to the difference in the polarizabilities of the dispersed particles and the suspension medium:

$$A_{eff} = \left(\sqrt{A_{SM}} - \sqrt{A_{PART}}\right)^2,$$

where $A_{SM}$ and $A_{PART}$ are the Hamaker constants for the suspension medium and the particles, respectively. As the suspended particles and the dispersion medium become similar in nature, $A_{SM}$ and $A_{PART}$ become closer in magnitude, and $A_{eff}$ and $V_A$ become smaller. That is, by reducing the differences between the Hamaker constant associated with suspension medium and the Hamaker constant associated with the dispersed particles, the effective Hamaker constant (and corresponding van der Waals attractive forces) may be reduced.

One way to minimize the differences in the Hamaker constants is to create a "homodispersion", that is make both the continuous and dispersed phases essentially indistinguishable as discussed above. Besides exploiting the morphology of the particles to reduce the effective Hamaker constant, the components of the structural matrix (defining the perforated microstructures) will preferably be chosen so as to exhibit a Hamaker constant relatively close to that of the selected suspension medium. In this respect, one may use the actual values of the Hamaker constants of the suspension medium and the particulate components to determine the compatibility of the dispersion ingredients and provide a good indication as to the stability of the preparation. Alternatively, one could select relatively compatible perforated microstructure components and suspension mediums using characteristic physical values that coincide with measurable Hamaker constants but are more readily discernible.

In this respect, it has been found that the refractive index values of many compounds tend to scale with the corresponding Hamaker constant. Accordingly, easily measurable refractive index values may be used to provide a fairly good indication as to which combination of suspension medium and particle excipients will provide a dispersion having a relatively low effective Hamaker constant and associated stability. It will be appreciated that, since refractive indices of compounds are widely available or easily derived, the use of such values allows for the formation of stabilized dispersions in accordance with the present invention without undue experimentation. For the purpose of illustration only, the refractive indices of several compounds compatible with the disclosed dispersions are provided in Table I immediately below:

TABLE I

| Compound | Refractive Index |
|---|---|
| HFA-134a | 1.172 |
| HFA-227 | 1.223 |
| CFC-12 | 1.287 |
| CFC-114 | 1.288 |
| PFOB | 1.305 |
| Mannitol | 1.333 |
| Ethanol | 1.361 |
| n-octane | 1.397 |
| DMPC | 1.43 |
| Pluronic F-68 | 1.43 |
| Sucrose | 1.538 |
| Hydroxyethylstarch | 1.54 |
| Sodium chloride | 1.544 |

Consistent with the compatible dispersion components set forth above, those skilled in the art will appreciate that, the formation of dispersions wherein the components have a refractive index differential of less than about 0.5 is preferred. That is, the refractive index of the suspension medium will preferably be within about 0.5 of the refractive index associated with the perforated particles or microstructures. It will further be appreciated that, the refractive index of the suspension medium and the particles may be measured directly or approximated using the refractive indices of the major component in each respective phase. For the perforated microstructures, the major component may be determined on a weight percent basis. For the suspension medium, the major component will typically be derived on a volume percentage basis. In selected embodiments of the present invention the refractive index differential value will preferably be less than about 0.45, about 0.4, about 0.35 or even less than about 0.3. Given that lower refractive index differentials imply greater dispersion stability, particularly preferred embodiments comprise index differentials of less than about 0.28, about 0.25, about 0.2, about 0.15 or even less than about 0.1. It is submitted that a skilled artisan will be able to determine which excipients are particularly compatible without undue experimentation given the instant disclosure. The ultimate choice of preferred excipients will also be influenced by other factors, including biocompatibility, regulatory status, ease of manufacture, cost.

As discussed above, the minimization of density differences between the particles and the continuous phase is largely dependent on the perforated and/or hollow nature of the microstructures, such that the suspension medium constitutes most of the particle volume. As used herein, the term "particle volume" corresponds to the volume of suspension medium that would be displaced by the incorporated hollow/porous particles if they were solid, i.e. the volume defined by the particle boundary. For the purposes of explanation, and as discussed above, these fluid filled particulate volumes may be referred to as "virtual particles." Preferably, the average volume of the bioactive agent/excipient shell or matrix (i.e. the volume of medium actually displaced by the perforated microstructure) comprises less than 70% of the average particle volume (or less than 70% of the virtual particle). More preferably, the volume of the microparticulate matrix comprises less than about 50%, 40%, 30% or even 20% of the average particle volume. Even more preferably, the average volume of the shell/matrix comprises less than about 10%, 5%, 3% or 1% of the average particle volume. Those skilled in the art will appreciate that, such a matrix or shell volumes typically contributes little to the virtual particle density which is overwhelmingly dictated by the suspension medium found therein. Of course, in selected embodiments the excipients used to form the perforated microstructure may be chosen so the density of the resulting matrix or shell approximates the density of the surrounding suspension medium.

It will further be appreciated that, the use of such microstructures will allow the apparent density of the virtual particles to approach that of the suspension medium substantially eliminating the attractive van der Waals forces. Moreover, as previously discussed, the components of the microparticulate matrix are preferably selected, as much as possible given other considerations, to approximate the density of suspension medium. Accordingly, in preferred embodiments of the present invention, the virtual particles and the suspension medium will have a density differential of less than about 0.6 g/cm$^3$. That is, the mean density of the virtual particles (as defined by the matrix boundary) will be within approximately 0.6 g/cm$^3$ of the suspension medium. More preferably, the mean density of the virtual particles will be within 0.5, 0.4, 0.3 or 0.2 g/cm$^3$ of the selected suspension medium. In even more preferable embodiments the density differential will be less than about 0.1, 0.05, 0.01, or even less than 0.005 g/cm$^3$.

In addition to the aforementioned advantages, the use of hollow, porous particles allows for the formation of freeflowing dispersions comprising much higher volume fractions of particles in suspension. It should be appreciated that, the formulation of prior art dispersions at volume fractions approaching close-packing generally results in dramatic increases in dispersion viscoelastic behavior. Rheological behavior of this type is not appropriate for MDI applications. Those skilled in the art will appreciate that, the volume fraction of the particles may be defined as the ratio of the apparent volume of the particles (i.e. the particle volume) to the total volume of the system. Each system has a maximum volume fraction or packing fraction. For example, particles in a simple cubic arrangement reach a maximum packing fraction of 0.52 while those in a face centered cubic/hexagonal close packed configuration reach a maximum packing fraction of approximately 0.74. For non-spherical particles or polydisperse systems, the derived values are different. Accordingly, the maximum packing fraction is often considered to be an empirical parameter for a given system.

Here, it was surprisingly found that the porous structures of the present invention do not exhibit undesirable viscoelastic behavior even at high volume fractions, approaching close packing. To the contrary, they remain as free flowing, low viscosity suspensions having little or no yield stress when compared with analogous suspensions comprising solid particulates. The low viscosity of the disclosed suspensions is thought to be due, at least in large part, to the relatively low van der Waals attraction between the fluid-filled hollow, porous particles. As such, in selected embodiments the volume fraction of the disclosed dispersions is greater than approximately 0.3. Other embodiments may have packing values on the order of 0.3 to about 0.5 or on the order of 0.5 to about 0.8, with the higher values approaching a close packing condition. Moreover, as particle sedimentation tends to naturally decrease when the volume fraction approaches close packing, the formation of relatively concentrated dispersions may further increase formulation stability.

Although the methods and compositions of the present invention may be used to form relatively concentrated suspensions, the stabilizing factors work equally well at much lower packing volumes and such dispersions are contemplated as being within the scope of the instant disclosure. In this regard, it will be appreciated that, dispersions comprising low volume fractions are extremely difficult to stabilize using prior art techniques. Conversely, dispersions incorporating perforated microstructures comprising a bioactive agent as described herein are particularly stable even at low volume fractions. Accordingly, the present invention allows for stabilized dispersions, and particularly respiratory dispersions, to be formed and used at volume fractions less than 0.3. In some preferred embodiments, the volume fraction is approximately 0.0001-0.3, more preferably 0.001-0.01. Yet other preferred embodiments comprise stabilized suspensions having volume fractions from approximately 0.01 to approximately 0.1.

The perforated microstructures of the present invention may also be used to stabilize dilute suspensions of micronized bioactive agents. In such embodiments the perforated microstructures may be added to increase the volume fraction of particles in the suspension, thereby increasing suspension stability to creaming or sedimentation. Further, in these embodiments the incorporated microstructures may also act in preventing close approach (aggregation) of the micronized drug particles. It should be appreciated that, the perforated microstructures incorporated in such embodiments do not necessarily comprise a bioactive agent. Rather, they may be formed exclusively of various excipients, including surfactants.

Those skilled in the art will further appreciate that the stabilized suspensions or dispersions of the present invention may be prepared by dispersal of the microstructures in the selected suspension medium which may then be placed in a container or reservoir. In this regard, the stabilized preparations of the present invention can be made by simply combining the components in sufficient quantity to produce the final desired dispersion concentration. Although the microstructures readily disperse without mechanical energy, the application of mechanical energy to aid in dispersion (e.g. with the aid of sonication) is contemplated, particularly for the formation of stable emulsions or reverse emulsions. Alternatively, the components may be mixed by simple shaking or other type of agitation. The process is preferably carried out under anhydrous conditions to obviate any adverse effects of moisture on suspension stability. Once formed, the dispersion has a reduced susceptibility to flocculation and sedimentation.

As indicated throughout the instant specification, the dispersions of the present invention are preferably stabilized. In a broad sense, the term "stabilized dispersion" will be held to mean any dispersion that resists aggregation, flocculation or creaming to the extent required to provide for the effective delivery of a bioactive agent. While those skilled in the art will appreciate that there are several methods that may be used to assess the stability of a given dispersion, a preferred method for the purposes of the present invention comprises determination of creaming or sedimentation time using a dynamic photosedimentation method. As seen in Example IX and FIG. 2, a preferred method comprises subjecting suspended particles to a centrifugal force and measuring absorbance of the suspension as a function of time. A rapid decrease in the absorbance identifies a suspension with poor stability. It is submitted that those skilled in the art will be able to adapt the procedure to specific suspensions without undue experimentation.

For the purposes of the present invention the creaming time shall be defined as the time for the suspended drug particulates to cream to ½ the volume of the suspension medium. Similarly, the sedimentation time may be defined as the time it takes for the particulates to sediment in ½ the volume of the liquid medium. Besides the photosedimentation technique described above, a relatively simple way to determine the creaming time of a preparation is to provide the particulate suspension in a sealed glass vial. The vials are agitated or shaken to provide relatively homogeneous dispersions which are then set aside and observed using appropriate instrumentation or by visual inspection. The time necessary for the suspended particulates to cream to ½ the volume of the suspension medium (i.e., to rise to the top half of the suspension medium), or to sediment within ½ the volume (i.e., to settle in the bottom ½ of the medium), is then noted. Suspension formulations having a creaming time greater than 1 minute are preferred and indicate suitable stability. More preferably, the stabilized dispersions comprise creaming times of greater than 1, 2, 5, 10, 15, 20 or 30 minutes. In particularly preferred embodiments, the stabilized dispersions exhibit creaming times of greater than about 1, 1.5, 2, 2.5, or 3 hours. Substantially equivalent periods for sedimentation times are indicative of compatible dispersions.

As discussed herein, the stabilized dispersions disclosed herein may preferably be administered to the nasal or pulmonary air passages of a patient via aerosolization, such as with a metered dose inhaler. The use of such stabilized preparations provides for superior dose reproducibility and improved lung deposition as described above. MDIs are well known in the art and could easily be employed for administration of the claimed dispersions without undue experimentation. Breath activated MDIs, as well as those comprising other types of improvements which have been, or will be, developed are also compatible with the stabilized dispersions and present invention and, as such, are contemplated as being with in the scope thereof. However, it should be emphasized that, in preferred embodiments, the stabilized dispersions may be administered with an MDI using a number of different routes including, but not limited to, topical, nasal, pulmonary or oral. Those skilled in the art will appreciate that, such routes are well known and that the dosing and administration procedures may be easily derived for the stabilized dispersions of the present invention.

MDI canisters generally comprise a container or reservoir capable of withstanding the vapor pressure of the propellant used such as, a plastic or plastic-coated glass bottle, or preferably, a metal can or, for example, an aluminum can which may optionally be anodized, lacquer-coated and/or plastic-coated, wherein the container is closed with a metering valve. The metering valves are designed to deliver a metered amount of the formulation per actuation. The valves incorporate a gasket to prevent leakage of propellant through the valve. The gasket may comprise any suitable elastomeric material such as, for example, low density polyethylene, chlorobutyl, black and white butadiene-acrylonitrile rubbers, butyl rubber and neoprene. Suitable valves are commercially available from manufacturers well known in the aerosol industry, for example, from Valois, France (e.g. DFIO, DF30, DF 31/50 ACT, DF60), Bespak plc, LTK (e.g. BK300, BK356) and 3M-Neotechnic Ltd., LIK (e.g. Spraymiser).

Each filled canister is conveniently fitted into a suitable channeling device or actuator prior to use to form a metered dose inhaler for administration of the medicament into the lungs or nasal cavity of a patient. Suitable channeling devices comprise for example a valve actuator and a cylindrical or cone-like passage through which medicament may be delivered from the filled canister via the metering valve, to the nose or mouth of a patient e.g., a mouthpiece actuator. Metered dose inhalers are designed to deliver a fixed unit dosage of medicament per actuation such as, for example, in the range of 10 to 5000 micrograms of bioactive agent per actuation. Typically, a single charged canister will provide for tens or even hundreds of shots or doses.

With respect to MDIs, it is an advantage of the present invention that any biocompatible suspension medium having adequate vapor pressure to act as a propellant may be used. Particularly preferred suspension media are compatible with use in a metered dose inhaler. That is, they will be able to form aerosols upon the activation of the metering valve and associated release of pressure. In general, the selected suspension medium should be biocompatible (i.e. relatively non-toxic) and non-reactive with respect to the suspended perforated microstructures comprising the bioactive agent. Preferably, the suspension medium will not act as a substantial solvent for any components incorporated in the perforated microspheres. Selected embodiments of the invention comprise suspension media selected from the group consisting of fluorocarbons (including those substituted with other halogens), hydrofluoroalkanes, perfluorocarbons, hydrocarbons, alcohols, ethers or combinations thereof. It will be appreciated that, the suspension medium may comprise a mixture of various compounds selected to impart specific characteristics.

Particularly suitable propellants for use in the MDI suspension mediums of the present invention are those propellant gases that can be liquefied under pressure at room temperature and, upon inhalation or topical use, are safe, toxicologically innocuous and free of side effects. In this regard, compatible propellants may comprise any hydrocarbon, fluorocarbon, hydrogen-containing fluorocarbon or mixtures thereof having a sufficient vapor pressure to efficiently form aerosols upon activation of a metered dose inhaler. Those propellants typically termed hydrofluoroalkanes or HFAs are especially compatible. Suitable propellants include, for example, short chain hydrocarbons, $C_{1-4}$ hydrogen-containing chlorofluorocarbons such as $CH_2ClF$, $CCl_2F_2CHClF$, $CF_3CHClF$, $CHF_2CClF_2$, $CHClFCHF_2$, $CF_3CH_2Cl$, and $CClF_2CH_3$; $C_{1-4}$ hydrogen-containing fluorocarbons (e.g. HFAs) such as $CHF_2CHF_2$, $CF_3CH_2F$, $CHF_2CH_3$, and $CF_3CHFCF_3$; and perfluorocarbons such as $CF_3CF_3$ and $CF_3CF_2CF_3$. Preferably, a single perfluorocarbon or hydrogen-containing fluorocarbon is employed as the propellant. Particularly preferred as propellants are 1,1,1,2-tetrafluoroethane ($CF_3CH_2F$) (HFA-134a) and 1,1,1,2,3,3,3-heptafluoro-n-propane ($CF_3CHFCF_3$) (HFA-227), perfluoroethane, monochlorodifluoromethane, 1,1-difluoroethane, and combinations thereof. It is desirable that the formulations contain no components that deplete stratospheric ozone. In particular it is desirable that the formulations are substantially free of chlorofluorocarbons such as $CCl_3F$, $CCl_2F_2$, and $CF_3CCl_3$.

Specific fluorocarbons, or classes of fluorinated compounds, that are useful in the suspension media include, but are not limited to, fluoroheptane, fluorocycloheptane, fluoromethylcycloheptane, fluorohexane, fluorocyclohexane, fluoropentane, fluorocyclopentane, fluoromethylcyclopentane, fluorodimethylcyclopentanes, fluoromethylcyclobutane, fluorodimethylcyclobutane, fluorotrimethylcyclobutane, fluorobutane, fluorocyclobutane, fluoropropane, fluoroethers, fluoropolyethers and fluorotriethylamines. It will be appreciated that, these compounds may be used alone or in combination with more volatile propellants. It is a distinct advantage that such compounds are generally environmentally sound and biologically non-reactive.

In addition to the aforementioned fluorocarbons and hydrofluoroalkanes, various chlorofluorocarbons and substituted fluorinated compounds may also be used as suspension mediums in accordance with the teachings herein. In this respect, FC-11 (CCL3F), FC-11B1 (CBrCl2F), FC-11B2 (CBr2ClF), FCl2B2 (CF2Br2), FC21 (CHCl2F), FC21B1 (CHBrClF), FC-21B2 (CHBr2F), FC-31B1 (CH2BrF), FC113A (CCl3CF3), FC-122 (CClF2CHCl2), FCl23 (CF3CHCl2), FC-132 (CHClFCHClF), FC-133 (CHClFCHF2), FC-141 (CH2ClCHClF), FC-141B (CCl2FCH3), FC-142 (CHF2CH2Cl), FC-151 (CH2FCH2Cl), FC-152 (CH2FCH2F), FC-1112 (CClF=CClF), FC-1121 (CHCl=CFCl) and FC-1131 (CHCl=CHF) are all compatible with the teachings herein despite possible attendant environmental concerns. As such, each of these compounds may be used, alone or in combination with other compounds (i.e. less volatile fluorocarbons) to form the stabilized respiratory dispersions of the present invention.

Along with the aforementioned embodiments, the stabilized dispersions of the present invention may also be used in conjunction with nebulizers to provide an aerosolized medicament that may be administered to the pulmonary air passages of a patient in need thereof. Nebulizers are well known in the art and could easily be employed for administration of the claimed dispersions without undue experimentation. Breath activated nebulizers, as well as those comprising other types of improvements which have been, or will be, developed are also compatible with the stabilized dispersions and present invention and are contemplated as being with in the scope thereof.

Nebulizers work by forming aerosols, that is converting a bulk liquid into small droplets suspended in a breathable gas. Here, the aerosolized medicament to be administered (preferably to the pulmonary air passages) will comprise small droplets of suspension medium associated with perforated microstructures comprising a bioactive agent. In such embodiments, the stabilized dispersions of the present invention will typically be placed in a fluid reservoir operably associated with a nebulizer. The specific volumes of preparation provided, means of filling the reservoir, etc., will largely be dependent on the selection of the individual nebulizer and is well within the purview of the skilled artisan. Of course, the present invention is entirely compatible with single-dose nebulizers and multiple dose nebulizers.

Traditional prior art nebulizer preparations typically comprise aqueous solutions of the selected pharmaceutical compound. With such prior art nebulizer preparations, it has long been established that corruption of the incorporated therapeutic compound can severely reduce efficacy. For example, with conventional aqueous multi-dose nebulizer preparations, bacterial contamination is a constant problem. In addition, the solubilized medicament may precipitate out, or degrade over time, adversely affecting the delivery profile. This is particularly true of larger, more labile biopolymers such as enzymes or other types of proteins. Precipitation of the incorporated bioactive agent may lead to particle growth that results in a substantial reduction in lung penetration and a corresponding decrease in bioavailability. Such dosing incongruities markedly decrease the effectiveness of any treatment.

The present invention overcomes these and other difficulties by providing stabilized dispersions with a suspension medium that preferably comprises a fluorinated compound (i.e. a fluorochemical, fluorocarbon or perfluorocarbon). Particularly preferred embodiments of the present invention comprise fluorochemicals that are liquid at room temperature. As indicated above, the use of such compounds, whether as a continuous phase or, as a suspension medium, provides several advantages over prior art liquid inhalation preparations. In this regard, it is well established that many fluorochemicals have a proven history of safety and biocompatibility in the lung. Further, in contrast to aqueous solutions, fluorochemicals do not negatively impact gas exchange following pulmonary administration. To the contrary, they may actually be able to improve gas exchange and, due to their unique wettability characteristics, are able to carry an aerosolized stream of particles deeper into the lung, thereby improving systemic delivery of the desired pharmaceutical compound. In addition, the relatively non-reactive nature of fluorochemicals acts to retard any degradation of an incorporated bioactive agent. Finally, many fluorochemicals are also bacteriostatic thereby decreasing the potential for microbial growth in compatible nebulizer devices.

In any event, nebulizer mediated aerosolization typically requires an input of energy in order to produce the increased surface area of the droplets and, in some cases, to provide transportation of the atomized or aerosolized medicament. One common mode of aerosolization is forcing a stream of fluid to be ejected from a nozzle, whereby droplets are formed. With respect to nebulized administration, additional energy is usually imparted to provide droplets that will be sufficiently small to be transported deep into the lungs. Thus, additional energy is needed, such as that provided by a high velocity gas stream or a piezoelectric crystal. Two popular types of nebulizers, jet nebulizers and ultrasonic nebulizers, rely on the aforementioned methods of applying additional energy to the fluid during atomization.

In terms of pulmonary delivery of bioactive agents to the systemic circulation via nebulization, recent research has focused on the use of portable hand-held ultrasonic nebulizers, also referred to as metered solutions. These devices, generally known as single-bolus nebulizers, aerosolize a single bolus of medication in an aqueous solution with a particle size efficient for deep lung delivery in one or two breaths. These devices fall into three broad categories. The first category comprises pure piezoelectric single-bolus nebulizers such as those described by Miitterlein, et. al., (J. Aerosol Med. 1988; 1:231). In another category, the desired aerosol cloud may be generated by microchannel extrusion single-bolus nebulizers such as those described in U.S. Pat. No. 3,812,854. Finally, a third category comprises devices exemplified by Robertson, et. al., (WO 92/11050) which describes cyclic pressurization single-bolus nebulizers. Each of the aforementioned references is incorporated herein in their entirety. Most devices are manually actuated, but some devices exist which are breath actuated. Breath actuated devices work by releasing aerosol when the device senses the patient inhaling through a circuit. Breath actuated nebulizers may also be placed in-line on a ventilator circuit to release aerosol into the air flow which comprises the inspiration gases for a patient.

Regardless of which type of nebulizer is employed, it is an advantage of the present invention that biocompatible non-aqueous compounds may be used as suspension mediums. Preferably, they will be able to form aerosols upon the application of energy thereto. In general, the selected suspension medium should be biocompatible (i.e. relatively non-toxic) and non-reactive with respect to the suspended perforated microstructures comprising the bioactive agent. Preferred embodiments comprise suspension media selected from the group consisting of fluorochemicals, fluorocarbons (including those substituted with other halogens), perfluorocarbons, fluorocarbon/hydrocarbon diblocks, hydrocarbons, alcohols, ethers, or combinations thereof. It will be appreciated that, the suspension medium may comprise a mixture of various compounds selected to impart specific characteristics. It will also be appreciated that the perforated microstructures are preferably insoluble in the suspension medium, thereby providing for stabilized medicament particles, and effectively protecting a selected bioactive agent from degradation, as might occur during prolonged storage in an aqueous solution. In preferred embodiments, the selected suspension medium is bacteriostatic. The suspension formulation also protects the bioactive agent from degradation during the nebulization process.

As indicated above, the suspension media may comprise any one of a number of different compounds including hydrocarbons, fluorocarbons or hydrocarbon/fluorocarbon diblocks. In general, the contemplated hydrocarbons or highly fluorinated or perfluorinated compounds may be linear, branched or cyclic, saturated or unsaturated compounds. Conventional structural derivatives of these fluorochemicals and hydrocarbons are also contemplated as being within the scope of the present invention as well. Selected embodiments comprising these totally or partially fluorinated compounds may contain one or more heteroatoms and/or atoms of bromine or chlorine. Preferably, these fluorochemicals comprise from 2 to 16 carbon atoms and include, but are not limited to, linear, cyclic or polycyclic perfluoroalkanes, bis(perfluoroalkyl)alkenes, perfluoroethers, perfluoroamines, perfluoroalkyl bromides and perfluoroalkyl chlorides such as dichlorooctane. Particularly preferred fluorinated compounds for use in the suspension medium may comprise perfluorooctyl bromide $C_8F_{17}Br$ (PFOB or perflubron), dichlorofluorooctane $C_8F_{16}Cl_2$, and the hydrofluoroalkane perfluorooctyl ethane $C_8F_{17}C_2H_5$ (PFOE). With respect to other embodiments, the use of perfluorohexane or perfluoropentane as the suspension medium is especially preferred.

More generally, exemplary fluorochemicals which are contemplated for use in the present invention generally include halogenated fluorochemicals (i.e. $C_nF_{2n+1}X$, $XC_nF_{2n}X$, where n=2-10, X=Br, Cl or I) and, in particular, 1-bromo-F-butane n-$C_4F_9Br$, 1-bromo-F-hexane (n-$C_6F_{13}Br$), 1-bromo-F-heptane (n-$C_7F_{15}Br$), 1,4-dibromo-F-butane and 1,6-dibromo-F-hexane. Other useful brominated fluorochemicals are disclosed in U.S. Pat. No. 3,975,512 to Long and are incorporated herein by reference. Specific fluorochemicals having chloride substituents, such as perfluorooctyl chloride (n-$C_8F_{17}Cl$), 1,8-dichloro-F-octane (n-$ClC_8F_{16}Cl$), 1,6-dichloro-F-hexane (n-$ClC_6F_{12}Cl$), and 1,4-dichloro-F-butane (n-$ClC_4F_8Cl$) are also preferred.

Fluorocarbons, fluorocarbon-hydrocarbon compounds and halogenated fluorochemicals containing other linkage groups, such as esters, thioethers and amines are also suitable for use as suspension media in the present invention. For instance, compounds having the general formula, $C_nF_{2n+1}OC_mF_{2m+1}$, or $C_nF_{2n+1}CH=CHC_mF_{2m+1}$, (as for example $C_4F_9CH=CHC_4F_9$ (F-44E), i-$C_3F_9CH=CHC_6F_{13}$ (F-i36E), and $C_6F_{13}CH=CHC_6F_{13}$ (F-66E)) where n and m are the same or different and n and m are integers from about 2 to about 12 are compatible with teachings herein. Useful fluorochemical-hydrocarbon diblock and triblock compounds include those with the general formulas $C_nF_{2n+1}$—$C_mH_{2m+1}$ and $C_nF_{2n+1}C_mH_{2m-1}$, where n=2-12; m=2-16 or $C_pH_{2p+1}$—$C_nF_{2n}$—$C_mH_{2m+1}$, where p=1-12, m=1-12 and n=2-12. Preferred compounds of this type include $C_8F_{17}C_2H_5$, $C_6F_{13}C_{10}H_{21}$, $C_8F_{17}C_8H_{17}$, $C_6F_{13}CH=CHC_6H_{13}$ and $C_8F_{17}CH=CHC_{10}H_{21}$. Substituted ethers or polyethers (i.e. $XC_nF_{2n}OC_mF_{2m}X$, $XCFOC_nF_{2n}OCF_2X$, where n and m=1-4, X=Br, Cl or I) and fluorochemical-hydrocarbon ether diblocks or triblocks (i.e. $C_nF_{2n+1}$—O—$C_mH_{2m+1}$, where n=2-10; m=2-16 or $C_pH_{2p+1}$—O—$C_nF_{2n}$—O—$C_mH_{2m+1}$, where p=2-12, m=1-12 and n=2-12) may also used as well as $C_nF_{2n+1}O$—$C_mF_{2m}OC_pH_{2p+1}$, wherein n, m and p are from 1-12. Furthermore, depending on the application, perfluoroalkylated ethers or polyethers may be compatible with the claimed dispersions.

Polycyclic and cyclic fluorochemicals, such as $C_{10}F_{18}$ (F-decalin or perfluorodecalin), perfluoroperhydrophenanthrene, perfluorotetramethylcyclohexane (AP-144) and perfluoro n-butyldecalin are also within the scope of the invention. Additional useful fluorochemicals include perfluorinated amines, such as F-tripropylamine ("FTPA") and F-tributylamine ("FTBA"). F-4-methyloctahydroquinolizine ("FMOQ"), F-N-methyl-decahydroisoquinoline ("FMIQ"), F-N-methyldecahydroquinoline ("FHQ"), F-N-cyclohexylpyrrolidine ("FCHP") and F-2-butyltetrahydrofuran ("FC-75" or "FC-77"). Still other useful fluorinated compounds include perfluorophenanthrene, perfluoromethyldecalin, perfluorodimethylethylcyclohexane, perfluorodimethyldecalin, perfluorodiethyldecalin, perfluoromethyladamantane, perfluorodimethyladamantane. Other contemplated fluorochemicals having nonfluorine substituents, such as, perfluorooctyl hydride, and similar compounds having different numbers of carbon atoms are also useful. Those skilled in the art will further appreciate that other variously modified fluorochemicals are encompassed within the broad definition of fluorochemical as used in the instant application and suitable for use in the present invention. As such, each of the foregoing compounds may be used, alone or in combination with other compounds to form the stabilized dispersions of the present invention.

Specific fluorocarbons, or classes of fluorinated compounds, that may be useful as suspension media include, but are not limited to, fluoroheptane, fluorocycloheptane fluoromethylcycloheptane, fluorohexane, fluorocyclohexane, fluoropentane, fluorocyclopentane, fluoromethylcyclopentane, fluorodimethylcyclopentanes, fluoromethylcyclobutane, fluorodimethylcyclobutane, fluorotrimethylcyclobutane, fluorobutane, fluorocyclobutane, fluoropropane, fluoroethers, fluoropolyethers and fluorotriethylamines. Such compounds are generally environmentally sound and are biologically non-reactive.

While any fluid compound capable of producing an aerosol upon the application of energy may be used in conjunction with the present invention, the selected suspension medium will preferably have a vapor pressure less than about 5 atmospheres and more preferably less than about 2 atmospheres. Unless otherwise specified, all vapor pressures recited herein are measured at 25° C. In other embodiments, preferred suspension media compounds will have vapor pressures on the order of about 5 torr to about 760 torr, with more preferable compounds having vapor pressures on the order of from about 8 torr to about 600 torr, while still more preferable compounds will have vapor pressures on the order of from about 10 torr to about 350 torr. Such suspension media may be used in conjunction with compressed air nebulizers, ultrasonic nebulizers or with mechanical atomizers to provide effective ventilation therapy. Moreover, more volatile compounds may be mixed with lower vapor pressure components to provide suspension media having specified physical characteristics selected to further improve stability or enhance the bioavailability of the dispersed bioactive agent.

Other embodiments of the present invention directed to nebulizers will comprise suspension media that boil at selected temperatures under ambient conditions (i.e. 1 atm). For example, preferred embodiments will comprise suspension media compounds that boil above 0° C., above 5° C., above 10° C., above 15°, or above 20° C. In other embodiments, the suspension media compound may boil at or above 25° C. or at or above 30° C. In yet other embodiments, the selected suspension media compound may boil at or above human body temperature (i.e. 37° C.), above 45° C., 55° C., 65° C., 75° C., 85° C. or above 100° C.

Along with MDIs and nebulizers, it will be appreciated that the stabilized dispersions of the present invention may be used in conjunction with liquid dose instillation or LDI techniques. Liquid dose instillation involves the direct administration of a stabilized dispersion to the lung. In this regard, direct pulmonary administration of bioactive compounds is particularly effective in the treatment of disorders especially where poor vascular circulation of diseased portions of a lung reduces the effectiveness of intravenous drug delivery. With respect to LDI the stabilized dispersions are preferably used in conjunction with partial liquid ventilation or total liquid ventilation. Moreover, the present invention may further comprise introducing a therapeutically beneficial amount of a physiologically acceptable gas (such as nitric oxide or oxygen) into the pharmaceutical microdispersion prior to, during or following administration.

For LDI, the dispersions of the present invention may be administered to the lung using a pulmonary delivery conduit. Those skilled in the art will appreciate the term "pulmonary delivery conduit", as used herein, shall be construed in a broad sense to comprise any device or apparatus, or component thereof, that provides for the instillation or administration of a liquid in the lungs. In this respect a pulmonary delivery conduit or delivery conduit shall be held to mean any bore, lumen, catheter, tube, conduit, syringe, actuator, mouthpiece, endotracheal tube or bronchoscope that provides for the administration or instillation of the disclosed dispersions to at least a portion of the pulmonary air passages of a patient in need thereof. It will be appreciated that the delivery conduit may or may not be associated with a liquid ventilator or gas ventilator. In particularly preferred embodiments the delivery conduit shall comprise an endotracheal tube or bronchoscope.

Here it must be emphasized that the dispersions of the present invention may be administered to ventilated (e.g. those connected to a mechanical ventilator) or nonventilated, patients (e.g. those undergoing spontaneous respiration). Accordingly, in preferred embodiments the methods and systems of the present invention may comprise the use or inclusion of a mechanical ventilator. Further, the stabilized dispersions of the present invention may also be used as a lavage agent to remove debris in the lung, or for diagnostic lavage procedures. In any case the introduction of liquids, particularly fluorochemicals, into the lungs of a patient is well known and could be accomplished by a skilled artisan in possession of the instant specification without undue experimentation.

Those skilled in the art will appreciate that suspension media compatible with LDI techniques are similar to those set forth above for use in conjunction with nebulizers. Accordingly, for the purposes of the present application suspension media for dispersions compatible with LDI shall be equivalent to those enumerated above in conjunction with use in nebulizers. In any event, it will be appreciated that in particularly preferred LDI embodiments the selected suspension medium shall comprise a fluorochemical that is liquid under ambient conditions.

It will be understood that, in connection with the present invention, the disclosed dispersions are preferably administered directly to at least a portion of the pulmonary air passages of a mammal. As used herein, the terms "direct instillation" or "direct administration" shall be held to mean the introduction of a stabilized dispersion into the lung cavity of a mammal. That is, the dispersion will preferably be administered through the trachea of a patient and into the lungs as a relatively free flowing liquid passing through a delivery conduit and into the pulmonary air passages. In this regard, the flow of the dispersion may be gravity assisted or may be afforded by induced pressure such as through a pump or the compression of a syringe plunger. In any case, the amount of dispersion administered may be monitored by mechanical devices such as flow meters or by visual inspection.

While the stabilized dispersions may be administered up to the functional residual capacity of the lungs of a patient, it will be appreciated that selected embodiments will comprise the pulmonary administration of much smaller volumes (e.g. on the order of a milliliter or less). For example, depending on the disorder to be treated, the volume administered may be on the order of 1, 3, 5, 10, 20, 50, 100, 200 or 500 milliliters. In preferred embodiments the liquid volume is less than 0.25 or 0.5 percent FRC. For particularly preferred embodiments, the liquid volume is 0.1 percent FRC or less. With respect to the administration of relatively low volumes of stabilized dispersions it will be appreciated that the wettability and spreading characteristics of the suspension media (particularly fluorochemicals) will facilitate the even distribution of the bioactive agent in the lung. However, in other embodiments it may be preferable to administer the suspensions a volumes of greater than 0.5, 0.75 or 0.9 percent FRC. In any event, LDI treatment as disclosed herein represents a new alternative for critically ill patients on mechanical ventilators, and opens the door for treatment of less ill patients with bronchoscopic administration.

It will also be understood that other components can be included in the stabilized dispersions of the present invention. For example, osmotic agents, stabilizers, chelators, buffers, viscosity modulators, salts, and sugars can be added to fine tune the stabilized dispersions for maximum life and ease of administration. Such components may be added directly to the suspension medium or associated with, or incorporated in, the perforated microstructures. Considerations such as sterility, isotonicity, and biocompatibility may govern the use of conventional additives to the disclosed compositions. The use of such agents will be understood to those of ordinary skill in the art and, the specific quantities, ratios, and types of agents can be determined empirically without undue experimentation.

Moreover, while the stabilized dispersions of the present invention are particularly suitable for the pulmonary administration of bioactive agents, they may also be used for the localized or systemic administration of compounds to any location of the body. Accordingly, it should be emphasized that, in preferred embodiments, the formulations may be administered using a number of different routes including, but not limited to, the gastrointestinal tract, the respiratory tract, topically, intramuscularly, intraperitoneally, nasally, vaginally, rectally, aurally, orally or ocular. More generally, the stabilized dispersions of the present invention may be used to deliver agents topically or by administration to a non-pulmonary body cavity. In preferred embodiments the body cavity is selected from the group consisting of the peritoneum, sinus cavity, rectum, urethra, gastrointestinal tract, nasal cavity, vagina, auditory meatus, oral cavity, buccal pouch and pleura. Among other indications, stabilized dispersions comprising the appropriate bioactive agent, (e.g. an antibiotic or an anti-inflammatory), may be used to treat infections of the eye, sinusitis, infections of the auditory tract and even infections or disorders of the gastrointestinal tract. With respect to the latter, the dispersions of the present invention may be used to selectively deliver pharmaceutical compounds to the lining of the stomach for the treatment of *H. pylori* infections or other ulcer related disorders.

With regard to the perforated microstructure powders and stabilized dispersions disclosed herein those skilled in the art will appreciate that they may be advantageously supplied to the physician or other health care professional, in a sterile, prepackaged or kit form. More particularly, the formulations may be supplied as stable powders or preformed dispersions ready for administration to the patient. Conversely, they may be provided as separate, ready to mix components. When provided in a ready to use form, the powders or dispersions may be packaged in single use containers or reservoirs, as well as in multi-use containers or reservoirs. In either case, the container or reservoir may be associated with the selected inhalation or administration device and used as described herein. When provided as individual components (e.g., as powdered microspheres and as neat suspension medium) the stabilized preparations may then be formed at any time prior to use by simply combining the contents of the containers as directed. Additionally, such kits may contain a number of ready to mix, or prepackaged dosing units so that the user can then administer them as needed.

Although preferred embodiments of the present invention comprise powders and stabilized dispersions for use in pharmaceutical applications, it will be appreciated that the perforated microstructures and disclosed dispersions may be used for a number of non pharmaceutical applications. That is, the present invention provides perforated microstructures which have a broad range of applications where a powder is suspended and/or aerosolized. In particular, the present invention is especially effective where an active or bioactive ingredient must be dissolved, suspended or solubilized as fast as possible. By increasing the surface area of the porous microparticles or by incorporation with suitable excipients as described herein, will result in an improvement in dispersibility, and/or suspension stability. In this regard, rapid dispersement applications include, but are not limited to: detergents, dishwasher detergents, food sweeteners, condiments, spices, mineral flotation detergents, thickening agents, foliar fertilizers, phytohormones, insect pheromones, insect repellents, pet repellents, pesticides, fungicides, disinfectants, perfumes, deodorants, etc.

Applications that require finely divided particles in a nonaqueous suspension media (i.e., solid, liquid or gaseous) are also contemplated as being within the scope of the present invention. As explained herein, the use of perforated microstructures to provide a "homodispersion" minimizes particle-particle interactions. As such, the perforated microspheres and stabilized suspensions of the present invention are particularly compatible with applications that require: inorganic pigments, dyes, inks, paints, explosives, pyrotechnic, adsorbents, absorbents, catalyst, nucleating agents, polymers, resins, insulators, fillers, etc. The present invention offers benefits over prior art preparations for use in applications which require aerosolization or atomization. In such non pharmaceutical uses the preparations can be in the form of a liquid suspension (such as with a propellant) or as a dry powder.

Preferred embodiments comprising perforated microstructures as described herein include, but are not limited to, ink jet printing formulations, powder coating, spray paint, spray pesticides etc.

The foregoing description will be more fully understood with reference to the following Examples. Such Examples, are, however, merely representative of preferred methods of practicing the present invention and should not be read as limiting the scope of the invention.

I

Preparation of Hollow Porous Particles of Gentamicin Sulfate by Spray-Drying 40 to 60 ml of the following solutions were prepared for spray drying:
50% w/w hydrogenated phosphatidylcholine, E-100-3 (Lipoid KG, Ludwigshafen, Germany)
50% w/w gentamicin sulfate (Amresco, Solon, Ohio)
Perfluorooctylbromide, Perflubron (NMK, Japan)
Deionized water Perforated microstructures comprising gentamicin sulfate were prepared by a spray drying technique using a B-191 Mini Spray-Drier (Büchi, Flawil, Switzerland) under the following conditions: aspiration: 100%, inlet temperature: 85° C.; outlet temperature: 61° C.; feed pump: 10%; $N_2$ flow: 2,800 L/hr. Variations in powder porosity were examined as a function of the blowing agent concentration.

Fluorocarbon-in-water emulsions of perfluorooctyl bromide containing a 1:1 w/w ratio of phosphatidylcholine (PC), and gentamicin sulfate were prepared varying only the PFC/PC ratio. 1.3 grams of hydrogenated egg phosphatidylcholine was dispersed in 25 mL deionized water using an Ultra-Turrax mixer (model T-25) at 8000 rpm for 2 to 5 minutes (T=60-70° C.). A range from 0 to 40 grams of perflubron was added dropwise during mixing (T=60-70° C.). After addition was complete, the fluorocarbon-in-water emulsion was mixed for an additional period of not less than 4 minutes. The resulting coarse emulsions were then homogenized under high pressure with an Avestin (Ottawa, Canada) homogenizer at 15,000 psi for 5 passes. Gentamicin sulfate was dissolved in approximately 4 to 5 mL deionized water and subsequently mixed with the perflubron emulsion immediately prior to the spray dry process. The gentamicin powders were then obtained by spray drying using the conditions described above. A free flowing pale yellow powder was obtained for all perflubron containing formulations. The yield for each of the various formulations ranged from 35% to 60%.

II

Morphology of Gentamicin Sulfate Spray-Dried Powders

A strong dependence of the powder morphology, degree of porosity, and production yield was observed as a function of the PFC/PC ratio by scanning electron microscopy (SEM). A series of six SEM micrographs illustrating these observations, labeled 1A1 to 1F1, are shown in the left hand column of FIG. 1. As seen in these micrographs, the porosity and surface roughness was found to be highly dependent on the concentration of the blowing agent, where the surface roughness, number and size of the pores increased with increasing PFC/PC ratios. For example, the formulation devoid of perfluorooctyl bromide produced microstructures that appeared to be highly agglomerated and readily adhered to the surface of the glass vial. Similarly, smooth, spherically shaped microparticles were obtained when relatively little (PFC/PC ratio=1.1 or 2.2) blowing agent was used. As the PFC/PC ratio was increased the porosity and surface roughness increased dramatically.

As shown in the right hand column of FIG. 1, the hollow nature of the microstructures was also enhanced by the incorporation of additional blowing agent. More particularly, the series of six micrographs labeled 1A2 to 1F2 show cross sections of fractured microstructures as revealed by transmission electron microscopy (TEM). Each of these images was produced using the same microstructure preparation as was used to produce the corresponding SEM micrograph in the left hand column. Both the hollow nature and wall thickness of the resulting perforated microstructures appeared to be largely dependent on the concentration of the selected blowing agent. That is, the hollow nature of the preparation appeared to increase and the thickness of the particle walls appeared to decrease as the PFC/PC ratio increased. As may be seen in FIGS. 1A2 to 1C2 substantially solid structures were obtained from formulations containing little or no fluorocarbon blowing agent. Conversely, the perforated microstructures produced using a relatively high PFC/PC ratio of approximately 45 (shown in FIG. 1F2 proved to be extremely hollow with a relatively thin wall ranging from about 43.5 to 261 nm. Both types of particles are compatible for use in the present invention.

III

Preparation of Spray Dried Gentamicin Sulfate Particles using Various Blowing Agents 40 milliliters of the following solutions were prepared for spray drying:
50% w/w Hydrogenated Phosphatidylcholine, E100-3 (Lipoid KG, Ludwigshafen, Germany)
50% w/w Gentamicin Sulfate (Amresco, Solon Ohio)
Deionized water.
Blowing Agents:
Perfluorodecalin, FDC (Air products, Allenton Pa.)
Perfluorooctylbromide, Perflubron (Atochem, Paris, France)
Perfluorhexane, PFH (3M, St. Paul, Minn.)
1,1,2-trichlorotrifluoroethane, Freon 113 (Baxter, McGaw Park, Ill.)

Hollow porous microspheres with a model hydrophilic drug, e.g., gentamicin sulfate, were prepared by spray drying. The blowing agent in these formulations consisted of an emulsified fluorochemical (FC) oil. Emulsions were prepared with the following FCs: PFH, Freon 113, Perflubron and FDC. 1.3 grams of hydrogenated egg phosphatidylcholine was dispersed in 25 mL deionized water using a Ultra-Turrax mixer (model T-25) at 8000 rpm for 2 to 5 minutes (T=60-70). 25 grams of FC was added dropwise during mixing (T=60-70° C.). After the addition was complete, the FC-in-water emulsion was mixed for a total of not less than 4 minutes. The resulting emulsions were then further processed using an Avestin (Ottawa, Canada) high pressure homogenizer at 15,000 psi and 5 passes. Gentamicin sulfate was dissolved in approximately 4 to 5 mL deionized water and subsequently mixed with the FC emulsion. The gentamicin powders were obtained by spray drying (Büchi, 191 Mini Spray Dryer). Each emulsion was fed at a rate of 2.5 mL/min. The inlet and outlet temperatures of the spray dryer were 85° C. and 55° C. respectively. The nebulization air and aspiration flows were 2800 L/hr and 100% respectively.

A free flowing pale yellow dry powder was obtained for all formulations. The yield for the various formulations ranged from 35 to 60%. The various gentamicin sulfate powders had a mean volume weighted particle diameters that ranged from 1.52 to 4.91 μm.

IV

Effect of Blowing Agent on the Morphology of Gentamicin Sulfate Spray-Dried Powders A strong dependence of the powder morphology, porosity, and production yield (amount of powder captured in the cyclone) was observed as a function of the blowing agent boiling point. In this respect the powders produced in Example III were observed using scanning electron microscopy. Spray drying a fluorochemical (FC) emulsion with a boiling point at or below the 55° C. outlet temperature (e.g., perfluorohexane [PFH] or Freon 113), yielded amorphously shaped (shriveled or deflated) powders that contained little or no pores. Whereas, emulsions formulated with higher boiling FCs (e.g., perflubron, perfluorodecalin, FDC) produced spherical porous particles. Powders produced with higher boiling blowing agents also had production yields approximately two times greater than powders produced using relatively low boiling point blowing agents. The selected blowing agents and their boiling points are shown in Table II directly below.

TABLE II

| Blowing Agent | (bp ° C.) |
|---|---|
| Freon 113 | 47.6 |
| PFH | 56 |
| FDC | 141 |
| Perflubron | 141 |

Example IV illustrates that the physical characteristics of the blowing agent (i.e., boiling point) greatly influences the ability to provide perforated microparticles. A particular advantage of the present invention is the ability to alter the microstructure morphology and porosity by modifying the conditions and nature of the blowing agent.

V

Preparation of Spray Dried Albuterol Sulfate Particles using Various Blowing Agents Approximately 185 ml of the following solutions were prepared for spray drying:

49% w/w Hydrogenated Phosphatidylcholine, E100-3 (Lipoid KG, Ludwigshafen, Germany)
50% w/w Albuterol Sulfate (Accurate Chemical, Westbury, N.Y.)
1% w/w Poloxamer 188, NF grade (Mount Olive, N.J.)
Deionized water.
Blowing Agents:
Perfluorodecalin, FDC (Air products, Allenton Pa.)
Perfluorooctylbromide, Perflubron (Atochem, Paris)
Perfluorobutylethane F4H2 (F-Tech, Japan)
Perfluorotributylamine FTBA (3M, St. Paul, Minn.)

Albuterol sulfate powder was prepared by spray-drying technique by using a B-191 Mini Spray-Drier (Büchi, Flawil, Switzerland) under the following conditions:

Aspiration: 100%
Inlet temperature: 85° C.
Outlet temperature: 61° C.
Feed pump: 2.5 mL/min.
$N_2$ flow: 47 L/min.

The feed solution was prepared by mixing solutions A and B prior to spray drying.

Solution A: Twenty grams of water was used to dissolve 1.0 grams of Albuterol sulfate and 0.021 grams of poloxamer 188.

Solution B represented an emulsion of a fluorocarbon in water, stabilized by a phospholipid, which was prepared in the following way. Hydrogenated phosphatidylcholine (1.0 grams) was homogenized in 150 grams of hot deionized water (T=50 to 60° C.) using an Ultra-Turrax mixer (model T-25) at 8000 rpm, for 2 to 5 minutes (T=60-70° C.). Twenty-five grams of Perflubron (Atochem, Paris, France) was added dropwise during mixing. After the addition was complete, the Fluorochemical-in-water emulsion was mixed for at least 4 minutes. The resulting emulsion was then processed using an Avestin (Ottawa, Canada) high-pressure homogenizer at 18,000 psi and 5 passes. Solutions A and B were combined and fed into the spray dryer under the conditions described above. A free flowing, white powder was collected at the cyclone separator as is standard for this spray dryer. The albuterol sulfate powders had mean volume weighted particle diameters ranging from 1.28 to 2.77 µm, as determined by an Aerosizer (Amherst Process Instruments, Amherst, Mass.). By SEM, the albuterol sulfate/phospholipid spray dried powders were spherical and highly porous.

Example V further demonstrates the wide variety of blowing agents that may be used to provide perforated microparticles. A particular advantage of the present invention is the ability to alter the microstructure morphology and porosity by manipulating the formulation and spray drying conditions. Furthermore, Example V demonstrates the particle diversity achieved by the present invention and the ability to effectively incorporate a wide variety of pharmaceutical agents therein.

VI

Preparation of Hollow Porous PVA Particles by Spray Drying a Water-in-Oil Emulsion 100 ml of the following solutions were prepared for spray drying:
80% w/w Bis-(2-ethylhexyl) Sulfosuccinic Sodium Salt, (Aerosol OT, Kodak, Rochester, N.Y.)
20% w/w Polyvinyl Alcohol, average molecular weight=30,000-70,000 (Sigma Chemicals, St. Louis, Mo.)
Carbon Tetrachloride (Aldrich Chemicals, Milwaukee, Wis.)
Deionized water.

Aerosol OT/polyvinyl alcohol particles were prepared by spray-drying technique using a B-191 Mini Spray-Drier (Büchi, Flawil, Switzerland) under the following conditions:
Aspiration: 85%
Inlet temperature: 60° C.
Outlet temperature: 43° C.
Feed pump: 7.5 mL/min.
$N_2$ flow: 36 L/min.

Solution A: Twenty grams of water was used to dissolve 500 milligrams of polyvinyl alcohol (PVA).

Solution B represented an emulsion of carbon tetrachloride in water, stabilized by aerosol OT, which was prepared in the following way. Two grams of aerosol OT, was dispersed in 80 grams of carbon tetrachloride using a Ultra-Turrax mixer (model T-25) at 8000 rpm for 2 to 5 minutes (T=15° to 20° C.). Twenty grams of 2.5% w/v PVA was added dropwise during mixing. After the addition was complete, the water-in-oil emulsion was mixed for a total of not less than 4 minutes (T=15° to 20° C.). The resulting emulsion was then processed using an Avestin (Ottawa, Canada) high-pressure homogenizer at 12,000 psi and 2 passes. The emulsion was then fed into the spray dryer under the conditions described above. A free flowing, white powder was collected at the cyclone separator as is standard for this spray dryer. The Aerosol OT/PVA powder had a mean volume weighted particle diameter of 5.28±3.27 µm as determined by an Aerosizer (Amherst Process Instruments, Amherst, Mass.).

Example VI further demonstrates the variety of emulsion systems (here, reverse water-in-oil), formulations and conditions that may be used to provide perforated microparticles. A particular advantage of the present invention is the ability to alter formulations and/or conditions to produce compositions having a microstructure with selected porosity. This principle is further illustrated in the following example.

VII

Preparation of Hollow Porous Polycaprolactone Particles by Spray Drying a Water-in-Oil Emulsion 100 mls of the following solutions were prepared for spray drying:
80% w/w Sorbitan Monostearate, Span 60 (Aldrich Chemicals, Milwaukee, Wis.)
20% w/w Polycaprolactone, average molecular weight=65,000 (Aldrich Chemicals, Milwaukee, Wis.)
Carbon Tetrachloride (Aldrich Chemicals, Milwaukee, Wis.)
Deionized water.

Span 60/polycaprolactone particles were prepared by spray-drying technique by using a B-191 Mini Spray-Drier (Büchi, Flawil, Switzerland) under the following conditions:
Aspiration: 85%
Inlet temperature: 50° C.
Outlet temperature: 38° C.
Feed pump: 7.5 mL/min.
$N_2$ flow: 36 L/min.

A water-in-carbon tetrachloride emulsion was prepared in the following manner. Two grams of Span 60, was dispersed in 80 grams of carbon tetrachloride using an Ultra-Turrax mixer (model T-25) at 8000 rpm for 2 to 5 minutes (T=15 to 20° C.). Twenty grams of deionized water was added dropwise during mixing. After the addition was complete, the water-in-oil emulsion was mixed for a total of not less than 4 minutes (T=15 to 20° C.). The resulting emulsion was then further processed using an Avestin (Ottawa, Canada) high-pressure homogenizer at 12,000 psi and 2 passes. Five hundred milligrams of polycaprolactone was added directly to the emulsion and, mixed until thoroughly dissolved. The emulsion was then fed into the spray dryer under the conditions described above. A free flowing, white powder was collected at the cyclone separator as is standard for this dryer. The resulting Span 60/polycaprolactone powder had a mean volume weighted particle diameter of 3.15±2.17 µm. Again, the present Example demonstrates the versatility the instant invention with regard to the feed stock used to provide the desired perforated microstructure.

VIII

Preparation of Hollow Porous Powder by Spray Drying a Gas-in-Water Emulsion

The following solutions were prepared with water for injection:

| Solution 1: | |
|---|---|
| 3.9% w/v | m-HES hydroxyethylstarch (Ajinomoto, Tokyo, Japan) |
| 3.25% w/v | Sodium chloride (Mallinckrodt, St. Louis, MO) |
| 2.83% w/v | Sodium phosphate, dibasic (Mallinckrodt, St. Louis, MO) |
| 0.42% w/v | Sodium phosphate, monobasic (Mallinckrodt, St. Louis, MO) |
| Solution 2: | |
| 0.45% w/v | Poloxamer 188 (BASF, Mount Olive, NJ) |
| 1.35% w/v | Hydrogenated egg phosphatidylcholine, EPC-3 (Lipoid KG, Ludwigshafen, Germany) |

The ingredients of solution 1 were dissolved in warm water using a stir plate. The surfactants in solution 2 were dispersed in water using a high shear mixer. The solutions were combined following emulsification and saturated with nitrogen prior to spray drying.

The resulting dry, free flowing, hollow spherical product had a mean particle diameter of 2.6±1.5 μm. The particles were spherical and porous as determined by SEM.

This example illustrates the point that a wide of blowing agents (here nitrogen) may be used to provide microstructures exhibiting the desired morphology. Indeed, one of the primary advantages of the present invention is the ability to alter formation conditions so as to preserve biological activity (i.e. with proteins), or to produce microstructures having selected porosity.

IX

Suspension Stability of Gentamicin Sulfate Spary-Dried Powders

The suspension stability was defined as, the resistance of powders to cream in a nonaqueous medium using a dynamic photosedimentation method. Each sample was suspended in Perflubron at a concentration of 0.8 mg/mL. The creaming rates were measured using a Horiba CAPA-700 photosedimentation particle size analyzer (Irvine, Calif.) under the following conditions:

| | |
|---|---|
| D (max): | 3.00 μm |
| D (min.): | 0.30 μm |
| D (Div): | 0.10 μm |
| Rotor Speed: | 3000 rpm |
| ΔX: | 10 mm |

The suspended particles were subjected to a centrifugal force and the absorbance of the suspension was measured as a function of time. A rapid decrease in the absorbance identifies a suspension with poor stability. Absorbance data was plotted versus time and the area under the curve was integrated between 0.1 and 1 min., which was taken as a relative measurement of stability. FIG. 2 graphically depicts suspension stability as a function of PFC/PC ratio or porosity. In this case, the powder porosity was found to increase with increasing PFC/PC. Maximum suspension stability was observed with formulations having PFC/PC ratios between 3 to 15. For the most part, these formulations appeared stable for periods greater than 30 minutes using visual inspection techniques. At points beyond this ratio, the suspensions flocculated rapidly indicating decreased stability. Similar results were observed using the cream layer ratio method, where it was observed that suspensions with PFC/PC ratios between 3 to 15 had a reduced cream layer thickness, indicating favorable suspension stability.

X

Preparation of Hollow Porous Particles of Albuterol Sulfate by Spray-Drying

Hollow porous albuterol sulfate particles were prepared by a spray-drying technique with a B-191 Mini Spray-Drier (Büchi, Flawil, Switzerland) under the following spray conditions: aspiration: 100%, inlet temperature: 85° C.; outlet temperature: 61° C.; feed pump: 10%; $N_2$ flow: 2,800 L/hr. The feed solution was prepared by mixing two solutions A and B immediately prior to spray drying.

Solution A: 20 g of water was used to dissolve 1 g of albuterol sulfate (Accurate Chemical, Westbury, N.Y.) and 0.021 g of poloxamer 188 NF grade (BASF, Mount Olive, N.J.).

Solution B: A fluorocarbon-in-water emulsion stabilized by phospholipid was prepared in the following manner. The phospholipid, 1 g EPC-100-3 (Lipoid KG, Ludwigshafen, Germany), was homogenized in 150 g of hot deionized water (T=50 to 60° C.) using an Ultra-Turrax mixer (model T-25) at 8000 rpm for 2 to 5 minutes (T=60-70° C.). 25 g of perfluorooctyl bromide (Atochem, Paris, France) was added dropwise during mixing. After the fluorocarbon was added, the emulsion was mixed for a period of not less than 4 minutes. The resulting coarse emulsion was then passed through a high pressure homogenizer (Avestin, Ottawa, Canada) at 18,000 psi for 5 passes.

Solutions A and B were combined and fed into the spray-dryer under the conditions described above. A free flowing, white powder was collected at the cyclone separator. The hollow porous albuterol sulfate particles had a volume-weighted mean aerodynamic diameter of 1.18±1.42 μm as determined by a time-of-flight analytical method (Aerosizer, Amherst Process Instruments, Amherst, Mass.). Scanning electron microscopy (SEM) analysis showed the powders to be spherical and highly porous. The tap density of the powder was determined to be less than 0.1 g/$cm^3$.

This foregoing example serves to illustrate the inherent diversity of the present invention as a drug delivery platform capable of effectively incorporating any one of a number of pharmaceutical agents. The principle is further illustrated in the next example.

XI

Preparation of Hollow Porous Particles of BDP by Spray-Drying

Perforated microstructures comprising beclomethasone dipropionate (BDP) particles were prepared by a spray-drying technique with a B-191 Mini Spray-Drier (Büchi, Flawil, Switzerland) under the following spray conditions: aspiration: 100%, inlet temperature: 85° C.; outlet temperature: 61° C.; feed pump: 10%; $N_2$ flow: 2,800 L/hr. The feed stock was prepared by mixing 0.11 g of lactose with a fluorocarbon-in-water emulsion immediately prior to spray drying. The emulsion was prepared by the technique described below.

74 mg of BDP (Sigma, Chemical Co., St. Louis, Mo.), 0.5 g of EPC-100-3 (Lipoid KG, Ludwigshafen, Germany), 15 mg sodium oleate (Sigma), and 7 mg of poloxamer 188 (BASF, Mount Olive, N.J.) were dissolved in 2 ml of hot methanol. The methanol was then evaporated to obtain a thin film of the phospholipid/steroid mixture. The phospholipid/steroid mixture was then dispersed in 64 g of hot deionized water (T=50 to 60° C.) using an Ultra-Turrax mixer (model T-25) at 8000 rpm for 2 to 5 minutes (T=60-70° C.). 8 g of perflubron (Atochem, Paris, France) was added dropwise during mixing. After the addition was complete, the emulsion was mixed for an additional period of not less than 4 minutes. The resulting coarse emulsion was then passed through a high pressure homogenizer (Avestin, Ottawa, Canada) at 18,000 psi for 5 passes. This emulsion was then used to form the feed stock which was spray dried as described above. A free flowing, white powder was collected at the cyclone separator. The hollow porous BDP particles had a tap density of less than 0.1 g/cm$^3$.

XII

Preparation of Hollow Porous Particles of Cromolyn Sodium by Spray-Drying

Perforated microstructures comprising cromolyn sodium were prepared by a spray-drying technique with a B-191 Mini Spray-Drier (Büchi, Flawil, Switzerland) under the following spray conditions: aspiration: 100%, inlet temperature: 85° C.; outlet temperature: 61° C.; feed pump: 10%; $N_2$ flow: 2,800 L/hr. The feed solution was prepared by mixing two solutions A and B immediately prior to spray drying.

Solution A: 20 g of water was used to dissolve 1 g of cromolyn sodium (Sigma Chemical Co, St. Louis, Mo.) and 0.021 g of poloxamer 188 NF grade (BASF, Mount Olive, N.J.).

Solution B: A fluorocarbon-in-water emulsion stabilized by phospholipid was prepared in the following manner. The phospholipid, 1 g EPC-100-3 (Lipoid KG, Ludwigshafen, Germany), was homogenized in 150 g of hot deionized water (T=50 to 60° C.) using an Ultra-Turrax mixer (model T-25) at 8000 rpm for 2 to 5 minutes (T=60-70° C.). 27 g of perfluorodecalin (Air Products, Allentown, Pa.) was added dropwise during mixing. After the fluorocarbon was added, the emulsion was mixed for at least 4 minutes. The resulting coarse emulsion was then passed through a high pressure homogenizer (Avestin, Ottawa, Canada) at 18,000 psi for 5 passes.

Solutions A and B were combined and fed into the spray dryer under the conditions described above. A free flowing, pale yellow powder was collected at the cyclone separator. The hollow porous cromolyn sodium particles had a volume-weighted mean aerodynamic diameter of 1.23±1.31 μm as determined by a time-of-flight analytical method (Aerosizer, Amherst Process Instruments, Amherst, Mass.). As shown in FIG. 3, scanning electron microscopy (SEM) analysis showed the powders to be both hollow and porous. The tap density of the powder was determined to be less than 0.1 g/$cm^3$.

XIII

Preparation of Hollow Porous Particles of DNase I by Spray-Drying

Hollow porous DNase I particles were prepared by a spray drying technique with a B-191 Mini Spray-Drier (Büchi, Flawil, Switzerland) under the following conditions: aspiration: 100%, inlet temperature: 80° C.; outlet temperature: 61° C.; feed pump: 10%; $N_2$ flow: 2,800 L/hr. The feed was prepared by mixing two solutions A and B immediately prior to spray drying.

Solution A: 20 g of water was used to dissolve 0.5 gr of human pancreas DNase I (Calbiochem, San Diego Calif.) and 0.012 g of poloxamer 188 NF grade (BASF, Mount Olive, N.J.).

Solution B: A fluorocarbon-in-water emulsion stabilized by phospholipid was prepared in the following way. The phospholipid, 0.52 g EPC-100-3 (Lipoid KG, Ludwigshafen, Germany), was homogenized in 87 g of hot deionized water (T=50 to 60° C.) using an Ultra-Turrax mixer (model T-25) at 8000 rpm for 2 to 5 minutes (T=60-70° C.). 13 g of perflubron (Atochem, Paris, France) was added dropwise during mixing. After the fluorocarbon was added, the emulsion was mixed for at least 4 minutes. The resulting coarse emulsion was then passed through a high pressure homogenizer (Avestin, Ottawa, Canada) at 18,000 psi for 5 passes.

Solutions A and B were combined and fed into the spray dryer under the conditions described above. A free flowing, pale yellow powder was collected at the cyclone separator. The hollow porous DNase I particles had a volume-weighted mean aerodynamic diameter of 1.29±1.40 μm as determined by a time-of-flight analytical method (Aerosizer, Amherst Process Instruments, Amherst, Mass.). Scanning electron microscopy (SEM) analysis showed the powders to be both hollow and porous. The tap density of the powder was determined to be less than 0.1 g/$cm^3$.

The foregoing example further illustrates the extraordinary compatibility of the present invention with a variety of bioactive agents. That is, in addition to relatively small, hardy compounds such as steroids, the preparations of the present invention may be formulated to effectively incorporate larger, fragile molecules such as proteins and genetic material.

XIV

Preparation of Perforated Ink Polymeric Particles by Spray Dying

In the following hypothetical example, finely-divided porous spherical resin particles which may contain coloring material such as a pigment, a dye, etc. are formed using the following formulation in accordance with the teachings herein:

| Formulation: | | |
|---|---|---|
| Butadiene | 7.5 g | co-monomer |
| Styrene | 2.5 g | co-monomer |
| Water | 18.0 g | carrier |
| Fatty Acid Soap | 0.5 g | emulsifier |
| n-Dodecyl Mercaptan | 0.050 g | modifier |
| potassium persulfate | 0.030 g | initiator |
| carbon Black | 0.50 g | pigment |

The reaction is allowed to proceed at 50° C. for 8 hours. The reaction is then terminated by spray drying the emulsion using a high pressure liquid chromatography (HPLC) pump. The emulsion is pumped through a 200×0.030 inch i.d. stainless steel tubing into a Niro atomizer portable spray dryer (Niro Atomize, Copenhagen, Denmark) equipped with a two fluid nozzle (0.01" i.d.) employing the following settings:

| | |
|---|---|
| Hot air flow rate: | 39.5 CFM |
| Inlet air temp.: | 180° C. |
| Outlet air temperature: | 80° C. |
| Atomizer nitrogen flow: | 45 L/min, 1,800 psi |
| Liquid feed rate: | 33 mL/min |

It will be appreciated that unreacted monomers serve as blowing agents, creating the perforated microstructure. The described formulation and conditions yield free flowing porous polymeric particles ranging from 0.1-100 μm that may be used in ink formulations. In accordance with the teachings herein the microparticles have the advantage of incorporating the pigment directly into the polymeric matrix. The process allows for the production of different particle sizes by modifying the components and the spray drying conditions with the pigment particle diameter largely dictated by the diameter of the copolymer resin particles.

XV

Andersen Impactor Test for Assessing MDI and DPI Performance

The MDIs and DPIs were tested using commonly accepted pharmaceutical procedures. The method utilized was compliant with the United State Pharmacopeia (USP) procedure (Pharmacopeial Previews (1996) 22:3065-3098) incorporated herein by reference. After 5 shots to waste, 20 shots from the test MDI were made into an Andersen Impactor. The number of shots employed for assessing the DPI formulations was dictated by the drug concentration and ranged from 10 to 20 actuations.

Extraction procedure. The extraction from all the plates, induction port, and actuator were performed in closed vials with 10 mL of a suitable solvent. The filter was installed but not assayed, because the polyacrylic binder interfered with the analysis. The mass balance and particle size distribution trends indicated that the deposition on the filter was negligibly small. Methanol was used for extraction of beclomethasone dipropionate. Deionized water was used for albuterol sulfate, and cromolyn sodium. For albuterol MDIs, 0.5 ml of 1 N sodium hydroxide was added to the plate extract, which was used to convert the albuterol into the phenolate form.

Quantitation procedure. All drugs were quantitated by absorption spectroscopy (Beckman DU640 spectrophotometer) relative to an external standard curve with the extraction solvent as the blank. Beclomethasone dipropionate was quantitated by measuring the absorption of the plate extracts at 238 nm Albuterol MDIs were quantified by measuring the absorption of the extracts at 243 nm, while cromolyn sodium was quantitated using the absorption peak at 326 nm.

Calculation procedure. For each MDI, the mass of the drug in the stem (component-3), actuator (-2), induction port (-1) and plates (0-7) were quantified as described above. Stages-3 and -2 were not quantified for the DPI since this device was only a prototype. The main interest was to assess the aerodynamic properties of the powder which leaves this device. The Fine Particle Dose and Fine Particle Fraction was calculated according to the USP method referenced above. Throat deposition was defined as the mass of drug found in the induction port and on plates 0 and 1. The mean mass aerodynamic diameters (MMAD) and geometric standard diameters (GSD) were evaluated by fitting the experimental cumulative function with log-normal distribution by using two-parameter fitting routine. The results of these experiments are presented in subsequent examples.

XVI

Preparation of Metered Dose Inhalers Containing Hollow Porous Particles

A pre-weighed amount of the hollow porous particles prepared in Examples I, X, XI, and XII were placed into 10 ml aluminum cans, and dried in a vacuum oven under the flow of nitrogen for 3-4 hours at 40° C. The amount of powder filled into the can was determined by the amount of drug required for therapeutic effect. After this, the can was crimp sealed using a DF31/50act 50 μl valve (Valois of America, Greenwich, Conn.) and filled with HFA-134a (DuPont, Wilmington, Del.) propellant by overpressure through the stem. The amount of the propellant in the can was determined by weighing the can before and after the fill.

XVII

Effect of Powder Porosity on MDI Performance

In order to examine the effect powder porosity has upon the suspension stability and aerodynamic diameter, MDIs were prepared as in Example XVI with various preparations of perforated microstructures comprising gentamicin formulations as described in Example I. MDIs containing 0.48 wt % spray dried powders in HFA 134a were studied. As set forth in Example I, the spray dried powders exhibit varying porosity. The formulations were filled in clear glass vials to allow for visual examination.

A strong dependence of the suspension stability and mean volume weighted aerodynamic diameter was observed as a function of PFC/PC ratio and/or porosity. The volume weighted mean aerodynamic diameter (VMAD) decreased and suspension stability increased with increasing porosity. The powders that appeared solid and smooth by SEM and TEM techniques had the worst suspension stability and largest mean aerodynamic diameter. MDIs which were formulated with highly porous and hollow perforated microstructures had the greatest resistance to creaming and the smallest aerodynamic diameters. The measured VMAD values for the dry powders produced in Example I are shown in Table III immediately below.

TABLE III

| PFC/PC | Powder VMAD, μm |
|---|---|
| 0 | 6.1 |
| 1.1 | 5.9 |
| 2.2 | 6.4 |
| 4.8 | 3.9 |
| 18.8 | 2.6 |
| 44.7 | 1.8 |

XVIII

Comparison of Creaming Rates in Cromolyn Sodium Formulations

A comparison of the creaming rates of the commercial Intal formulation (Rhone-Poulenc Rorer) and spray-dried hollow porous particles formulated in HFA-134a according to Example XII (i.e. see FIG. 3) is shown in FIGS. 4A to 4D. In each of the pictures, taken at 0 seconds, 30 seconds, 60 seconds and two hours after shaking, the commercial formulation is on the left and the perforated microstructure dispersion formed accordance with the present invention is on the right. Whereas the commercial Intal formulation shows creaming within 30 seconds of mixing, almost no creaming is noted in the spray-dried particles after 2 hours. Moreover, there was little creaming in perforated microstructure formulation after 4 hours (not shown). This example clearly illustrates the balance in density which can be achieved when the hollow porous particles are filled with the suspension medium (i.e. in the formation of a homodispersion).

XIX

Andersen Cascade Impactor Results for Cromolyn Sodium MDI Formulations

The results of cascade impactor tests for a commercially available product (Intal®, Rhone-Poulenc Rorer) and an analogous spray-dried hollow porous powder in HFA-134a prepared according to Examples XII and XVI are shown below in Table IV. The tests were performed using the protocol set forth in Example XV.

TABLE IV

Cromolyn Sodium MDIs

| | MMAD (GSD) | Throat Deposition, μg | Fine particle fraction, % | Fine Particle Dose, μg |
|---|---|---|---|---|
| Intar®, CFC (n = 4) (Rhone Poulenc) 800 μg dose | 4.7 ± 0.5 (1.9 ± 0.06) | 629 | 24.3 ± 2.1 | 202 ± 27 |
| Spray dried hollow porous powder, HFA (Alliance) (n = 3) 300 μg dose | 3.4 ± 0.2 (2.0 ± 0.3) | 97 | 67.3 ± 5.5 | 200 ± 11 |

The MDI formulated with perforated microstructures was found to have superior aerosol performance compared with Intal®. At a comparable fine particle dose, the spray dried cromolyn formulations possessed a substantially higher fine particle fraction (~67%), and significantly decreased throat deposition (6-fold), along with a smaller MMAD value. It is important to note that the effective delivery provided for by the present invention allowed for a fine particle dose that was approximately the same as the prior art commercial formulation even though the amount of perforated microstructures administered (300 μg) was roughly a third of the Intal® dose administered (800 μg).

XX

Comparison of Andersen Cascade Impactor Results for Albuterol Sulfate Microspheres Delivered from DPIs and MDI The in vitro aerodynamic properties of hollow porous albuterol sulfate microspheres as prepared in Example X was characterized using an Andersen Mark II Cascade Impactor (Andersen Sampler, Atlanta, Ga.) and an Amherst Aerosizer (Amherst Instruments, Amherst, Mass.).

DPI testing. Approximately, 300 mcg of spray-dried microspheres was loaded into a proprietary inhalation device. Activation and subsequent plume generation of the dry powder was achieved by the actuation of 50 μl of pressurized HFA 134a through a long induction tube. The pressurized HFA 134a forced air through the induction tube toward the sample chamber, and subsequently aerosolized a plume of dry powder into the air. The dry powder plume was then taken in the cascade impactor by means of the air flow through drawn through the testing device. A single actuation was discharged into the aerosizer sample chamber for particle size analysis. Ten actuations were discharged from the device into the impactor. A 30 second interval was used between each actuation. The results were quantitated as described in Example XV.

MDI testing. A MDI preparation of albuterol sulfate microspheres was prepared as in Example XVI. A single actuation was discharged into the aerosizer sample chamber for particle size analysis. Twenty actuations were discharged from the device into the impactor. A 30 second interval was used between each actuation. Again, the results were quantitated as described in Example XV.

The results comparing the particle size analysis of the neat albuterol sulfate powder and the albuterol sulfate powder discharged from either a DPI or MDI are shown in Table V below. The albuterol sulfate powder delivered from the DPI was indistinguishable from the neat powder which indicates that little or no aggregation had occurred during actuation. On the other hand, some aggregation was observed using an MDI as evidenced by the larger aerodynamic diameter of particles delivered from the device.

TABLE V

| Sample | Mean Size (μm) | % under 5.4 μm | 95% under (μm) |
|---|---|---|---|
| Neat powder | 1.2 | 100 | 2.0 |
| MDI | 2.4 | 96.0 | 5.1 |
| DPI | 1.1 | 100 | 1.8 |

Figure 5:
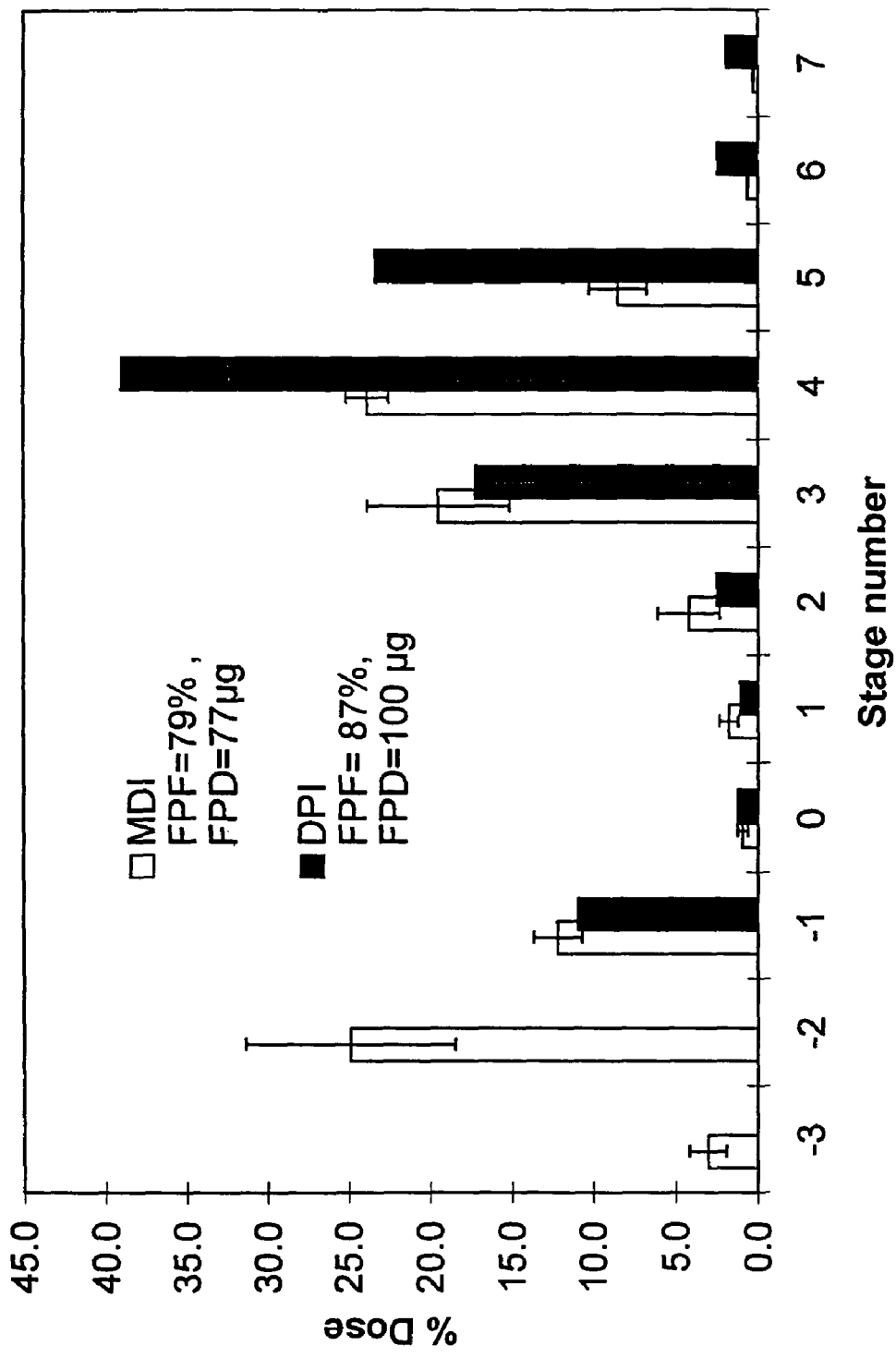
FIG. 5 presents results of in-vitro Andersen cascade impactor studies comparing the same hollow porous albuterol sulfate formulation delivered via a MDI in HFA-134a, or from an exemplary DPI. Efficient delivery of particles was observed from both devices. MDI delivery of the particles was maximized on plate 4 corresponding to upper airway delivery. DPI delivery of the particles results in substantial deposition on the later stages in the impactor corresponding to improved systemic delivery in-vivo.

Similar results were observed when comparing the two dosage forms using an Andersen Cascade Impactor (FIG. 5). The spray-dried albuterol sulfate powder delivered from the DPI had enhanced deep lung deposition and minimized throat deposition when compared with the MDI. The MDI formulation had a fine particle fraction (FPF) of 79% and a fine particle dose (FPD) of 77 μg/actuation, while the DPI had a FPF of 87% and a FPD of 100 μg/actuation.

FIG. 5 and the Example above exemplifies the excellent flow and aerodynamic properties of the herein described spray-dried powders delivered from a DPI. Indeed, one of the primary advantages of the present invention is the ability to produce small aerodynamically light particles which aerosolize with ease and which have excellent inhalation properties. These powders have the unique properties which enable them to be effectively and efficiently delivered from either a MDI or DPI. This principle is further illustrated in the next Example.

XXI

Comparison of Andersen Cascade Impactor Results for Beclomethasone Dipropionate Microspheres Delivered from DPIs and MDIs The in vitro aerodynamic properties of hollow porous beclomethasone dipropionate (BDP) microspheres as prepared in Example XI was characterized using an Andersen Mark II Cascade Impactor (Andersen Sampler, Atlanta, Ga.) and an Amherst Aerosizer (Amherst Instruments, Amherst, Mass.).

DPI testing. Approximately, 300 μg of spray-dried microspheres was loaded into a proprietary inhalation device. Activation and subsequent plume generation of the dry powder was achieved by the actuation of 50 μl of pressurized HFA 134a through a long induction tube. The pressurized HFA 134a forced air through the induction tube toward the sample chamber, and subsequently aerosolized a plume of dry powder into the air. The dry powder plume was then taken in the cascade impactor by means of the air flow through drawn through the testing device. A single actuation was discharged into the aerosizer sample chamber for particle size analysis. Twenty actuations were discharged from the device into the impactor. A 30 second interval was used between each actuation.

MDI testing. A MDI preparation of beclomethasone dipropionate (BDP) microspheres was prepared as in Example XVI. A single actuation was discharged into the aerosizer sample chamber for particle size analysis. Twenty actuations were discharged from the device into the impactor. A 30 second interval was used between each actuation.

The results comparing the particle size analysis of the neat BDP powder and the BDP powder discharged from either a DPI or MDI are shown in Table VI immediately below.

TABLE VI

| Sample | Mean Size (µm) | % under 5.4 µm | 95% under (µm) |
|---|---|---|---|
| Neat powder | 1.3 | 100 | 2.1 |
| MDI | 2.2 | 98.1 | 4.6 |
| DPI | 1.2 | 99.8 | 2.2 |

As with Example XX, the BDP powder delivered from the DPI was indistinguishable from the neat powder which indicates that little or no aggregation had occurred during actuation. On the other hand, some aggregation was observed using an MDI as evidenced by the larger aerodynamic diameter of particles delivered from the device.

The spray-dried BDP powder delivered from the DPI had enhanced deep lung deposition and minimized throat deposition when compared with the MDI. The MDI formulation had a fine particle fraction (FPF) of 79% and a fine particle dose (FPD) of 77 µg/actuation, while the DPI had a FPF of 87% and a FPD of 100 µg/actuation.

This foregoing example serves to illustrate the inherent diversity of the present invention as a drug delivery platform capable of effectively incorporating any one of a number of pharmaceutical agents and effectively delivered from various types of delivery devices (here MDI and DPI) currently used in the pharmaceutical arena. The excellent flow and aerodynamic properties of the dry powders shown in the proceeding examples is further exemplified in the next example.

XXII

Comparison of Andersen Cascade Impactor Results for Albuterol Sulfate Microspheres and Ventolin Rotacaps® from a Rotahaler® Device The following procedure was followed to compare the inhalation properties of Ventolin Rotocaps® (a commercially available formulation) vs. albuterol sulfate hollow porous microspheres formed in accordance with the present invention. Both prepartions were discharged from a Rotohaler® device into an 8 stage Andersen Mark II cascade impactor operated at a flow of 60 L/min. Preparation of the albuterol sulfate microspheres is described in Example X with albuterol sulfate deposition in the cascade impactor analyzed as described in Example XV. Approximately 300 µg of albuterol sulfate microspheres were manually loaded into empty Ventolin Rotocap® gelatin capsules. The procedure described in the package insert for loading and actuating drug capsules with a Rotohaler® device was followed. Ten actuations were discharged from the device into the impactor. A 30 second interval was used between each actuation.

The results comparing the cascade impactor analysis of Ventolin Rotocaps® and hollow porous albuterol sulfate microspheres discharged from a Rotohaler® device are shown in Table VI immediately below.

TABLE VII

| Sample | MMAD (GSD) | Fine Particle Fraction % | Fine Particle Dose (mcg/dose) |
|---|---|---|---|
| Ventolin Rotacaps ® (n = 2) | 7.869 (1.6064) | 20 | 15 |
| Albuterol Sulfate Microspheres (n = 3) | 4.822 (1.9082) | 63 | 60 |

The hollow porous albuterol sulfate powder delivered from the Rotohaler® device had a significantly higher fine particle fraction (3-fold) and a smaller MMAD value as compared with Ventolin Rotocaps®. In this regard, the commercially available Ventolin Rotocap® formulation had a fine particle fraction (FPF) of 20% and a fine particle dose (FPD) of 15 µg/actuation, whereas the hollow porous albuterol sulfate microspheres had a FPF of 63% and a FPD of 60 µg/actuation.

The example above exemplifies the excellent flow and aerodynamic properties of the spray-dried powders delivered from a Rotahaler® device. Moreover, this example demonstrates that fine powders can be effectively delivered without carrier particles.

XXIII

Nebulization of Porous Particulate Structures Comprising Phospholipids and Cromolyn Sodium in Perfluorooctylethane Using a MicroMist™ Nebulizer Forty milligrams of the lipid based microspheres containing 50% cromolyn sodium by weight (as from Example XII) were dispersed in 10 ml perfluorooctylethane (PFOE) by shaking, forming a suspension. The suspension was nebulized until the fluorocarbon liquid was delivered or had evaporated using a MicroMist™ (DeVilbiss) disposable nebulizer using a PulmoAide® air compressor (DeVilbiss). As described above in Example XV, an Andersen Cascade Impactor was used to measure the resulting particle size distribution. More specifically, cromolyn sodium content was measured by UV adsorption at 326 nm. The fine particle fraction is the ratio of particles deposited in stages 2 through 7 to those deposited in all stages of the impactor. The fine particle mass is the weight of material deposited in stages 2 through 7. The deep lung fraction is the ratio of particles deposited in stages 5 through 7 of the impactor (which correlate to the alveoli) to those deposited in all stages. The deep lung mass is the weight of material deposited in stages 5 through 7. Table VIII immediately below provides a summary of the results.

TABLE VIII

| Fine particle fraction | fine particle mass | deep lung fraction | deep lung mass |
|---|---|---|---|
| 90% | 6 mg | 75% | 5 mg |

XXIV

Nebulization of Porous Particulate Structures Comprising Phospholipids and Cromolyn Sodium in Perfluorooctylethane Using a Raindrop® Nebulizer A quantity of lipid based microspheres containing 50% cromolyn sodium, as from Example XII, weighing 40 mg was dispersed in 10 ml perfluorooctylethane (PFOE) by shaking, thereby forming a suspension. The suspension was nebulized until the fluorocarbon liquid was delivered or had evaporated using a Raindrop® disposable nebulizer (Nellcor Puritan Bennet) connected to a PulmoAide® air compressor (DeVilbiss). An Andersen Cascade Impactor was used to measure the resulting particle size distribution in the manner described in Examples XV and XXIII. Table IX immediately below provides a summary of the results.

TABLE IX

| Fine particle fraction | fine particle mass | Deep lung fraction | deep lung mass |
|---|---|---|---|
| 90% | 4 mg | 80% | 3 mg |

XXV

Nebulization of Aqueous Cromolyn Sodium Solution

The contents of plastic vial containing a unit dose inhalation solution of 20 mg of cromolyn sodium in 2 ml purified water (Dey Laboratories) was nebulized using a MicroMist™ disposable nebulizer (DeVilbiss) using a PulmoAide® air compressor (DeVilbiss). The cromolyn sodium solution was nebulized for 30 minutes. An Andersen Cascade Impactor was used to measure the resulting size distribution of the nebulized particles, by the method described above in Example XV. Table X immediately below provides a summary of the results.

TABLE X

| fine particle fraction | fine particle mass | Deep lung fraction | Deep lung mass |
|---|---|---|---|
| 90% | 7 mg | 60% | 5 mg |

With regard to the instant results, it will be appreciated that, the formulations nebulized from fluorocarbon suspension mediums in Examples XXIII and XXIV provided a greater percentage of deep lung deposition than the aqueous solution. Such high deposition rates deep in the lung is particularly desirable when delivering agents to the systemic circulation of a patient.

Those skilled in the art will further appreciate that the present invention may be embodied in other specific forms without departing from the spirit or central attributes thereof. In that the foregoing description of the present invention discloses only exemplary embodiments thereof, it is to be understood that, other variations are contemplated as being within the scope of the present invention. Accordingly, the present invention is not limited to the particular embodiments which have been described in detail herein. Rather, reference should be made to the appended claims as indicative of the scope and content of the invention.

The invention claimed is:

1. An inhaleable powder composition comprising a plurality of particulate microstructures, the particulate microstructures comprising:
    (a) a structural matrix comprising phospholipid and calcium, wherein the particulate microstructures comprise greater than about 50% phospholipid;
    (b) an active agent;
    (c) a mean geometric diameter of 1-30 microns;
    (d) a mean aerodynamic diameter of less than 5 microns; and
    (e) a bulk density of less than about 0.5 g/cm$^3$.

2. The composition of claim 1 wherein the particulate microstructures are porous and have a mean porosity of 0.5-80%.

3. The composition of claim 2 wherein the particulate microstructures have a mean porosity of 2-40%.

4. The composition of claim 3 wherein the particulate microstructures have a mean pore size of 20-200 nm.

5. The composition of claim 1 wherein the fine particle fraction of the particulate microstructures in the composition is greater than 20% w/w.

6. The composition of claim 5 wherein the fine particle fraction of the particulate microstructures in the composition is from about 30% to 70% w/w.

7. The composition of claim 1 wherein the particulate microstructures comprise a bulk density of less than 0.1 g/cm$^3$.

8. The composition of claim 7 wherein the particulate microstructures comprise a bulk density of less than 0.05 g/cm$^3$.

9. The composition of claim 1 wherein the particulate microstructures comprise perforated microstructures.

10. The composition of claim 1 wherein said particulate microstructures comprise hollow microspheres.

11. The composition of claim 1 wherein the particulate microspheres comprise a shell with a thickness of 0.1-0.5 µm.

12. The composition of claim 1 wherein the particulate microstructures comprise a mean aerodynamic diameter of between 0.5 µm and 5 µm.

13. The composition of claim 1 wherein the particulate microstructures comprise a mean geometric diameter of less than 10 microns.

14. The composition of claim 13 wherein the particulate microstructures comprise mean geometric diameter is less than 5 microns.

15. The composition of claim 1 wherein the phospholipid comprises a gel to liquid crystal transition temperature of greater than 40° C.

16. The composition of claim 1 wherein the phospholipid comprises a zwitterionic phospholipid.

17. The composition of claim 1 wherein the phospholipid comprises at least one of dilauroylphosphatidylcholine, dioleoylphosphatidylcholine, dipalmitoylphosphatidylcholine, disteroylphosphatidylcholine dibehenoylphosphatidylcholine, diarachidoylphosphatidylcholine and combinations thereof.

18. The composition of claim 1 wherein the active agent is a bioactive agent.

19. The composition of claim 18 wherein the bioactive agent comprises at least one of antiallergics, bronchodilators, pulmonary lung surfactants, analgesics, antibiotics, antiinfectives, leukotriene inhibitors or antagonists, antihistamines, antiinflammatories, antineoplastics, anticholinergics, anesthetics. antituberculars, antivirals, fungicides, immunoactive agents, vaccines, immunosuppressive agents, imaging agents, cardiovascular agents, enzymes, steroids, DNA, RNA, viral vectors, antisense agents, proteins, peptides and combinations thereof.

20. The composition of claim 18 wherein the bioactive agent comprises at least one of fentanyl, morphine, lung surfactant, leuprolide, interferon, insulin, budesonide, formoterol, goserelin, and growth hormones.

21. The composition of claim 18 wherein the bioactive agent is an aminoglycoside antibiotic.

22. The composition of claim 18 wherein the bioactive agent is a fungicide.

23. A composition comprising a plurality of particulate microstructures, the particulate microstructures comprising:
(a) a structural matrix comprising phospholipid and calcium, the phospholipid comprising a gel to liquid crystal transition temperature of greater than 40° C., wherein greater than about 50% of the particulate microstructures comprise phospholipid;
(b) an active agent;
(c) a mean geometric diameter of 1-30 microns;
(d) a mean aerodynamic diameter of less than 5 microns; and
(e) a bulk density of less than about 0.5 g/cm$^3$.

24. The composition of claim 23 wherein the particulate microstructures are porous and have a mean porosity of 0.5-80%.

25. The composition of claim 24 wherein the particulate microstructures have a mean porosity of 2-40%.

26. The composition of claim 24 wherein the particulate microstructures have a mean pore size of 20-200 nm.

27. The composition of claim 23 wherein the fine particle fraction of the particulate microstructures in the composition is greater than 20% w/w.

28. The composition of claim 27 wherein the fine particle fraction of the particulate microstructures in the composition is from about 30% to 70% w/w.

29. The composition of claim 23 wherein the particulate microstructures comprise a bulk density of less than 0.1 g/cm$^3$.

30. The composition of claim 29 wherein the particulate microstructures comprise a bulk density of less than 0.05 g/cm$^3$.

31. The composition of claim 23 wherein the particulate microstructures comprise perforated microstructures.

32. The composition of claim 23 wherein said particulate microstructures comprise hollow microspheres.

33. The composition of claim 23 wherein the particulate microspheres comprise a shell with a thickness of 0.1-0.5 μm.

34. The composition of claim 23 wherein the particulate microstructures comprise a mean aerodynamic diameter of between 0.5 μm and 5 μm.

35. The composition of claim 23 wherein the particulate microstructures comprise a mean geometric diameter of less than 10 microns.

36. The composition of claim 35 wherein the particulate microstructures comprise mean geometric diameter is less than 5 microns.

37. The composition of claim 23 wherein the phospholipid comprises a gel to liquid crystal transition temperature of greater than 40° C.

38. The composition of claim 23 wherein the phospholipid comprises a zwitterionic phospholipid.

39. The composition of claim 23 wherein the phospholipid comprises at least one of dilauroylphosphatidylcholine, dioleoylphosphatidylcholine, dipalmitoylphosphatidylcholine, disteroylphosphatidylcholine dibehenoylphosphatidylcholine, diarachidoylphosphatidylcholine and combinations thereof.

40. The composition of claim 23 wherein the active agent is a bioactive agent.

41. The composition of claim 40 wherein the bioactive agent comprises at least one of antiallergics, bronchodilators, pulmonary lung surfactants, analgesics, antibiotics, antiinfectives, leukotriene inhibitors or antagonists, antihistamines, antiinflammatories, antineoplastics, anticholinergics, anesthetics. antituberculars, antivirals, fungicides, immunoactive agents, vaccines, immunosuppressive agents, imaging agents, cardiovascular agents, enzymes, steroids, DNA, RNA, viral vectors, antisense agents, proteins, peptides and combinations thereof.

42. The composition of claim 40 wherein the bioactive agent comprises at least one of fentanyl, morphine, lung surfactant, leuprolide, interferon, insulin, budesonide, formoterol, goserelin, and growth hormones.

43. The composition of claim 40 wherein the bioactive agent is an aminoglycoside antibiotic.

44. The composition of claim 40 wherein the bioactive agent is a fungicide.

* * * * *